(12) United States Patent
Vandike et al.

(10) Patent No.: US 11,889,788 B2
(45) Date of Patent: Feb. 6, 2024

(54) PREDICTIVE BIOMASS MAP GENERATION AND CONTROL

(71) Applicant: Deere & Company, Moline, IL (US)

(72) Inventors: Nathan R Vandike, Geneseo, IL (US); Bhanu Kiran Reddy Palla, Bettendorf, IA (US); Noel W. Anderson, Fargo, ND (US)

(73) Assignee: Deere & Company, Moline, IL (US)

( * ) Notice: Subject to any disclaimer, the term of this patent is extended or adjusted under 35 U.S.C. 154(b) by 727 days.

(21) Appl. No.: 17/067,086

(22) Filed: Oct. 9, 2020

(65) Prior Publication Data
US 2022/0110248 A1 Apr. 14, 2022

(51) Int. Cl.
*A01D 41/127* (2006.01)
*A01F 12/56* (2006.01)
(Continued)

(52) U.S. Cl.
CPC ............ *A01D 41/127* (2013.01); *A01F 12/56* (2013.01); *G01B 11/0608* (2013.01); *G01L 5/00* (2013.01);
(Continued)

(58) Field of Classification Search
CPC .............. A01D 41/127; A01D 41/1278; A01D 41/141; A01D 41/00; A01F 12/56; G01B 11/0608; G01B 11/022; G01L 5/00; G01L 23/00; G01N 33/0098; G01S 19/01; G01S 17/88; G01S 13/88; G06N 20/00;
(Continued)

(56) References Cited

U.S. PATENT DOCUMENTS

| | | | |
|---|---|---|---|
| 3,568,157 | A | 3/1971 | Downing et al. |
| 3,580,257 | A | 5/1971 | Teague |

(Continued)

FOREIGN PATENT DOCUMENTS

| | | |
|---|---|---|
| AR | 108898 A1 | 10/2018 |
| AU | 20100224431 A1 | 4/2011 |

(Continued)

OTHER PUBLICATIONS

7 Combine Tweaks to Boost Speed (https://www.agriculture.com/machinery/harvest-equipment/7-combine-tweaks-to-boost-speed_203-ar33059) 8 pages, Aug. 19, 2018.

(Continued)

*Primary Examiner* — Muhammad Shafi
(74) *Attorney, Agent, or Firm* — Joseph R. Kelly; Kelly, Holt & Christenson PLLC

(57) ABSTRACT

One or more information maps are obtained by an agricultural work machine. The one or more information maps map one or more agricultural characteristic values at different geographic locations of a field. An in-situ sensor on the agricultural work machine senses an agricultural characteristic as the agricultural work machine moves through the field. A predictive map generator generates a predictive map that predicts a predictive agricultural characteristic at different locations in the field based on a relationship between the values in the one or more information maps and the agricultural characteristic sensed by the in-situ sensor. The predictive map can be output and used in automated machine control.

18 Claims, 11 Drawing Sheets

(51) Int. Cl.
   *G01B 11/06* (2006.01)
   *G01S 19/01* (2010.01)
   *G01N 33/00* (2006.01)
   *G01L 23/00* (2006.01)
   *G06N 20/00* (2019.01)
   *G01L 5/00* (2006.01)
   *G06V 20/10* (2022.01)
   *A01D 41/14* (2006.01)

(52) U.S. Cl.
   CPC .......... *G01L 23/00* (2013.01); *G01N 33/0098* (2013.01); *G01S 19/01* (2013.01); *G06N 20/00* (2019.01); *G06V 20/188* (2022.01); *A01D 41/1278* (2013.01); *A01D 41/141* (2013.01)

(58) Field of Classification Search
   CPC .... G06V 20/188; G06V 10/776; A01B 69/00; A01B 79/005
   USPC ........................................................ 701/50
   See application file for complete search history.

(56) References Cited

U.S. PATENT DOCUMENTS

| | | |
|---|---|---|
| 3,599,543 A | 8/1971 | Norman |
| 3,775,019 A | 11/1973 | Konig et al. |
| 3,856,754 A | 12/1974 | Habermeier et al. |
| 4,129,573 A | 12/1978 | Bellus et al. |
| 4,166,735 A | 9/1979 | Pilgram et al. |
| 4,183,742 A | 1/1980 | Sasse et al. |
| 4,268,679 A | 5/1981 | Lavanish |
| 4,349,377 A | 9/1982 | Durr et al. |
| 4,360,677 A | 11/1982 | Doweyko et al. |
| 4,435,203 A | 3/1984 | Funaki et al. |
| 4,493,726 A | 1/1985 | Burdeska et al. |
| 4,527,241 A | 7/1985 | Sheehan et al. |
| 4,566,901 A | 1/1986 | Martin et al. |
| 4,584,013 A | 4/1986 | Brunner |
| 4,687,505 A | 8/1987 | Sylling et al. |
| 4,857,101 A | 8/1989 | Musco et al. |
| 4,911,751 A | 3/1990 | Nyffeler et al. |
| 5,059,154 A | 10/1991 | Reyenga |
| 5,089,043 A | 2/1992 | Hayase et al. |
| 5,246,164 A | 9/1993 | McCann et al. |
| 5,246,915 A | 9/1993 | Lutz et al. |
| 5,250,690 A | 10/1993 | Turner et al. |
| 5,296,702 A | 3/1994 | Beck et al. |
| 5,300,477 A | 4/1994 | Tice |
| 5,416,061 A | 5/1995 | Hewett et al. |
| 5,477,459 A | 12/1995 | Clegg et al. |
| 5,488,817 A | 2/1996 | Paquet et al. |
| 5,563,112 A | 10/1996 | Barnes |
| 5,585,626 A | 12/1996 | Beck et al. |
| 5,586,033 A | 12/1996 | Hall |
| 5,592,606 A | 1/1997 | Myers |
| 5,606,821 A | 3/1997 | Sadjadi et al. |
| 5,666,793 A | 9/1997 | Bottinger |
| 5,712,782 A | 1/1998 | Weigelt et al. |
| 5,721,679 A | 2/1998 | Monson |
| 5,767,373 A | 6/1998 | Ward et al. |
| 5,771,169 A | 6/1998 | Wendte |
| 5,789,741 A | 8/1998 | Kinter et al. |
| 5,809,440 A | 9/1998 | Beck et al. |
| 5,841,282 A | 11/1998 | Christy et al. |
| 5,849,665 A | 12/1998 | Gut et al. |
| 5,878,821 A | 3/1999 | Flenker et al. |
| 5,899,950 A | 5/1999 | Milender et al. |
| 5,902,343 A | 5/1999 | Hale et al. |
| 5,915,492 A | 6/1999 | Yates et al. |
| 5,957,304 A | 9/1999 | Dawson |
| 5,974,348 A | 10/1999 | Rocks |
| 5,978,723 A | 11/1999 | Hale et al. |
| 5,991,687 A | 11/1999 | Hale et al. |
| 5,991,694 A | 11/1999 | Gudat et al. |
| 5,995,859 A | 11/1999 | Takahashi |
| 5,995,894 A | 11/1999 | Wendte |
| 5,995,895 A | 11/1999 | Watt et al. |
| 6,004,076 A | 12/1999 | Cook et al. |
| 6,016,713 A | 1/2000 | Hale |
| 6,029,106 A | 2/2000 | Hale et al. |
| 6,041,582 A | 3/2000 | Tiede et al. |
| 6,073,070 A | 6/2000 | Diekhans |
| 6,073,428 A | 6/2000 | Diekhans |
| 6,085,135 A | 7/2000 | Steckel |
| 6,119,442 A | 9/2000 | Hale |
| 6,119,531 A | 9/2000 | Wendte et al. |
| 6,128,574 A | 10/2000 | Diekhans |
| 6,141,614 A | 10/2000 | Janzen et al. |
| 6,178,253 B1 | 1/2001 | Hendrickson et al. |
| 6,185,990 B1 | 2/2001 | Missotten et al. |
| 6,188,942 B1 | 2/2001 | Corcoran et al. |
| 6,199,000 B1 | 3/2001 | Keller et al. |
| 6,204,856 B1 | 3/2001 | Wood et al. |
| 6,205,381 B1 | 3/2001 | Motz et al. |
| 6,205,384 B1 | 3/2001 | Diekhans |
| 6,216,071 B1 | 4/2001 | Motz |
| 6,236,924 B1 | 5/2001 | Motz et al. |
| 6,272,819 B1 | 8/2001 | Wendte et al. |
| 6,327,569 B1 | 12/2001 | Reep |
| 6,374,173 B1 | 4/2002 | Ehlbeck |
| 6,380,745 B1 | 4/2002 | Anderson et al. |
| 6,431,790 B1 | 8/2002 | Anderegg et al. |
| 6,451,733 B1 | 9/2002 | Pidskalny et al. |
| 6,505,146 B1 | 1/2003 | Blackmer |
| 6,505,998 B1 | 1/2003 | Bullivant |
| 6,539,102 B1 | 3/2003 | Anderson et al. |
| 6,549,849 B2 | 4/2003 | Lange et al. |
| 6,584,390 B2 | 6/2003 | Beck |
| 6,591,145 B1 | 7/2003 | Hoskinson et al. |
| 6,591,591 B2 | 7/2003 | Coers et al. |
| 6,592,453 B2 | 7/2003 | Coers et al. |
| 6,604,432 B1 | 8/2003 | Hamblen et al. |
| 6,681,551 B1 | 1/2004 | Sheidler et al. |
| 6,682,416 B2 | 1/2004 | Behnke et al. |
| 6,687,616 B1 | 2/2004 | Peterson et al. |
| 6,729,189 B2 | 5/2004 | Paakkinen |
| 6,735,568 B1 | 5/2004 | Buckwalter et al. |
| 6,834,550 B2 | 12/2004 | Upadhyaya et al. |
| 6,838,564 B2 | 1/2005 | Edmunds et al. |
| 6,846,128 B2 | 1/2005 | Sick |
| 6,932,554 B2 | 8/2005 | Isfort et al. |
| 6,999,877 B1 | 2/2006 | Dyer et al. |
| 7,073,374 B2 | 7/2006 | Berkman |
| 7,167,797 B2 | 1/2007 | Faivre et al. |
| 7,167,800 B2 | 1/2007 | Faivre et al. |
| 7,191,062 B2 | 3/2007 | Chi et al. |
| 7,194,965 B2 | 3/2007 | Hickey et al. |
| 7,211,994 B1 | 5/2007 | Mergen et al. |
| 7,248,968 B2 | 7/2007 | Reid |
| 7,255,016 B2 | 8/2007 | Burton |
| 7,261,632 B2 | 8/2007 | Pirro et al. |
| 7,302,837 B2 | 12/2007 | Wendt |
| 7,308,326 B2 | 12/2007 | Maertens et al. |
| 7,313,478 B1 | 12/2007 | Anderson et al. |
| 7,318,010 B2 | 1/2008 | Anderson |
| 7,347,168 B2 | 3/2008 | Reckels et al. |
| 7,408,145 B2 | 8/2008 | Holland |
| 7,480,564 B2 | 1/2009 | Metzler et al. |
| 7,483,791 B2 | 1/2009 | Anderegg et al. |
| 7,537,519 B2 | 5/2009 | Huster et al. |
| 7,557,066 B2 | 7/2009 | Hills et al. |
| 7,628,059 B1 | 12/2009 | Scherbring |
| 7,687,435 B2 | 3/2010 | Witschel et al. |
| 7,703,036 B2 | 4/2010 | Satterfield et al. |
| 7,725,233 B2 | 5/2010 | Hendrickson et al. |
| 7,733,416 B2 | 6/2010 | Gal |
| 7,756,624 B2 | 7/2010 | Diekhans et al. |
| 7,798,894 B2 | 9/2010 | Isfort |
| 7,827,042 B2 | 11/2010 | Jung et al. |
| 7,915,200 B2 | 3/2011 | Epp et al. |
| 7,945,364 B2 | 5/2011 | Schricker et al. |
| 7,993,188 B2 | 8/2011 | Ritter |
| 8,024,074 B2 | 9/2011 | Stelford et al. |
| 8,060,283 B2 | 11/2011 | Mott et al. |

(56) References Cited

U.S. PATENT DOCUMENTS

| | | |
|---|---|---|
| 8,107,681 B2 | 1/2012 | Gaal |
| 8,145,393 B2 | 3/2012 | Foster et al. |
| 8,147,176 B2 | 4/2012 | Coers et al. |
| 8,152,610 B2 | 4/2012 | Harrington |
| 8,190,335 B2 | 5/2012 | Vik et al. |
| 8,195,342 B2 | 6/2012 | Anderson |
| 8,195,358 B2 | 6/2012 | Anderson |
| 8,213,964 B2 | 7/2012 | Fitzner et al. |
| 8,224,500 B2 | 7/2012 | Anderson |
| 8,252,723 B2 | 8/2012 | Jakobi et al. |
| 8,254,351 B2 | 8/2012 | Fitzner et al. |
| 8,321,365 B2 | 11/2012 | Anderson |
| 8,329,717 B2 | 12/2012 | Minn et al. |
| 8,332,105 B2 | 12/2012 | Laux |
| 8,338,332 B1 | 12/2012 | Hacker et al. |
| 8,340,862 B2 | 12/2012 | Baumgarten et al. |
| 8,407,157 B2 | 3/2013 | Anderson et al. |
| 8,428,829 B2 | 4/2013 | Brunnert et al. |
| 8,478,493 B2 | 7/2013 | Anderson |
| 8,488,865 B2 | 7/2013 | Hausmann et al. |
| 8,494,727 B2 | 7/2013 | Green et al. |
| 8,527,157 B2 | 9/2013 | Imhof et al. |
| 8,544,397 B2 | 10/2013 | Bassett |
| 8,577,561 B2 | 11/2013 | Green et al. |
| 8,606,454 B2 | 12/2013 | Wang et al. |
| 8,626,406 B2 | 1/2014 | Schleicher et al. |
| 8,635,903 B2 | 1/2014 | Oetken et al. |
| 8,649,940 B2 | 2/2014 | Bonefas |
| 8,656,693 B2 | 2/2014 | Madsen et al. |
| 8,662,972 B2 | 3/2014 | Behnke et al. |
| 8,671,760 B2 | 3/2014 | Wallrath et al. |
| 8,677,724 B2 | 3/2014 | Chaney et al. |
| 8,738,238 B2 | 5/2014 | Rekow |
| 8,738,244 B2 | 5/2014 | Lenz et al. |
| 8,755,976 B2 | 6/2014 | Peters et al. |
| 8,781,692 B2 | 7/2014 | Kormann |
| 8,789,563 B2 | 7/2014 | Wenzel |
| 8,814,640 B2 | 8/2014 | Behnke et al. |
| 8,843,269 B2 | 9/2014 | Anderson et al. |
| 8,868,304 B2 | 10/2014 | Bonefas |
| 8,909,389 B2 | 12/2014 | Meyer |
| D721,740 S | 1/2015 | Schmaltz et al. |
| 8,942,860 B2 | 1/2015 | Morselli |
| 8,962,523 B2 | 2/2015 | Rosinger et al. |
| 9,002,591 B2 | 4/2015 | Wang et al. |
| 9,008,918 B2 | 4/2015 | Missotten et al. |
| 9,009,087 B1 | 4/2015 | Mewes et al. |
| 9,011,222 B2 | 4/2015 | Johnson et al. |
| 9,014,901 B2 | 4/2015 | Wang et al. |
| 9,043,096 B2 | 5/2015 | Zielke et al. |
| 9,043,129 B2 | 5/2015 | Bonefas et al. |
| 9,066,465 B2 | 6/2015 | Hendrickson et al. |
| 9,072,227 B2 | 7/2015 | Wenzel |
| 9,095,090 B2 | 8/2015 | Casper et al. |
| 9,119,342 B2 | 9/2015 | Bonefas |
| 9,127,428 B2 | 9/2015 | Meier |
| 9,131,644 B2 | 9/2015 | Osborne |
| 9,152,938 B2 | 10/2015 | Lang et al. |
| 9,173,339 B2 | 11/2015 | Sauder et al. |
| 9,179,599 B2 | 11/2015 | Bischoff |
| 9,188,518 B2 | 11/2015 | Snyder et al. |
| 9,188,986 B2 | 11/2015 | Baumann |
| 9,220,196 B2 | 12/2015 | Baumgarten et al. |
| 9,226,449 B2 | 1/2016 | Bischoff |
| 9,234,317 B2 | 1/2016 | Chi |
| 9,235,214 B2 | 1/2016 | Anderson |
| 9,301,447 B2 | 4/2016 | Kormann |
| 9,301,466 B2 | 4/2016 | Kelly |
| 9,313,951 B2 | 4/2016 | Herman et al. |
| 9,326,443 B2 | 5/2016 | Zametzer et al. |
| 9,326,444 B2 | 5/2016 | Bonefas |
| 9,392,746 B2 | 7/2016 | Darr et al. |
| 9,405,039 B2 | 8/2016 | Anderson |
| 9,410,840 B2 | 8/2016 | Acheson et al. |
| 9,439,342 B2 | 9/2016 | Pasquier |
| 9,457,971 B2 | 10/2016 | Bonefas et al. |
| 9,463,939 B2 | 10/2016 | Bonefas et al. |
| 9,485,905 B2 | 11/2016 | Jung et al. |
| 9,489,576 B2 | 11/2016 | Johnson et al. |
| 9,497,898 B2 | 11/2016 | Hennes |
| 9,510,508 B2 | 12/2016 | Jung |
| 9,511,633 B2 | 12/2016 | Anderson et al. |
| 9,511,958 B2 | 12/2016 | Bonefas |
| 9,516,812 B2 | 12/2016 | Baumgarten et al. |
| 9,521,805 B2 | 12/2016 | Muench et al. |
| 9,522,791 B2 | 12/2016 | Bonefas et al. |
| 9,522,792 B2 | 12/2016 | Bonefas et al. |
| 9,523,180 B2 | 12/2016 | Deines |
| 9,529,364 B2 | 12/2016 | Foster et al. |
| 9,532,504 B2 | 1/2017 | Herman et al. |
| 9,538,714 B2 | 1/2017 | Anderson |
| 9,563,492 B2 | 2/2017 | Bell et al. |
| 9,563,848 B1 | 2/2017 | Hunt |
| 9,563,852 B1 | 2/2017 | Wiles et al. |
| 9,578,808 B2 | 2/2017 | Dybro et al. |
| 9,629,308 B2 | 4/2017 | Schøler et al. |
| 9,631,964 B2 | 4/2017 | Gelinske et al. |
| 9,642,305 B2 | 5/2017 | Nykamp et al. |
| 9,648,807 B2 | 5/2017 | Escher et al. |
| 9,675,008 B1 | 6/2017 | Rusciolelli et al. |
| 9,681,605 B2 | 6/2017 | Noonan et al. |
| 9,694,712 B2 | 7/2017 | Healy |
| 9,696,162 B2 | 7/2017 | Anderson |
| 9,699,967 B2 | 7/2017 | Palla et al. |
| 9,714,856 B2 | 7/2017 | Myers |
| 9,717,178 B1 | 8/2017 | Sauder et al. |
| 9,721,181 B2 | 8/2017 | Guan et al. |
| 9,723,790 B2 | 8/2017 | Berry et al. |
| 9,740,208 B2 | 8/2017 | Sugumaran et al. |
| 9,767,521 B2 | 9/2017 | Stuber et al. |
| 9,807,934 B2 | 11/2017 | Rusciolelli et al. |
| 9,807,940 B2 | 11/2017 | Roell et al. |
| 9,810,679 B2 | 11/2017 | Kimmel |
| 9,829,364 B2 | 11/2017 | Wilson et al. |
| 9,848,528 B2 | 12/2017 | Werner et al. |
| 9,856,609 B2 | 1/2018 | Dehmel |
| 9,856,612 B2 | 1/2018 | Oetken |
| 9,861,040 B2 | 1/2018 | Bonefas |
| 9,872,433 B2 | 1/2018 | Acheson et al. |
| 9,903,077 B2 | 2/2018 | Rio |
| 9,903,979 B2 | 2/2018 | Dybro et al. |
| 9,904,963 B2 | 2/2018 | Rupp et al. |
| 9,915,952 B2 | 3/2018 | Dollinger et al. |
| 9,922,405 B2 | 3/2018 | Sauder et al. |
| 9,924,636 B2 | 3/2018 | Lisouski et al. |
| 9,928,584 B2 | 3/2018 | Jens et al. |
| 9,933,787 B2 | 4/2018 | Story |
| 9,974,226 B2 | 5/2018 | Rupp et al. |
| 9,982,397 B2 | 5/2018 | Korb et al. |
| 9,984,455 B1 | 5/2018 | Fox et al. |
| 9,992,931 B2 | 6/2018 | Bonefas et al. |
| 9,992,932 B2 | 6/2018 | Bonefas et al. |
| 10,004,176 B2 | 6/2018 | Mayerle |
| 10,015,928 B2 | 7/2018 | Nykamp et al. |
| 10,019,018 B2 | 7/2018 | Hulin |
| 10,019,790 B2 | 7/2018 | Bonefas et al. |
| 10,025,983 B2 | 7/2018 | Guan et al. |
| 10,028,435 B2 | 7/2018 | Anderson et al. |
| 10,028,451 B2 | 7/2018 | Rowan et al. |
| 10,034,427 B2 | 7/2018 | Krause et al. |
| 10,039,231 B2 | 8/2018 | Anderson et al. |
| 10,064,331 B2 | 9/2018 | Bradley |
| 10,064,335 B2 | 9/2018 | Byttebier et al. |
| 10,078,890 B1 | 9/2018 | Tagestad et al. |
| 10,085,372 B2 | 10/2018 | Noyer et al. |
| 10,091,925 B2 * | 10/2018 | Aharoni ............... A01B 79/005 |
| 10,126,153 B2 | 11/2018 | Bischoff et al. |
| 10,129,528 B2 | 11/2018 | Bonefas et al. |
| 10,143,132 B2 | 12/2018 | Inoue et al. |
| 10,152,035 B2 | 12/2018 | Reid et al. |
| 10,154,624 B2 | 12/2018 | Guan et al. |
| 10,165,725 B2 | 1/2019 | Sugumaran et al. |
| 10,178,823 B2 | 1/2019 | Kovach et al. |
| 10,183,667 B2 | 1/2019 | Anderson et al. |

(56) References Cited

U.S. PATENT DOCUMENTS

| | | |
|---|---|---|
| 10,188,037 B2 | 1/2019 | Bruns et al. |
| 10,201,121 B1 | 2/2019 | Wilson |
| 10,209,179 B2 | 2/2019 | Hollstein |
| 10,231,371 B2 | 3/2019 | Dillon |
| 10,254,147 B2 | 4/2019 | Vermue et al. |
| 10,254,765 B2 | 4/2019 | Rekow |
| 10,255,670 B1 | 4/2019 | Wu et al. |
| 10,275,550 B2 | 4/2019 | Lee |
| 10,295,703 B2 | 5/2019 | Dybro et al. |
| 10,310,455 B2 | 6/2019 | Blank et al. |
| 10,314,232 B2 | 6/2019 | Isaac et al. |
| 10,315,655 B2 | 6/2019 | Blank et al. |
| 10,317,272 B2 | 6/2019 | Bhavsar et al. |
| 10,351,364 B2 | 7/2019 | Green et al. |
| 10,368,488 B2 | 8/2019 | Becker et al. |
| 10,398,084 B2 | 9/2019 | Ray et al. |
| 10,408,545 B2 | 9/2019 | Blank et al. |
| 10,412,889 B2 | 9/2019 | Palla et al. |
| 10,426,086 B2 | 10/2019 | Van de Wege et al. |
| 10,437,243 B2 | 10/2019 | Blank et al. |
| 10,477,756 B1 | 11/2019 | Richt et al. |
| 10,485,178 B2 | 11/2019 | Mayerle |
| 10,521,526 B2 | 12/2019 | Haaland et al. |
| 10,537,061 B2 | 1/2020 | Farley et al. |
| 10,568,316 B2 | 2/2020 | Gall et al. |
| 10,631,462 B2 | 4/2020 | Bonefas |
| 10,677,637 B1 | 6/2020 | Von Muenster |
| 10,681,872 B2 | 6/2020 | Viaene et al. |
| 10,703,277 B1 | 7/2020 | Schroeder |
| 10,729,067 B2 | 8/2020 | Hammer et al. |
| 10,740,703 B2 | 8/2020 | Story |
| 10,745,868 B2 | 8/2020 | Laugwitz et al. |
| 10,760,946 B2 | 9/2020 | Meier et al. |
| 10,809,118 B1 | 10/2020 | Von Muenster |
| 10,830,634 B2 | 11/2020 | Blank et al. |
| 10,866,109 B2 | 12/2020 | Madsen et al. |
| 10,890,922 B2 | 1/2021 | Ramm et al. |
| 10,909,368 B2 | 2/2021 | Guo et al. |
| 10,912,249 B1 | 2/2021 | Wilson |
| 2002/0011061 A1 | 1/2002 | Lucand et al. |
| 2002/0083695 A1 | 7/2002 | Behnke et al. |
| 2002/0091458 A1 | 7/2002 | Moore |
| 2002/0099471 A1 | 7/2002 | Benneweis |
| 2002/0133309 A1 | 9/2002 | Hardt |
| 2002/0173893 A1 | 11/2002 | Blackmore et al. |
| 2002/0193928 A1 | 12/2002 | Beck |
| 2002/0193929 A1 | 12/2002 | Beck |
| 2002/0198654 A1 | 12/2002 | Lange et al. |
| 2003/0004630 A1 | 1/2003 | Beck |
| 2003/0014171 A1 | 1/2003 | Ma et al. |
| 2003/0015351 A1 | 1/2003 | Goldman et al. |
| 2003/0024450 A1 | 2/2003 | Juptner |
| 2003/0060245 A1 | 3/2003 | Coers et al. |
| 2003/0069680 A1 | 4/2003 | Cohen et al. |
| 2003/0075145 A1 | 4/2003 | Sheidler et al. |
| 2003/0174207 A1 | 9/2003 | Alexia et al. |
| 2003/0182144 A1 | 9/2003 | Pickett et al. |
| 2003/0187560 A1 | 10/2003 | Keller et al. |
| 2003/0216158 A1 | 11/2003 | Bischoff |
| 2003/0229432 A1 | 12/2003 | Ho et al. |
| 2003/0229433 A1 | 12/2003 | van den Berg et al. |
| 2003/0229435 A1 | 12/2003 | Van der Lely |
| 2004/0004544 A1 | 1/2004 | William Knutson |
| 2004/0054457 A1 | 3/2004 | Kormann |
| 2004/0073468 A1 | 4/2004 | Vyas et al. |
| 2004/0193348 A1 | 9/2004 | Gray et al. |
| 2005/0059445 A1 | 3/2005 | Niermann et al. |
| 2005/0066738 A1 | 3/2005 | Moore |
| 2005/0149235 A1 | 7/2005 | Seal et al. |
| 2005/0150202 A1 | 7/2005 | Quick |
| 2005/0197175 A1 | 9/2005 | Anderson |
| 2005/0241285 A1 | 11/2005 | Maertens et al. |
| 2005/0283314 A1 | 12/2005 | Hall |
| 2005/0284119 A1 | 12/2005 | Brunnert |
| 2006/0014489 A1 | 1/2006 | Fitzner et al. |
| 2006/0014643 A1 | 1/2006 | Hacker et al. |
| 2006/0047377 A1 | 3/2006 | Ferguson et al. |
| 2006/0058896 A1 | 3/2006 | Pokorny et al. |
| 2006/0074560 A1 | 4/2006 | Dyer et al. |
| 2006/0155449 A1 | 7/2006 | Dammann |
| 2006/0162631 A1 | 7/2006 | Hickey et al. |
| 2006/0196158 A1 | 9/2006 | Faivre et al. |
| 2006/0200334 A1 | 9/2006 | Faivre et al. |
| 2007/0005209 A1 | 1/2007 | Fitzner et al. |
| 2007/0021948 A1 | 1/2007 | Anderson |
| 2007/0056258 A1 | 3/2007 | Behnke |
| 2007/0068238 A1 | 3/2007 | Wendte |
| 2007/0073700 A1 | 3/2007 | Wippersteg et al. |
| 2007/0089390 A1 | 4/2007 | Hendrickson et al. |
| 2007/0135190 A1 | 6/2007 | Diekhans et al. |
| 2007/0185749 A1 | 8/2007 | Anderson et al. |
| 2007/0199903 A1 | 8/2007 | Denny |
| 2007/0208510 A1 | 9/2007 | Anderson et al. |
| 2007/0233348 A1 | 10/2007 | Diekhans et al. |
| 2007/0233374 A1 | 10/2007 | Diekhans et al. |
| 2007/0239337 A1 | 10/2007 | Anderson |
| 2007/0282523 A1 | 12/2007 | Diekhans et al. |
| 2007/0298744 A1 | 12/2007 | Fitzner et al. |
| 2008/0030320 A1 | 2/2008 | Wilcox et al. |
| 2008/0098035 A1 | 4/2008 | Wippersteg et al. |
| 2008/0140431 A1 | 6/2008 | Anderson et al. |
| 2008/0177449 A1 | 7/2008 | Pickett et al. |
| 2008/0248843 A1 | 10/2008 | Birrell et al. |
| 2008/0268927 A1 | 10/2008 | Farley et al. |
| 2008/0269052 A1 | 10/2008 | Rosinger et al. |
| 2008/0289308 A1 | 11/2008 | Brubaker |
| 2008/0312085 A1 | 12/2008 | Kordes et al. |
| 2009/0044505 A1 | 2/2009 | Huster et al. |
| 2009/0074243 A1 | 3/2009 | Missotten et al. |
| 2009/0143941 A1 | 6/2009 | Tarasinski et al. |
| 2009/0192654 A1 | 7/2009 | Wendte et al. |
| 2009/0216410 A1 | 8/2009 | Allen et al. |
| 2009/0226036 A1 | 9/2009 | Gaal |
| 2009/0259483 A1 | 10/2009 | Hendrickson et al. |
| 2009/0265098 A1 | 10/2009 | Dix |
| 2009/0306835 A1 | 12/2009 | Ellermann et al. |
| 2009/0311084 A1 | 12/2009 | Coers et al. |
| 2009/0312919 A1 | 12/2009 | Foster et al. |
| 2009/0312920 A1 | 12/2009 | Boenig et al. |
| 2009/0325658 A1 | 12/2009 | Phelan et al. |
| 2010/0036696 A1 | 2/2010 | Lang et al. |
| 2010/0042297 A1 | 2/2010 | Foster et al. |
| 2010/0063626 A1 | 3/2010 | Anderson |
| 2010/0063648 A1 | 3/2010 | Anderson |
| 2010/0063651 A1 | 3/2010 | Anderson |
| 2010/0063664 A1 | 3/2010 | Anderson |
| 2010/0063954 A1 | 3/2010 | Anderson |
| 2010/0070145 A1 | 3/2010 | Foster et al. |
| 2010/0071329 A1 | 3/2010 | Hindryckx et al. |
| 2010/0094481 A1 | 4/2010 | Anderson |
| 2010/0121541 A1 | 5/2010 | Behnke et al. |
| 2010/0137373 A1 | 6/2010 | Hungenberg et al. |
| 2010/0145572 A1 | 6/2010 | Steckel et al. |
| 2010/0152270 A1 | 6/2010 | Suty-Heinze et al. |
| 2010/0152943 A1 | 6/2010 | Matthews |
| 2010/0217474 A1 | 8/2010 | Baumgarten et al. |
| 2010/0268562 A1 | 10/2010 | Anderson |
| 2010/0268679 A1 | 10/2010 | Anderson |
| 2010/0285964 A1 | 11/2010 | Waldraff et al. |
| 2010/0317517 A1 | 12/2010 | Rosinger et al. |
| 2010/0319941 A1 | 12/2010 | Peterson |
| 2010/0332051 A1 | 12/2010 | Kormann |
| 2011/0056178 A1 | 3/2011 | Sauerwein et al. |
| 2011/0059782 A1 | 3/2011 | Harrington |
| 2011/0072773 A1 | 3/2011 | Schroeder et al. |
| 2011/0084851 A1 | 4/2011 | Peterson et al. |
| 2011/0086684 A1 | 4/2011 | Luellen et al. |
| 2011/0160961 A1 | 6/2011 | Wollenhaupt et al. |
| 2011/0213531 A1 | 9/2011 | Farley et al. |
| 2011/0224873 A1 | 9/2011 | Reeve et al. |
| 2011/0227745 A1 | 9/2011 | Kikuchi et al. |
| 2011/0257850 A1 | 10/2011 | Reeve et al. |
| 2011/0270494 A1 | 11/2011 | Imhof et al. |
| 2011/0270495 A1 | 11/2011 | Knapp |

(56) References Cited

U.S. PATENT DOCUMENTS

| | | |
|---|---|---|
| 2011/0295460 A1 | 12/2011 | Hunt et al. |
| 2011/0307149 A1 | 12/2011 | Pighi et al. |
| 2012/0004813 A1 | 1/2012 | Baumgarten et al. |
| 2012/0029732 A1 | 2/2012 | Meyer |
| 2012/0087771 A1 | 4/2012 | Wenzel |
| 2012/0096827 A1 | 4/2012 | Chaney et al. |
| 2012/0143642 A1 | 6/2012 | O'Neil |
| 2012/0215378 A1 | 8/2012 | Sprock et al. |
| 2012/0215379 A1 | 8/2012 | Sprock et al. |
| 2012/0253611 A1 | 10/2012 | Zielke et al. |
| 2012/0263560 A1 | 10/2012 | Diekhans et al. |
| 2012/0265412 A1 | 10/2012 | Diekhans et al. |
| 2012/0271489 A1 | 10/2012 | Roberts et al. |
| 2012/0323452 A1 | 12/2012 | Green et al. |
| 2013/0019580 A1 | 1/2013 | Anderson et al. |
| 2013/0022430 A1 | 1/2013 | Anderson et al. |
| 2013/0046419 A1 | 2/2013 | Anderson et al. |
| 2013/0046439 A1 | 2/2013 | Anderson et al. |
| 2013/0046525 A1 | 2/2013 | Ali et al. |
| 2013/0103269 A1 | 4/2013 | Meyer Zu Hellgen et al. |
| 2013/0124239 A1 | 5/2013 | Rosa et al. |
| 2013/0184944 A1 | 7/2013 | Missotten et al. |
| 2013/0197767 A1 | 8/2013 | Lenz |
| 2013/0205733 A1 | 8/2013 | Peters et al. |
| 2013/0210505 A1 | 8/2013 | Bischoff |
| 2013/0231823 A1 | 9/2013 | Wang et al. |
| 2013/0319941 A1 | 12/2013 | Schneider |
| 2013/0325242 A1 | 12/2013 | Cavender-Bares et al. |
| 2013/0332003 A1 | 12/2013 | Murray et al. |
| 2014/0002489 A1 | 1/2014 | Sauder et al. |
| 2014/0019017 A1 | 1/2014 | Wilken et al. |
| 2014/0021598 A1 | 1/2014 | Sutardja |
| 2014/0050364 A1 | 2/2014 | Brueckner et al. |
| 2014/0067745 A1 | 3/2014 | Avey |
| 2014/0121882 A1 | 5/2014 | Gilmore et al. |
| 2014/0129048 A1 | 5/2014 | Baumgarten et al. |
| 2014/0172222 A1 | 6/2014 | Nickel |
| 2014/0172224 A1 | 6/2014 | Matthews et al. |
| 2014/0172225 A1 | 6/2014 | Matthews et al. |
| 2014/0208870 A1 | 7/2014 | Quaderer et al. |
| 2014/0215984 A1 | 8/2014 | Bischoff |
| 2014/0230391 A1 | 8/2014 | Hendrickson et al. |
| 2014/0230392 A1 | 8/2014 | Dybro et al. |
| 2014/0236381 A1 | 8/2014 | Anderson et al. |
| 2014/0236431 A1 | 8/2014 | Hendrickson et al. |
| 2014/0257911 A1 | 9/2014 | Anderson |
| 2014/0262547 A1 | 9/2014 | Acheson et al. |
| 2014/0277960 A1 | 9/2014 | Blank et al. |
| 2014/0297242 A1 | 10/2014 | Sauder et al. |
| 2014/0303814 A1 | 10/2014 | Burema et al. |
| 2014/0324272 A1 | 10/2014 | Madsen et al. |
| 2014/0331631 A1 | 11/2014 | Sauder et al. |
| 2014/0338298 A1 | 11/2014 | Jung et al. |
| 2014/0350802 A1 | 11/2014 | Biggerstaff et al. |
| 2014/0360148 A1 | 12/2014 | Wienker et al. |
| 2015/0049088 A1 | 2/2015 | Snyder et al. |
| 2015/0088785 A1 | 3/2015 | Chi |
| 2015/0095830 A1 | 4/2015 | Massoumi et al. |
| 2015/0101519 A1 | 4/2015 | Blackwell et al. |
| 2015/0105984 A1 | 4/2015 | Birrell et al. |
| 2015/0124054 A1 | 5/2015 | Darr et al. |
| 2015/0168187 A1 | 6/2015 | Myers |
| 2015/0211199 A1 | 7/2015 | Corcoran et al. |
| 2015/0230403 A1 | 8/2015 | Jung et al. |
| 2015/0242799 A1 | 8/2015 | Seki et al. |
| 2015/0243114 A1 | 8/2015 | Tanabe et al. |
| 2015/0254800 A1 | 9/2015 | Johnson et al. |
| 2015/0264863 A1 | 9/2015 | Muench et al. |
| 2015/0276794 A1 | 10/2015 | Pistrol et al. |
| 2015/0278640 A1 | 10/2015 | Johnson et al. |
| 2015/0285647 A1 | 10/2015 | Meyer zu Helligen et al. |
| 2015/0293029 A1 | 10/2015 | Acheson et al. |
| 2015/0302305 A1 | 10/2015 | Rupp et al. |
| 2015/0305238 A1 | 10/2015 | Klausmann et al. |
| 2015/0305239 A1 | 10/2015 | Jung |
| 2015/0327440 A1 | 11/2015 | Dybro et al. |
| 2015/0351320 A1 | 12/2015 | Takahara et al. |
| 2015/0370935 A1 | 12/2015 | Starr |
| 2015/0373902 A1 | 12/2015 | Pasquier |
| 2015/0379785 A1 | 12/2015 | Brown, Jr. et al. |
| 2016/0025531 A1 | 1/2016 | Bischoff et al. |
| 2016/0029558 A1 | 2/2016 | Dybro et al. |
| 2016/0052525 A1 | 2/2016 | Turcer et al. |
| 2016/0057922 A1 | 3/2016 | Freiberg et al. |
| 2016/0066505 A1 | 3/2016 | Bakke et al. |
| 2016/0073573 A1 | 3/2016 | Ethington et al. |
| 2016/0078375 A1 | 3/2016 | Ethington et al. |
| 2016/0078570 A1 | 3/2016 | Ethington et al. |
| 2016/0084813 A1 | 3/2016 | Anderson et al. |
| 2016/0088794 A1 | 3/2016 | Baumgarten et al. |
| 2016/0106038 A1 | 4/2016 | Boyd et al. |
| 2016/0146611 A1 | 5/2016 | Matthews |
| 2016/0202227 A1 | 7/2016 | Mathur et al. |
| 2016/0203657 A1 | 7/2016 | Bell et al. |
| 2016/0212939 A1 | 7/2016 | Ouchida et al. |
| 2016/0215994 A1 | 7/2016 | Mewes et al. |
| 2016/0232621 A1 | 8/2016 | Ethington et al. |
| 2016/0247075 A1 | 8/2016 | Mewes et al. |
| 2016/0247082 A1 | 8/2016 | Stehling |
| 2016/0260021 A1 | 9/2016 | Marek |
| 2016/0286720 A1 | 10/2016 | Heitmann et al. |
| 2016/0286721 A1 | 10/2016 | Heitmann et al. |
| 2016/0286722 A1 | 10/2016 | Heitmann et al. |
| 2016/0309656 A1 | 10/2016 | Wilken et al. |
| 2016/0327535 A1 | 11/2016 | Cotton et al. |
| 2016/0330906 A1 | 11/2016 | Acheson et al. |
| 2016/0338267 A1 | 11/2016 | Anderson et al. |
| 2016/0342915 A1 | 11/2016 | Humphrey |
| 2016/0345485 A1 | 12/2016 | Acheson et al. |
| 2016/0360697 A1 | 12/2016 | Diaz |
| 2017/0013773 A1 | 1/2017 | Kirk et al. |
| 2017/0031365 A1 | 2/2017 | Sugumaran et al. |
| 2017/0034997 A1 | 2/2017 | Mayerle |
| 2017/0049045 A1 | 2/2017 | Wilken et al. |
| 2017/0055433 A1 | 3/2017 | Jamison |
| 2017/0082442 A1 | 3/2017 | Anderson |
| 2017/0083024 A1 | 3/2017 | Reijersen Van Buuren |
| 2017/0086381 A1 | 3/2017 | Roell et al. |
| 2017/0089741 A1 | 3/2017 | Takahashi et al. |
| 2017/0089742 A1 | 3/2017 | Bruns et al. |
| 2017/0090068 A1 | 3/2017 | Xiang et al. |
| 2017/0105331 A1 | 4/2017 | Herlitzius et al. |
| 2017/0105335 A1 | 4/2017 | Xu et al. |
| 2017/0112049 A1 | 4/2017 | Weisberg et al. |
| 2017/0112061 A1 | 4/2017 | Meyer |
| 2017/0115862 A1 | 4/2017 | Stratton et al. |
| 2017/0118915 A1 | 5/2017 | Middelberg et al. |
| 2017/0124463 A1 | 5/2017 | Chen et al. |
| 2017/0127606 A1 | 5/2017 | Horton |
| 2017/0160916 A1 | 6/2017 | Baumgarten et al. |
| 2017/0161627 A1 | 6/2017 | Xu et al. |
| 2017/0185086 A1 | 6/2017 | Sauder et al. |
| 2017/0188515 A1 | 7/2017 | Baumgarten et al. |
| 2017/0192431 A1 | 7/2017 | Foster et al. |
| 2017/0208742 A1 | 7/2017 | Ingibergsson et al. |
| 2017/0213141 A1 | 7/2017 | Xu et al. |
| 2017/0215330 A1 | 8/2017 | Missotten et al. |
| 2017/0223947 A1 | 8/2017 | Gall et al. |
| 2017/0227969 A1 | 8/2017 | Murray et al. |
| 2017/0235471 A1 | 8/2017 | Scholer et al. |
| 2017/0245434 A1 | 8/2017 | Jung et al. |
| 2017/0251600 A1 | 9/2017 | Anderson et al. |
| 2017/0270446 A1 | 9/2017 | Starr et al. |
| 2017/0270616 A1 | 9/2017 | Basso |
| 2017/0316692 A1 | 11/2017 | Rusciolelli et al. |
| 2017/0318743 A1 | 11/2017 | Sauder et al. |
| 2017/0322550 A1 | 11/2017 | Yokoyama |
| 2017/0332551 A1 | 11/2017 | Todd et al. |
| 2017/0336787 A1 | 11/2017 | Pichlmaier et al. |
| 2017/0370765 A1 | 12/2017 | Meier et al. |
| 2018/0000011 A1 | 1/2018 | Schleusner et al. |
| 2018/0014452 A1 | 1/2018 | Starr |
| 2018/0022559 A1 | 1/2018 | Knutson |
| 2018/0024549 A1 | 1/2018 | Hurd |

(56) References Cited

U.S. PATENT DOCUMENTS

| | | |
|---|---|---|
| 2018/0035622 A1 | 2/2018 | Gresch et al. |
| 2018/0054955 A1 | 3/2018 | Oliver |
| 2018/0060975 A1 | 3/2018 | Hassanzadeh |
| 2018/0070534 A1 | 3/2018 | Mayerle |
| 2018/0077865 A1 | 3/2018 | Gallmeier |
| 2018/0084709 A1 | 3/2018 | Wieckhorst et al. |
| 2018/0084722 A1 | 3/2018 | Wieckhorst et al. |
| 2018/0092301 A1 | 4/2018 | Vandike et al. |
| 2018/0092302 A1 | 4/2018 | Vandike et al. |
| 2018/0108123 A1 | 4/2018 | Baurer et al. |
| 2018/0120133 A1 | 5/2018 | Blank et al. |
| 2018/0121821 A1 | 5/2018 | Parsons et al. |
| 2018/0124992 A1 | 5/2018 | Koch et al. |
| 2018/0128933 A1 | 5/2018 | Koch et al. |
| 2018/0129879 A1 | 5/2018 | Achtelik et al. |
| 2018/0132422 A1* | 5/2018 | Hassanzadeh ......... G06Q 50/02 |
| 2018/0136664 A1 | 5/2018 | Tomita et al. |
| 2018/0146612 A1 | 5/2018 | Sauder et al. |
| 2018/0146624 A1 | 5/2018 | Chen et al. |
| 2018/0153084 A1 | 6/2018 | Calleija et al. |
| 2018/0177125 A1 | 6/2018 | Takahara et al. |
| 2018/0181893 A1 | 6/2018 | Basso |
| 2018/0196438 A1 | 7/2018 | Newlin et al. |
| 2018/0196441 A1 | 7/2018 | Muench et al. |
| 2018/0211156 A1 | 7/2018 | Guan et al. |
| 2018/0232674 A1 | 8/2018 | Bilde |
| 2018/0242523 A1 | 8/2018 | Kirchbeck et al. |
| 2018/0249641 A1 | 9/2018 | Lewis et al. |
| 2018/0257657 A1* | 9/2018 | Blank .................. B60W 10/20 |
| 2018/0271015 A1 | 9/2018 | Redden et al. |
| 2018/0279599 A1 | 10/2018 | Struve |
| 2018/0295771 A1 | 10/2018 | Peters |
| 2018/0310474 A1 | 11/2018 | Posselius et al. |
| 2018/0317381 A1 | 11/2018 | Bassett |
| 2018/0317385 A1 | 11/2018 | Wellensiek et al. |
| 2018/0325012 A1 | 11/2018 | Ferrari et al. |
| 2018/0325014 A1 | 11/2018 | Debbaut |
| 2018/0332767 A1 | 11/2018 | Muench et al. |
| 2018/0338422 A1 | 11/2018 | Brubaker |
| 2018/0340845 A1 | 11/2018 | Rhodes et al. |
| 2018/0359917 A1 | 12/2018 | Blank et al. |
| 2018/0359919 A1 | 12/2018 | Blank et al. |
| 2018/0364726 A1 | 12/2018 | Foster et al. |
| 2019/0021226 A1 | 1/2019 | Dima et al. |
| 2019/0025175 A1 | 1/2019 | Laugwitz |
| 2019/0041813 A1 | 2/2019 | Horn et al. |
| 2019/0050948 A1 | 2/2019 | Perry et al. |
| 2019/0057460 A1 | 2/2019 | Sakaguchi et al. |
| 2019/0066234 A1 | 2/2019 | Bedoya et al. |
| 2019/0069470 A1 | 3/2019 | Pfeiffer et al. |
| 2019/0075727 A1 | 3/2019 | Duke et al. |
| 2019/0085785 A1 | 3/2019 | Abolt |
| 2019/0090423 A1 | 3/2019 | Escher et al. |
| 2019/0098825 A1 | 4/2019 | Neitemeier et al. |
| 2019/0104722 A1 | 4/2019 | Slaughter et al. |
| 2019/0108413 A1 | 4/2019 | Chen et al. |
| 2019/0114847 A1 | 4/2019 | Wagner et al. |
| 2019/0124819 A1 | 5/2019 | Madsen et al. |
| 2019/0129430 A1 | 5/2019 | Madsen et al. |
| 2019/0136491 A1 | 5/2019 | Martin |
| 2019/0138962 A1 | 5/2019 | Ehlmann et al. |
| 2019/0147094 A1 | 5/2019 | Zhan et al. |
| 2019/0147249 A1 | 5/2019 | Kiepe et al. |
| 2019/0156255 A1 | 5/2019 | Carroll |
| 2019/0174667 A1 | 6/2019 | Gresch et al. |
| 2019/0183047 A1 | 6/2019 | Dybro et al. |
| 2019/0200522 A1 | 7/2019 | Hansen et al. |
| 2019/0230855 A1 | 8/2019 | Reed et al. |
| 2019/0239416 A1 | 8/2019 | Green et al. |
| 2019/0261550 A1 | 8/2019 | Damme et al. |
| 2019/0261559 A1 | 8/2019 | Heitmann et al. |
| 2019/0261560 A1 | 8/2019 | Jelenkovic |
| 2019/0313570 A1 | 10/2019 | Owechko |
| 2019/0327889 A1 | 10/2019 | Borgstadt |
| 2019/0327892 A1 | 10/2019 | Fries et al. |
| 2019/0335662 A1 | 11/2019 | Good et al. |
| 2019/0335674 A1 | 11/2019 | Basso |
| 2019/0343035 A1 | 11/2019 | Smith et al. |
| 2019/0343043 A1 | 11/2019 | Bormann et al. |
| 2019/0343044 A1 | 11/2019 | Bormann et al. |
| 2019/0343048 A1 | 11/2019 | Farley et al. |
| 2019/0351765 A1 | 11/2019 | Rabusic |
| 2019/0354081 A1 | 11/2019 | Blank et al. |
| 2019/0364733 A1 | 12/2019 | Laugen et al. |
| 2019/0364734 A1 | 12/2019 | Kriebel et al. |
| 2020/0000006 A1 | 1/2020 | McDonald et al. |
| 2020/0008351 A1 | 1/2020 | Zielke et al. |
| 2020/0015416 A1 | 1/2020 | Barther et al. |
| 2020/0019159 A1 | 1/2020 | Kocer et al. |
| 2020/0024102 A1 | 1/2020 | Brill et al. |
| 2020/0029488 A1 | 1/2020 | Bertucci et al. |
| 2020/0034759 A1 | 1/2020 | Dumstorff et al. |
| 2020/0037491 A1 | 2/2020 | Schoeny et al. |
| 2020/0053961 A1 | 2/2020 | Dix et al. |
| 2020/0064144 A1 | 2/2020 | Tomita et al. |
| 2020/0064863 A1 | 2/2020 | Tomita et al. |
| 2020/0074023 A1 | 3/2020 | Nizami et al. |
| 2020/0084963 A1 | 3/2020 | Gururajan et al. |
| 2020/0084966 A1 | 3/2020 | Corban et al. |
| 2020/0090094 A1 | 3/2020 | Blank |
| 2020/0097851 A1 | 3/2020 | Alvarez et al. |
| 2020/0113142 A1 | 4/2020 | Coleman et al. |
| 2020/0125822 A1 | 4/2020 | Yang et al. |
| 2020/0128732 A1 | 4/2020 | Chaney |
| 2020/0128733 A1 | 4/2020 | Vandike et al. |
| 2020/0128734 A1 | 4/2020 | Brammeier et al. |
| 2020/0128735 A1 | 4/2020 | Bonefas et al. |
| 2020/0128737 A1 | 4/2020 | Anderson et al. |
| 2020/0128738 A1 | 4/2020 | Suleman et al. |
| 2020/0128740 A1 | 4/2020 | Suleman |
| 2020/0133262 A1 | 4/2020 | Suleman et al. |
| 2020/0141784 A1 | 5/2020 | Lange et al. |
| 2020/0146203 A1 | 5/2020 | Deng |
| 2020/0150631 A1 | 5/2020 | Frieberg et al. |
| 2020/0154639 A1 | 5/2020 | Takahara et al. |
| 2020/0163277 A1 | 5/2020 | Cooksey et al. |
| 2020/0163292 A1* | 5/2020 | Gerdes ................ A01G 25/092 |
| 2020/0183406 A1 | 6/2020 | Borgstadt |
| 2020/0187409 A1 | 6/2020 | Meyer |
| 2020/0196526 A1 | 6/2020 | Koch et al. |
| 2020/0202596 A1 | 6/2020 | Kitahara et al. |
| 2020/0221632 A1 | 7/2020 | Strnad et al. |
| 2020/0221635 A1 | 7/2020 | Hendrickson et al. |
| 2020/0221636 A1 | 7/2020 | Boydens et al. |
| 2020/0236836 A1* | 7/2020 | Barrick ................ A01B 79/005 |
| 2020/0265527 A1 | 8/2020 | Rose et al. |
| 2020/0278680 A1 | 9/2020 | Schultz et al. |
| 2020/0317114 A1 | 10/2020 | Hoff |
| 2020/0319632 A1 | 10/2020 | Desai et al. |
| 2020/0319655 A1 | 10/2020 | Desai et al. |
| 2020/0323133 A1 | 10/2020 | Anderson et al. |
| 2020/0323134 A1 | 10/2020 | Darr et al. |
| 2020/0326674 A1 | 10/2020 | Palla et al. |
| 2020/0326727 A1 | 10/2020 | Palla et al. |
| 2020/0333278 A1 | 10/2020 | Locken et al. |
| 2020/0337232 A1 | 10/2020 | Blank et al. |
| 2020/0352099 A1 | 11/2020 | Meier et al. |
| 2020/0359547 A1 | 11/2020 | Sakaguchi et al. |
| 2020/0359549 A1 | 11/2020 | Sakaguchi et al. |
| 2020/0363256 A1 | 11/2020 | Meier et al. |
| 2020/0375083 A1 | 12/2020 | Anderson et al. |
| 2020/0375084 A1 | 12/2020 | Sakaguchi et al. |
| 2020/0378088 A1 | 12/2020 | Anderson |
| 2020/0404842 A1 | 12/2020 | Dugas et al. |
| 2021/0015041 A1 | 1/2021 | Bormann et al. |
| 2021/0129853 A1 | 5/2021 | Appleton et al. |
| 2021/0176916 A1 | 6/2021 | Sidon et al. |
| 2021/0176918 A1* | 6/2021 | Franzen ............. A01F 15/0825 |

(56) References Cited

U.S. PATENT DOCUMENTS

2021/0289687 A1 9/2021 Heinold et al.
2021/0321567 A1 10/2021 Sidon et al.

FOREIGN PATENT DOCUMENTS

| | | |
|---|---|---|
| BR | MU6800140 U | 12/1989 |
| BR | PI0502658 A | 2/2007 |
| BR | PI0802384 A2 | 3/2010 |
| BR | PI1100258 A2 | 3/2014 |
| BR | 102014007178 A2 | 8/2016 |
| CA | 1165300 A | 4/1984 |
| CA | 2283767 A1 | 3/2001 |
| CA | 2330979 A1 | 8/2001 |
| CA | 2629555 A1 | 11/2009 |
| CA | 135611 S | 5/2011 |
| CN | 2451633 Y | 10/2001 |
| CN | 101236188 A | 8/2008 |
| CN | 100416590 C | 9/2008 |
| CN | 101303338 A | 11/2008 |
| CN | 101363833 A | 2/2009 |
| CN | 201218789 Y | 4/2009 |
| CN | 101839906 A | 9/2010 |
| CN | 101929166 A | 12/2010 |
| CN | 102080373 A | 6/2011 |
| CN | 102138383 A | 8/2011 |
| CN | 102277867 B | 12/2011 |
| CN | 202110103 U | 1/2012 |
| CN | 202119772 U | 1/2012 |
| CN | 202340435 U | 7/2012 |
| CN | 103088807 A | 5/2013 |
| CN | 103181263 A | 7/2013 |
| CN | 203053961 U | 7/2013 |
| CN | 203055121 U | 7/2013 |
| CN | 203206739 U | 9/2013 |
| CN | 102277867 B | 10/2013 |
| CN | 203275401 U | 11/2013 |
| CN | 103491765 | 1/2014 |
| CN | 203613525 U | 5/2014 |
| CN | 203658201 U | 6/2014 |
| CN | 103954738 A | 7/2014 |
| CN | 203741803 U | 7/2014 |
| CN | 204000818 U | 12/2014 |
| CN | 204435344 U | 7/2015 |
| CN | 204475304 U | 7/2015 |
| CN | 105205248 A | 12/2015 |
| CN | 204989174 U | 1/2016 |
| CN | 105432228 A | 3/2016 |
| CN | 105741180 A | 7/2016 |
| CN | 106053330 A | 10/2016 |
| CN | 106198877 A | 12/2016 |
| CN | 106198879 A | 12/2016 |
| CN | 106226470 A | 12/2016 |
| CN | 106248873 A | 12/2016 |
| CN | 106290800 A | 1/2017 |
| CN | 106327349 A | 1/2017 |
| CN | 106644663 A | 5/2017 |
| CN | 206330815 U | 7/2017 |
| CN | 206515118 U | 9/2017 |
| CN | 206515119 U | 9/2017 |
| CN | 206616118 U | 11/2017 |
| CN | 206696107 | 12/2017 |
| CN | 206696107 U | 12/2017 |
| CN | 107576674 | 1/2018 |
| CN | 107576674 A | 1/2018 |
| CN | 206906093 U | 1/2018 |
| CN | 206941558 | 1/2018 |
| CN | 206941558 U | 1/2018 |
| CN | 107736088 A | 2/2018 |
| CN | 107795095 A | 3/2018 |
| CN | 207079558 | 3/2018 |
| CN | 107941286 A | 4/2018 |
| CN | 107957408 A | 4/2018 |
| CN | 108009542 A | 5/2018 |
| CN | 108304796 A | 7/2018 |
| CN | 207567744 U | 7/2018 |
| CN | 108614089 A | 10/2018 |
| CN | 208013131 U | 10/2018 |
| CN | 108881825 A | 11/2018 |
| CN | 208047351 U | 11/2018 |
| CN | 109357804 A | 2/2019 |
| CN | 109485353 A | 3/2019 |
| CN | 109633127 A | 4/2019 |
| CN | 109763476 A | 5/2019 |
| CN | 109961024 A | 7/2019 |
| CN | 110262287 A | 9/2019 |
| CN | 110720302 A | 1/2020 |
| CN | 111201879 A | 5/2020 |
| CN | 210585958 U | 5/2020 |
| CN | 111406505 A | 7/2020 |
| CS | 247426 B1 | 12/1986 |
| CS | 248318 B1 | 2/1987 |
| CZ | 17266 U1 | 2/2007 |
| CZ | 20252 U1 | 11/2009 |
| DE | 441597 C | 3/1927 |
| DE | 504035 C | 7/1930 |
| DE | 2354828 A1 | 5/1975 |
| DE | 152380 A1 | 11/1981 |
| DE | 3728669 A1 | 3/1989 |
| DE | 4431824 C1 | 5/1996 |
| DE | 19509496 A1 | 9/1996 |
| DE | 19528663 A1 | 2/1997 |
| DE | 19718455 A1 | 11/1997 |
| DE | 19705842 A1 | 8/1998 |
| DE | 19828355 A1 | 1/2000 |
| DE | 10050224 A1 | 4/2002 |
| DE | 10120173 A1 | 10/2002 |
| DE | 202004015141 U1 | 12/2004 |
| DE | 102005000770 B3 | 7/2006 |
| DE | 102005000771 A1 | 8/2006 |
| DE | 102008021785 A1 | 11/2009 |
| DE | 102009041646 A1 | 3/2011 |
| DE | 102010004648 A1 | 7/2011 |
| DE | 102010038661 A1 | 2/2012 |
| DE | 102011005400 A1 | 9/2012 |
| DE | 202012103730 U1 | 10/2012 |
| DE | 102011052688 A1 | 2/2013 |
| DE | 102012211001 A1 | 1/2014 |
| DE | 102012220109 | 5/2014 |
| DE | 102012223768 | 6/2014 |
| DE | 102013212151 A1 | 12/2014 |
| DE | 102013019098 B3 | 1/2015 |
| DE | 102014108449 A1 | 2/2015 |
| DE | 2014201203 A1 | 7/2015 |
| DE | 102014208068 A1 | 10/2015 |
| DE | 102015006398 B3 | 5/2016 |
| DE | 102015109799 A1 | 12/2016 |
| DE | 112015002194 T5 | 1/2017 |
| DE | 102017204511 A1 | 9/2018 |
| DE | 102019206734 A1 | 11/2020 |
| DE | 102019114872 A1 | 12/2020 |
| EP | 0070219 B1 | 10/1984 |
| EP | 0355049 A2 | 2/1990 |
| EP | 845198 B2 | 6/1998 |
| EP | 0532146 B1 | 8/1998 |
| EP | 1444879 A1 | 8/2004 |
| EP | 1219159 B1 | 6/2005 |
| EP | 1219153 B1 | 2/2006 |
| EP | 1692928 A2 | 8/2006 |
| EP | 1574122 B1 | 2/2008 |
| EP | 1943877 A2 | 7/2008 |
| EP | 1598586 B1 | 9/2009 |
| EP | 1731983 B1 | 9/2009 |
| EP | 2146307 A2 | 1/2010 |
| EP | 0845198 B2 | 2/2010 |
| EP | 2186389 A1 | 5/2010 |
| EP | 2267566 A2 | 12/2010 |
| EP | 3491192 A2 | 12/2010 |
| EP | 2057884 B1 | 1/2011 |
| EP | 2146307 B1 | 5/2012 |
| EP | 2446732 A1 | 5/2012 |
| EP | 2524586 A2 | 11/2012 |
| EP | 2529610 A1 | 12/2012 |
| EP | 2243353 B1 | 3/2013 |
| EP | 2174537 B1 | 5/2013 |

(56) References Cited

FOREIGN PATENT DOCUMENTS

| | | |
|---|---|---|
| EP | 2592919 A1 | 5/2013 |
| EP | 1674324 B2 | 5/2014 |
| EP | 2759829 A1 | 7/2014 |
| EP | 2764764 B1 | 8/2014 |
| EP | 2267566 A3 | 12/2014 |
| EP | 2191439 B1 | 3/2015 |
| EP | 2586286 B1 | 3/2015 |
| EP | 2592919 B1 | 9/2015 |
| EP | 2921042 A1 | 9/2015 |
| EP | 2944725 A1 | 11/2015 |
| EP | 2764764 B1 | 12/2015 |
| EP | 2510777 B1 | 3/2016 |
| EP | 2997805 A1 | 3/2016 |
| EP | 3000302 A1 | 3/2016 |
| EP | 2868806 B1 | 7/2016 |
| EP | 3085221 A1 | 10/2016 |
| EP | 3095310 A1 | 11/2016 |
| EP | 3097759 A1 | 11/2016 |
| EP | 2452551 B1 | 5/2017 |
| EP | 3175691 A1 | 6/2017 |
| EP | 3195719 A1 | 7/2017 |
| EP | 3195720 A1 | 7/2017 |
| EP | 3259976 A1 | 12/2017 |
| EP | 3262934 A1 | 1/2018 |
| EP | 3491192 A1 | 1/2018 |
| EP | 3287007 A1 | 2/2018 |
| EP | 3298876 A1 | 3/2018 |
| EP | 3300579 A1 | 4/2018 |
| EP | 3315005 A1 | 5/2018 |
| EP | 3316208 A1 | 5/2018 |
| EP | 2829171 B1 | 6/2018 |
| EP | 2508057 | 7/2018 |
| EP | 2508057 B1 | 7/2018 |
| EP | 3378298 A1 | 9/2018 |
| EP | 3378299 A1 | 9/2018 |
| EP | 2997805 A1 | 10/2018 |
| EP | 3384754 A1 | 10/2018 |
| EP | 3289853 B1 | 3/2019 |
| EP | 3456167 A1 | 3/2019 |
| EP | 3466239 A1 | 4/2019 |
| EP | 3469878 A1 | 4/2019 |
| EP | 3289852 B1 | 6/2019 |
| EP | 3491192 A1 | 6/2019 |
| EP | 3494770 A1 | 6/2019 |
| EP | 3498074 A1 | 6/2019 |
| EP | 3000302 B1 | 8/2019 |
| EP | 3533314 A1 | 9/2019 |
| EP | 3569049 A1 | 11/2019 |
| EP | 3000307 B1 | 12/2019 |
| EP | 3586592 A2 | 1/2020 |
| EP | 3593613 A1 | 1/2020 |
| EP | 3593620 A1 | 1/2020 |
| EP | 3613272 A1 | 2/2020 |
| EP | 3243374 B1 | 3/2020 |
| EP | 3626038 A1 | 3/2020 |
| EP | 3259976 B1 | 4/2020 |
| EP | 3635647 A1 | 4/2020 |
| EP | 3378298 B1 | 5/2020 |
| EP | 3646699 A1 | 5/2020 |
| EP | 3662741 A1 | 6/2020 |
| EP | 3685648 A1 | 7/2020 |
| EP | 2995191 B2 | 10/2020 |
| ES | 2116215 A1 | 7/1998 |
| ES | 2311322 A1 | 2/2009 |
| FI | 5533 A | 11/1913 |
| FR | 1451480 A | 1/1966 |
| FR | 2817344 A1 | 5/2002 |
| FR | 2901291 A | 11/2007 |
| FR | 2901291 A1 | 11/2007 |
| GB | 901081 A | 7/1962 |
| GB | 201519517 A1 | 5/2017 |
| IN | 1632DE2014 A | 8/2016 |
| IN | 01632DE2014 A | 8/2016 |
| IN | 201641027017 A | 10/2016 |
| IN | 202041039250 A | 9/2020 |
| JP | 7079681 A | 11/1982 |
| JP | S60253617 A | 12/1985 |
| JP | S63308110 A | 12/1988 |
| JP | H02196960 A | 8/1990 |
| JP | H02215311 A | 8/1990 |
| JP | H0779681 A | 3/1995 |
| JP | H1066436 A | 3/1998 |
| JP | H10191762 A | 7/1998 |
| JP | 2000352044 | 12/2000 |
| JP | 2001057809 A | 3/2001 |
| JP | 2002186348 A | 7/2002 |
| JP | 2005227233 A | 8/2005 |
| JP | 2006166871 A | 6/2006 |
| JP | 2011205967 A | 10/2011 |
| JP | 2015070812 A | 4/2015 |
| JP | 2015151826 A | 8/2015 |
| JP | 2015219651 A | 12/2015 |
| JP | 2016071726 A | 5/2016 |
| JP | 2016160808 A | 9/2016 |
| JP | 6087258 B2 | 3/2017 |
| JP | 2017136035 A | 8/2017 |
| JP | 2017137729 A | 8/2017 |
| JP | 2017195804 A | 11/2017 |
| JP | 2018068284 A | 5/2018 |
| JP | 2018102154 A | 7/2018 |
| JP | 2018151388 A | 9/2018 |
| JP | 2019004796 A | 1/2019 |
| JP | 2019129744 A | 8/2019 |
| JP | 2019146506 A | 9/2019 |
| JP | 2019216744 A | 12/2019 |
| JP | 2020018255 A | 2/2020 |
| JP | 2020031607 A | 3/2020 |
| JP | 2020113062 A | 7/2020 |
| JP | 2020127405 A | 8/2020 |
| KR | 100974892 | 8/2010 |
| KR | 100974892 B1 | 8/2010 |
| KR | 20110018582 A | 2/2011 |
| KR | 101067576 B | 9/2011 |
| KR | 101067576 B1 | 9/2011 |
| KR | 101134075 B1 | 4/2012 |
| KR | 101447197 B1 | 10/2014 |
| KR | 101653750 | 9/2016 |
| KR | 20170041377 A | 4/2017 |
| KR | 200485051 Y | 11/2017 |
| KR | 200485051 Y1 | 11/2017 |
| KR | 101873657 B | 8/2018 |
| MX | GT06000012 A | 1/2008 |
| PL | 178299 B1 | 4/2000 |
| RO | 130713 | 11/2015 |
| RU | 1791767 C | 1/1993 |
| RU | 2005102554 A | 7/2006 |
| RU | 2421744 C | 6/2011 |
| RU | 2421744 C1 | 6/2011 |
| RU | 2447640 C1 | 4/2012 |
| RU | 2502047 C | 12/2013 |
| RU | 2502047 C1 | 12/2013 |
| RU | 164128 | 8/2016 |
| RU | 2017114139 A | 4/2017 |
| RU | 2017114139 A | 10/2018 |
| RU | 2017114139 A3 | 5/2019 |
| SU | 834514 A1 | 5/1981 |
| SU | 887717 A1 | 12/1981 |
| SU | 1052940 A1 | 11/1983 |
| SU | 1134669 A1 | 1/1985 |
| SU | 1526588 A1 | 12/1989 |
| SU | 1540053 A1 | 1/1991 |
| SU | 1761864 A1 | 9/1992 |
| WO | 1986005353 A1 | 9/1986 |
| WO | 2001052160 A1 | 7/2001 |
| WO | 2002015673 A1 | 2/2002 |
| WO | 2003005803 A1 | 1/2003 |
| WO | 2007050192 A2 | 5/2007 |
| WO | 2009156542 A1 | 12/2009 |
| WO | 2010003421 A1 | 1/2010 |
| WO | 2011104085 A1 | 9/2011 |
| WO | 2012041621 A1 | 4/2012 |
| WO | 2012110508 A1 | 8/2012 |
| WO | 2012110544 A1 | 8/2012 |
| WO | 2013063106 A2 | 5/2013 |

(56) References Cited

FOREIGN PATENT DOCUMENTS

| | | |
|---|---|---|
| WO | 2013079247 A1 | 6/2013 |
| WO | 2013086351 A1 | 6/2013 |
| WO | 2013087275 A1 | 6/2013 |
| WO | 2014046685 A1 | 3/2014 |
| WO | 2014093814 A1 | 6/2014 |
| WO | 2014195302 A1 | 12/2014 |
| WO | 2015038751 A1 | 3/2015 |
| WO | 2015153809 A1 | 10/2015 |
| WO | 16020595 A1 | 2/2016 |
| WO | 2016020595 A1 | 2/2016 |
| WO | 2016118686 A1 | 7/2016 |
| WO | 2017008161 A1 | 1/2017 |
| WO | 2017060168 A1 | 4/2017 |
| WO | 2017077113 A1 | 5/2017 |
| WO | 2017096489 A1 | 6/2017 |
| WO | 2017099570 A1 | 6/2017 |
| WO | 2017116913 A1 | 7/2017 |
| WO | 2017170507 A1 | 10/2017 |
| WO | 2017205406 A1 | 11/2017 |
| WO | 2017205410 A1 | 11/2017 |
| WO | 2018043336 A1 | 3/2018 |
| WO | 2018073060 A1 | 4/2018 |
| WO | 2018081759 A1 | 5/2018 |
| WO | 2018112615 | 6/2018 |
| WO | 2018116772 A1 | 6/2018 |
| WO | 2018142768 A1 | 8/2018 |
| WO | 2018200870 A1 | 11/2018 |
| WO | 2018206587 A1 | 11/2018 |
| WO | 2018220159 A1 | 12/2018 |
| WO | 2018226139 A1 | 12/2018 |
| WO | 2018235486 A1 | 12/2018 |
| WO | 2018235942 A1 | 12/2018 |
| WO | WO18235486 A1 | 12/2018 |
| WO | 2019034213 A1 | 2/2019 |
| WO | 2019079205 A1 | 4/2019 |
| WO | 2019081349 A1 | 5/2019 |
| WO | 2019091535 A1 | 5/2019 |
| WO | 2019109191 A1 | 6/2019 |
| WO | 2019124174 A1 | 6/2019 |
| WO | 2019124217 A1 | 6/2019 |
| WO | 2019124225 A1 | 6/2019 |
| WO | 2019124273 A1 | 6/2019 |
| WO | 2019129333 A1 | 7/2019 |
| WO | 2019129334 A1 | 7/2019 |
| WO | 2019129335 A1 | 7/2019 |
| WO | 2019215185 A1 | 11/2019 |
| WO | 2019230358 A1 | 12/2019 |
| WO | 2020026578 A1 | 2/2020 |
| WO | 2020026650 A1 | 2/2020 |
| WO | 2020026651 A1 | 2/2020 |
| WO | 2020031473 A1 | 2/2020 |
| WO | 2020038810 A1 | 2/2020 |
| WO | 2020039312 A1 | 2/2020 |
| WO | 2020039671 A1 | 2/2020 |
| WO | 2020044726 A1 | 3/2020 |
| WO | 2020082182 A1 | 4/2020 |
| WO | 2020100810 A1 | 5/2020 |
| WO | 2020110920 A1 | 6/2020 |
| WO | 2020195007 A1 | 10/2020 |
| WO | 2020206941 A1 | 10/2020 |
| WO | 2020206942 A1 | 10/2020 |
| WO | 2020210607 A1 | 10/2020 |
| WO | 2020221981 A1 | 11/2020 |
| WO | 2021262500 A1 | 12/2021 |

OTHER PUBLICATIONS

Managing corn harvest this fall with variable corn conditions (https://www.ocj.com/2019/10/managing-corn-harvest-this-fall-with-variable-corn-conditions/), 4 pages, Oct. 10, 2019.
Reducing Aflatoxin in Corn During Harvest and Storage (https://extension.uga.edu/publications/detail.html?number=B1231&title=Reducing%20Aflatoxin%20in%20Corn%20During%20Harvest%20and%20Storage), 9 pages, Published with Full Review on Apr. 19, 2017.
Variable Rate Applications to Optimize Inputs (https://www.cotton.org/tech/physiology/cpt/miscpubs/upload/CPT-v9No2-98-REPOP.pdf), 8 pages, Nov. 2, 1998.
Robin Booker, Video: Canadian cage mill teams up with JD (https://www.producer.com/2019/12/video-canadian-cage-mill-teams-up-with-jd/), 6 pages, Dec. 19, 2019.
Jarnevich, et al. "Forecasting Weed Distributions using Climate Data: A GIS Early Warning Tool", Invasive Plant Science and Management, 11 pages, Jan. 20, 2017.
Burks, "Classification of Weed Species Using Color Texture Features and Discriminant Analysis" (http://citeseerx.ist.psu.edu/viewdoc/download?doi=10.1.1.468.5833&rep=rep1&type=pdf), 8 pages, 2000.
John Deere, https://www.youtube.com/watch?v=1Gq77CfdGl4&list=PL1KGsSJ4CWk4rShNb3-sTMOliL8meHBL5 (last accessed Jul. 14, 2020), Jun. 15, 2020, 5 pages.
Combine Adjustments (http://corn.agronomy.wisc.edu/Management/L036.aspx), 2 pages, Originally written Feb. 1, 2006; last updated Oct. 18, 2018.
Ardekani, "Off- and on-ground GPR techniques for field-scale soil moisture mapping" Jun. 2013, 13 pages.
Does an Adaptive Gearbox Really Learn How You Drive? (https://practicalmotoring.com.au/voices/does-an-adaptive-gearbox-really-learn-how-you-drive/), Oct. 30, 2019, 8 pages.
https://www.researchgate.net/publication/222527694_Energy_Requirement_Model_for_a_Combine_Harvester_Part_I_Development_of_Component_Models, Abstract Only, Jan. 2005.
http://canola.okstate.edu/cropproduction/harvesting, 8 pages, Aug. 2011.
"Tips and Tricks of Harvesting High Moisture Grain", https://www.koenigequipment.com/blog/tips-and-tricks-of-harvesting-highmoisture-grain, 5 pages, last accessed Feb. 11, 2021.
Hoff, Combine Adjustements, Mar. 1943, 8 pages.
Haung et al., "Accurate Weed Mapping and Prescription Map Generation Based onFully Convolutional Networks Using UAV Imagery", 14 pages, Oct. 1, 2018.
Thompson, "Morning glory can make it impossible to harvest corn", Feb. 19, 2015, 4 pages.
Apan et al., "Predictive Mapping of Blackberry in the Condamine Catchment Using Logistic Regressiona dn Spatial Analysis", Jan. 2008, 12 pages.
Robson, "Remote Sensing Applications for the Determination of Yield, Maturity and Aflatoxin Contamination in Peanut", Oct. 2007, 275 pages.
Bhattarai et al., "Remote Sensing Data to Detect Hessian Fly Infestation in Commercial Wheat Fields", Apr. 16, 2019, 8 pages.
Towery, et al., "Remote Sensing of Crop Hail Damage", Jul. 21, 1975, 31 pages.
Sa et al., "WeedMap: A Large-Scale Semantic Weed Mapping Framework Using Aerial Multispectral Imaging and Deep Neural Network for Precision Farming", Sep. 7, 2018, 25 pages.
Mathyam et al., "Remote Sensing of Biotic Stress in Crop Plants and Its Applications for Pest Management", Dec. 2011, 30 pages.
Martinez-Feria et al., "Evaluating Maize and Soybean Grain Dry-Down In The Field With Predictive Algorithms and Genotype-by-Environmental Analysis", May 9, 2019, 13 pages.
"GIS Maps for Agriculture", Precision Agricultural Mapping, Retrieved Dec. 11, 2020, 6 pages.
Paul, "Scabby Wheat Grain? Increasing Your Fan Speed May Help", https://agcrops.osu.edu/newsletter/corn-newsletter/2015-20/scabby-wheat-grain-increasing-yourfan-speed-may-help, C.O.R.N Newsletter//2015-20, 3 pages.
Clay et al., "Scouting for Weeds", SSMG-15, 4 pages, 2002.
Taylor et al., "Sensor-Based Variable Rate Application for Cotton", 8 pages, 2010.
Christiansen et al., "Designing and Testing a UAV Mapping System for Agricultural Field Surveying", Nov. 23, 2017, 19 pages.
Haung et al., "AccurateWeed Mapping and Prescription Map Generation Based on Fully Convolutional Networks Using UAV Imagery", Oct. 1, 2018, 12 pages.
Morrison, "Should You Use Tillage to Control Resistant Weeds", Aug. 29, 2014, 9 pages.

(56) References Cited

OTHER PUBLICATIONS

Morrison, "Snow Trapping Snars Water", Oct. 13, 2005, 3 pages.
"Soil Zone Index", https://www.satimagingcorp.com/applications/natural-resources/agricultu . . . , Retrieved Dec. 11, 2020, 5 pages.
Malvic, "Soybean Cyst Nematode", University of Minnesota Extension, Oct. 19, 2020, 3 pages.
Unglesbee, "Soybean Pod Shatter—Bad Enough to Scout Before Harvest?—DTN", Oct. 17, 2018, 4 pages.
Tao, "Standing Crop Residue Can Reduce Snow Drifting and Increase Soil Moisture", 2 pages, last accessed Jul. 14, 2020.
Berglund, et al., "Swathing and Harvesting Canola", Jul. 2019, 8 pages.
Bell et al., "Synthetic Aperture Radar and Optical Remote Sensing of Crop Damage Attributed to Severe Weather in the Central United States", Jul. 25, 2018, 1 page.
Rosencrance, "Tabletop Grapes in India to Be Picked by Virginia Tech Robots", Jul. 23, 2020, 8 pages.
Lofton, et al., The Potential of Grazing Grain Sorghum Residue Following Harvest, May 13, 2020, 11 pages.
Beal et al., "Time Shift Evaluation to Improve Yield Map Quality", Published in Applied Engineering in Agriculture vol. 17(3): 385-390 (© 2001 American Society of Agricultural Engineers ), 9 pages.
"Tips and Tricks of Harvesting High Moisture Grain", https://www.koenigequipment.com/blog/tips-and-tricks-of-harvesting-highmoisture-grain, 7 pages, last accessed Jul. 14, 2020.
Ransom, "Tips for Planting Winter Wheat and Winter Rye (for Grain) (Aug. 15, 2019)", 2017, 3 pages.
AgroWatch Tree Grading Maps, "The Grading Maps and Plant Count Reports", https://www.satimagingcorp.com/applications/natural-resources/agricultu . . . , Retrieved Dec. 11, 2020, 4 pages.
Ackley, "Troubleshooting Abnormal Corn Ears", Jul. 23, 2020, 25 pages.
Smith, "Understanding Ear Flex", Feb. 25, 2019, 17 pages.
Carroll et al., "Use of Spectral Vegetation Indicies Derived from Airborne Hyperspectral Imagery For Detection of European Corn Borer Infestation in Iowa Corn Plots", Nov. 2008, 11 pages.
Agriculture, "Using drones in agriculture and capturing actionable data", Retrieved Dec. 11, 2020, 18 pages.
Bentley et al., "Using Landsat to Identify Thunderstorm Damage in Agricultural Regions", Aug. 28, 2001, 14 pages.
Duane Grant and the Idaho Wheat Commission, "Using Remote Sensing to Manage Wheat Grain Protein", Jan. 2, 2003, 13 pages.
Zhang et al., "Using satellite multispectral imagery for damage mapping of armyworm (*Spodoptera frugiperda*) in maize at a regional scale", Apr. 10, 2015, 14 pages.
Booker, "Video: Canadian cage mill teams up with JD", Dec. 19, 2019, 6 pages.
AgTalk Home, "Best Combine to Handle Weeds", Posted Nov. 23, 2018, 9 pages.
"Volunteer corn can be costly for soybeans", Jun. 2, 2016, 1 page.
Pflanz, et al., "Weed Mapping with UAS Imagery and a Bag of Visual Words Based Image Classifier", Published Sep. 24, 2018, 17 pages.
Hartzler, "Weed seed predation in agricultural fields", 9 pages, 2009.
Sa et al., "Weedmap: A Large-Scale Sematnic Weed Mapping Framework Using Aerial Multispectral Imaging and Deep Neural Netowrk for Precision Farming", Sep. 6, 2018, 25 pages.
Nagelkirk, Michigan State University—Extension, "Wheat Harvest: Minimizing the Risk of Fusarium Head Scab Losses", Jul. 11, 2013, 4 pages.
Saskatchewan, "Wheat: Winter Wheat", (https://www.saskatchewan.ca/business/agriculture-natural-resources-and-industry/agribusiness-farmers-and-ranchers/crops-and-irrigation/field-crops/cereals-barley-wheat-oats-triticale/wheat-winter-wheat) 5 pages, last accessed Jul. 14, 2020.
Quora, "Why would I ever use sport mode in my automatic transmission car? Will this incrase fuel efficiency or isit simply a feature that makes form more fun when driving?", Aug. 10, 2020, 5 pages.

Wade, "Using a Drone's Surface Model to Estimate Crop Yields & Assess Plant Health", Oct. 19, 2015, 14 pages.
Mathyam et al., "Remote Sensing of Biotic Stress in Crop Plants and Its Applications for Pest Stress", Dec. 2011, 30 pages.
"Four Helpful Weed-Management Tips for Harvest Time", 2 pages, Sep. 4, 2019.
Franz et al., "The role of topography, soil, and remotely sensed vegetation condition towards predicting crop yield", University of Nebraska—Lincoln, Mar. 23, 2020, 44 pages.
Peiffer et al., The Genetic Architecture of Maize Stalk Strength:, Jun. 20, 2013, 14 pages.
Application and Drawings for U.S. Appl. No. 16/171,978, filed Oct. 26, 2018, 53 pages.
Notice of Allowance for U.S. Appl. No. 16/432,557 dated Mar. 22, 2021, 9 pages.
Zhao, L., Yang, J., Li, P. and Zhang, L., 2014. Characteristics analysis and classification of crop harvest patterns by exploiting high-frequency multipolarization SAR data. IEEE Journal of Selected Topics in Applied Earth Observations and Remote Sensing, 7(9), pp. 3773-3783.
Feng-jie, X., Er-da, W. and Feng-yuan, X., Crop area yield risk evaluation and premium rates calculation—Based on nonparametric kernel density estimation. In 2009 International Conference on Management Science and Engineering, 7 pages.
Liu, R. and Bai, X., May 2014, Random fuzzy production and distribution plan of agricultural products and its PSO algorithm. In 2014 IEEE International Conference on Progress in Informatics and Computing (pp. 32-36). IEEE.
Notice of Allowance for U.S. Appl. No. 16/171,978 dated Mar. 31, 2021, 6 pages.
Application and Drawings for U.S. Appl. No. 17/067,383, filed Oct. 9, 2020, 61 pages.
Martin et al., "Breakage Susceptibility and Harness of Corn Kernels of Various Sizes and Shapes", May 1987, 10 pages.
Jones et al., "Brief history of agricultural systems modeling" Jun. 21, 2016, 15 pages.
Dan Anderson, "Brief history of agricultural systems modeling" 1 pages. Aug. 13, 2019.
A.Y. Şeflek, "Determining the Physico-Mechanical Characteristics of Maize Stalks ForDesigning Harvester", The Journal of Animal & Plant Sciences, 27(3): 2017, p. 855-860 ISSN: 1018-7081, Jun. 1, 2017.
Carmody, Paul, "Windrowing and harvesting", 8 pages Date: Feb. 3, 2010.
Dabney, et al., "Forage Harvest Representation in RUSLE2", Published Nov. 15, 2013, 17 pages.
John Deere S-Series Combines S760, S770, S780, S790 Brochure, 44 pages, Nov. 15, 2017.
Sekhon et al., "Stalk Bending Strength is Strongly Assoicated with Maize Stalk Lodging Incidence Across Multiple Environments", Jun. 20, 2019, 23 pages.
Thomison et al. "Abnormal Corn Ears", Apr. 28, 2015, 1 page.
Anderson, "Adjust your Combine to Reduce Damage to High Moisture Corn", Aug. 13, 2019, 11 pages.
Sumner et al., "Reducing Aflatoxin in Corn During Harvest and Storage", Reviewed by John Worley, Apr. 2017, 6 pages.
Sick, "Better understanding corn hybrid characteristics and properties can impact your seed decisions", 8 pages, Sep. 21, 2018.
TraCI/Change Vehicle State—SUMO Documentation, 10 pages, Retrieved Dec. 11, 2020.
Arnold, et al., Chapter 8. "Plant Growth Component", Jul. 1995, 41 pages.
Humburg, Chapter: 37 "Combine Adjustments to Reduce Harvest Losses", 2019, South Dakota Board of Regents, 8 pages.
Hoff, "Combine Adjustments", Cornell Extension Bulletin 591, Mar. 1943, 10 pages.
University of Wisconsin, Corn Agronomy, Originally written Feb. 1, 2006 | Last updated Oct. 18, 2018, 2 pages.
University of Nebraska-Lincoln, "Combine Adjustments for Downed Corn—Crop Watch", Oct. 27, 2017, 5 pages.
"Combine Cleaning: Quick Guide To Removing Resistant Weed Seeds (Among Other Things)", Nov. 2006, 5 pages.
Dekalb, "Corn Drydown Rates", 7 pages, Aug. 4, 2020.

(56) References Cited

OTHER PUBLICATIONS

Mahmoud et al. Iowa State University, "Corn Ear Orientation Effects on Mechanical Damage and Forces on Concave", 1975, 6 pages.
Sindelar et al., Kansas State University, "Corn Growth & Development" Jul. 17, 2017, 9 pages.
Pannar, "Manage the Growth Stages of the Maize Plant With Pannar", Nov. 14, 2016, 7 pages.
He et al., "Crop residue harvest impacts wind erodibility and simulated soil loss in the Central Great Plains", Sep. 27, 2017, 14 pages.
Blanken, "Designing a Living Snow Fence for Snow Drift Control", Jan. 17, 2018, 9 pages.
Jean, "Drones give aerial boost to ag producers", Mar. 21, 2019, 4 pages.
Zhao et al., "Dynamics modeling for sugarcane sucrose estimation using time series satellite imagery", Jul. 27, 2017, 11 pages.
Brady, "Effects of Cropland Conservation Practices on Fish and Wildlife Habitat", Sep. 1, 2007, 15 pages.
Jasa, et al., "Equipment Adjustments for Harvesting Soybeans at 13%-15% Moisture", Sep. 15, 2017, 2 pages.
Bendig et al., "Estimating Biomass of Barley Using Crop Surface Models (CSMs) Derived from UAV-Based RGB Imaging", Oct. 21, 2014, 18 pages.
Robertson, et al., "Maize Stalk Lodging: Morphological Determinants of Stalk Strength", Mar. 3, 2017, 10 pages.
MacGowan et al. Purdue University, Corn and Soybean Crop Depredation by Wildlife, Jun. 2006, 14 pages.
Martinez-Feria et al., Iowa State University, "Corn Grain Dry Down in Field From Maturity to Harvest", Sep. 20, 2017, 3 pages.
Wrona, "Precision Agriculture's Value" Cotton Physiology Today, vol. 9, No. 2, 1998, 8 pages.
Zhang et al., "Design of an Optical Weed Sensor Using Plant Spectral Characteristics" Sep. 2000, 12 pages.
Hunt, et al., "What Weeds Can Be Remotely Sensed?", 5 pages, May 2016.
Pepper, "Does An Adaptive Gearbox Really Learn How You Drive?", Oct. 30, 2019, 8 pages.
Eggerl, "Optimization of Combine Processes Using Expert Knowledge and Methods of Artificial Intelligence", Oct. 7, 1982, 143 pages.
Sheely et al., "Image-Based, Variable Rate Plant Growth Regulator Application in Cotton at Sheely Farms in California", Jan. 6-10, 2003 Beltwide Cotton Conferences, Nashville, TN, 17 pages.
Kovacs et al., "Physical characteristics and mechanical behaviour of maize stalks for machine development", Apr. 23, 2019, 1-pages.
Anonymously, "Optimizing Crop Profit Across Multiple Grain Attributes and Stover", ip.com, May 26, 2009, 17 pages.
Breen, "Plant Identification: Examining Leaves", Oregon State University, 2020, 8 pages.
Caglayan et al., A Plant Recognition Approach Using Shape and Color Features in Leaf Images, Sep. 2013, 11 pages.
Casady et al., "Precision Agriculture" Yield Monitors University of Missouri-System, 4 pages, 1998.
Apan et al., "Predicting Grain Protein Content in Wheat Using Hyperspectral Sensing of In-season Crop Canopies and Partial Least Squares Regression" 18 pages, 2006.
Xu et al., "Prediction of Wheat Grain Protein by Coupling Multisource Remote Sensing Imagery and ECMWF Data", Apr. 24, 2020, 21 pages.
Day, "Probability Distributions of Field Crop Yields," American Journal of Agricultural Economics, vol. 47, Issue 3, Aug. 1965, Abstract Only, 1 page.
Butzen, "Reducing Harvest Losses in Soybeans", Pioneer, Jul. 23, 2020, 3 pages.
Martin et al., "Relationship between secondary variables and soybean oil and protein concentration", Abstract Only, 1 page., 2007.
Torres, "Precision Planting of Maize" Dec. 2012, 123 pages.

Prosecution History for U.S. Appl. No. 16/380,691 including: Notice of Allowance dated Mar. 10, 2021 and Application and Drawings filed Apr. 10, 2019, 46 pages.
U.S. Appl. No. 16/831,216 Application and Drawings filed Mar. 26, 2020, 56 pages.
Notice of Allowance for U.S. Appl. No. 16/380,531 dated Apr. 5, 2021, 5 pages.
Martin et al. Breakage Susceptibiltiy and Hardness of Corn Kernels of Various Sizes and Shapes, vol. 3( ): May 1087, 10 pages. https://pdfs.semanticscholar.org/e579/1b5363b6a78efd44adfb97755a0cdd14f7ca.pdf.
Hoff, "Combine Adjustments" (https://smallfarmersjournal.com/combine-adjustments/), Mar. 1943. 9 pages.
Optimizing Crop Profit Across Multiple Grain Attributes and Stover, Electronic Publication Date May 26, 2009, 17 pages.
Unglesbee, Soybean Pod Shatter—Bad Enough to Scout Before Harvest—DTN, Oct. 17, 2018, 11 pages. Susceptibility to shatter (https://agfax.com/2018/10/17/soybean-pod-shatter-bad-enough-to-scout-before-harvest-dtn/).
GIS Maps for Agricultural, accessed on May 10, 2022, 7 pages. https://www.satimagingcorp.com/services/geographic-information-systems/gis-maps-agriculture-mapping.
https://wingtra.com/drone-mapping-applications/use-of-drones-in-agriculture, accessed on May 10, 2022, 19 pages.
Energy Requirement Model for a Combine Harvester: Part 1: Development of Component Models, Published online Dec. 22, 2004, 17 pages.
Energy Requirement Model for a Combine Harvester, Part 2: Integration of Component Models, Published online Jan. 18, 2005, 11 pages.
Pioneer on reducing soybean harvest losses including combine adjustments (last accessed Jul. 23, 2020) (https://www.pioneer.com/us/agronomy/reducing_harvest_losses_in_soybeans.html), 5 pages.
Application and Drawings for U.S. Appl. No. 16/175,993, filed Oct. 31, 2018, 28 pages.
Application and Drawings for U.S. Appl. No. 16/380,623, filed Apr. 10, 2019, 36 pages.
Application and Drawings for U.S. Appl. No. 16/783,511, filed Feb. 6, 2020, 55 pages.
"Automated Weed Detection With Drones" dated May 25, 2017, retrieved at: <<https://www.precisionhawk.com/blog/media/topic/automated-weed-identification-with-drones>>, retrieved on Jan. 21, 2020, 4 pages.
F. Forcella, "Estimating the Timing of Weed Emergence", Site-Specific Management Guidelines, retrieved at: <<http://www.ipni.net/publication/ssmg.nsf/0/D26EC9A906F9B8C9852579E500773936/$FILE/SSMG-20.pdf>>, retrieved on Jan. 21, 2020, 4 pages.
Chauhan et al., "Emerging Challenges and Opportunities for Education and Research in Weed Science", frontiers in Plant Science. Published online Sep. 5, 2017, 22 pages.
Apan, A., Wells ,N., Reardon-Smith, K, Richardson, L, McDougall, K, and Basnet, B.B., 2008. Predictive mapping of blackberry in the Condamine Catchment using logistic regression and spatial analysis. In Proceedings of the 2008 Queensland Spatial Conference: Global Warning: What's Happening in Paradise. Spatial Sciences Institute, 11 pages.
Jarnevich, C.S., Holcombe, T.R., Barnett, D.T., Stohlgren, T.J. and Kartesz, J.T., 2010. Forecasting weed distributions using climate data: a GIS early warning tool. Invasive Plant Science and Management. 3(4), pp. 365-375.
Sa et al., "WeedMap: A Large-Scale Semantic Weed Mapping Framework Using Aerial Multispectral Imaging and Deep Neural Network for Precision Farming", Sep. 6, 2018, 25 pages.
Pflanz et al., "Weed Mapping with UAS Imagery and a Bag of Visual Words Based Image Classifier", Published Sep. 24, 2018, 28 pages.
Provisional Application and Drawings for U.S. Appl. No. 62/928,964, filed Oct. 31, 2019, 14 pages.
Application and Drawings for U.S. Appl. No. 16/783,475, filed Feb. 6, 2020, 55 pages.
U.S. Appl. No. 17/067,483 Application and Drawings filed Oct. 9, 2020, 63 pages.

(56) References Cited

OTHER PUBLICATIONS

U.S. Appl. No. 17/066,442 Application and Drawings filed Oct. 8, 2020, 65 pages.
U.S. Appl. No. 16/380,550, filed Apr. 10, 2019, Application and Drawings, 47 pages.
U.S. Appl. No. 17/066,999 Application and Drawings filed Oct. 9, 2020, 67 pages.
U.S. Appl. No. 17/066,444 Application and Drawings filed Oct. 8, 2020, 102 pages.
Extended Search Report for European Patent Application No. 20167930.5 dated Sep. 15, 2020, 8 pages.
Extended Search Report for European Patent Application No. 19205901.2 dated Mar. 17, 2020, 6 pages.
Notice of Allowance for U.S. Appl. No. 16/171,978, dated Dec. 15, 2020, 21 pages.
Zhigen et al., "Research of the Combine Harvester Load Feedback Control System Using Multi-Signal Fusion Method and Fuzzy Algorithm," 2010, Publisher: IEEE, 5 pages.
Dan et al., "On-the-go Throughput Prediction in a Combine Harvester Using Sensor Fusion," 2017, Publisher: IEEE, 6 pages.
Fernandez-Quintanilla et al., "Is the current state of the art of weed monitoring sutible for site-specific weed management in arable crops?", First Published May 1, 2018, 4 pages.
Dionysis Bochtis et al. "Field Operations Planning for Agricultural Vehicles: A Hierarchical Modeling Framework." Agricultural Engineering International: the CIGR Ejournal. Manuscript PM 06 021. vol. IX. Feb. 2007, pp. 1-11.
U.S. Appl. No. 16/432,557, filed Jun. 5, 2019, 61 pages.
European Search Report issued in counterpart European Patent Application No. 19205142.3 dated Feb. 28, 2020 (6 pages).
Mei-Ju et al., "Two paradigms in cellular Internet-of-Things access for energy-harvesting machine-to-machine devices: push-based versus pull-based," 2016, vol. 6, 9 pages.
Yi et al., "An Efficient MAC Protocol With Adaptive Energy Harvesting for Machine-to-Machine Networks," 2015, vol. 3, Publisher: IEEE, 10 pages.
European Search Report issued in European Patent Application No. 19203883.4 dated Mar. 23, 2020 (10 pages).
Notice of Allowance for U.S. Appl. No. 16/171,978 dated Oct. 28, 2020, 5 pages.
Notice of Allowance for U.S. Appl. No. 16/171,978, dated Aug. 7, 2020, 9 pages.
K.R. Manjunath et al., "Developing Spectral Library of Major Plant Species of Western Himalayas Using Ground Observations", J. Indian Soc Remote Sen (Mar. 2014) 42(a):201-216, 17 pages.
U.S. Appl. No. 16/380,564 Application and Drawings filed Apr. 10, 2019, 55 pages.
S. Veenadhari et al., "Machine Learning Approach For Forecasting Crop Yield Based on Climatic Parameters", 2014 International Conference on Computer Communication and Informatics (ICCCI-2014) Jan. 3-6, 2014, Coimbatore, India, 5 pages.
Non-Final Office Action for U.S. Appl. No. 16/380,531 dated Oct. 21, 2020, 10 pages.
U.S. Appl. No. 16/380,531 Application and Drawings filed Apr. 10, 2019, 46 pages.
Extended European Search Report and Written Opinion issued in European Patent Application No. 20208171.7, dated May 11, 2021, in 05 pages.
Cordoba, M.A., Bruno, C.I. Costa, J.L. Peralta, N.R. and Balzarini, M.G., 2016, Protocol for multivariate homegeneous zone delineation in precision agriculture, biosystems engineering, 143, pp. 95-107.
Pioneer Estimator, "Corn Yield Estimator" accessed on Feb. 13, 2018, 1 page. retrieved from: https://www.pioneer.com/home/site/us/tools-apps/growing-tools/corn-yield-estimator/.
Guindin, N. "Estimating Maize Grain Yield From Crop Biophysical Parameters Using Remote Sensing", Nov. 4, 2013, 19 pages.
EP Application No. 19203883.4-1004 Office Action dated May 3, 2021, 4 pages.

Iowa State University Extension and Outreach, "Harvest Weed Seed Control", Dec. 13, 2018, 6 pages. https://crops.extension.iastate.edu/blog/bob-hartzler/harvest-weed-seed-control.
Getting Rid Of WeedsThrough Integrated Weed Management, accessed on Jun. 25, 2021, 10 pages. https://integratedweedmanagement.org/index.php/iwm-toolbox/the-harrington-seed-destructor.
The Importance of Reducing Weed Seeds, Jul. 2018, 2 pages. https://www.aphis.usda.gov/plant_health/soybeans/soybean-handouts.pdf.
Alternative Crop Guide, Published by the Jefferson Institute, "Buckwheat", Revised Jul. 2002. 4 pages.
Lamsal et al. "Sugarcane Harvest Logistics in Brazil" Iowa Research Online, Sep. 11, 2013, 27 pages.
Jensen, "Algorithms for Operational Planning of Agricultural Field Operations", Mechanical Engineering Technical Report ME-TR-3, Nov. 9, 2012, 23 pages.
Chauhan, "Remote Sensing of Crop Lodging", Nov. 16, 2020, 16 pages.
Leu et al., Grazing Corn Residue Using Resources and Reducing Costs, Aug. 2009, 4 pages.
"No-Till Soils", Soil Heath Brochure, 2 pages, last accessed Jul. 14, 2020.
Strickland et al., "Nitrate Toxicity in Livestock" Oklahoma State University, Feb. 2017, 2 pages.
Strickland et al., "Nitrate Toxicity in Livestock" Oklahoma State University, 8 pages, Feb. 2017.
Brownlee, "Neural Networks are Function Approximation Algorithms", Mar. 18, 2020, 13 pages.
Thompson, "Morning glory can make it impossible to harvest corn", Feb. 19, 2015, 3 pages.
Tumlison, "Monitoring Growth Development and Yield Estimation of Maize Using Very High-Resolution UAVImages in Gronau, Germany", Feb. 2017, 63 pages.
Hunt, "Mapping Weed Infestations Using Remote Sensing", 8 pages, Jul. 19, 2005.
Wright, et al., "Managing Grain Protein in Wheat Using Remote Sensing", 12 pages, 2003.
"Malting Barley in Pennsylvania", Agronomy Facts 77, 6 pages, Code EE0179 06/16.
"Green stem syndrome in soybeans" Agronomy eUpdate Issue 478 Oct. 10, 2014, 3 pages.
"Keep Weed Seed Out of Your Harvest", Aug. 8, 2019, 1 pages.
Hodrius et al., "The Impact of Multi-Sensor Data Assimilation on Plant Parameter Retrieval and Yield Estimation for Sugar Beet", The International Archives of the Photogrammetry, Remote Sensing and Spatial Information Sciences, vol. XL-7/W3, 2015, 36th International Symposium on Remote Sensing of Environment, May 11-15, 2015, Berlin, Germany, 7 pages.
Fernandez-Quintanilla et al., "Is the current state of the art of weed monitoring suitable for site-specific weed management in arable crops?", Feb. 2018, 35 pages.
Anonymously, "Improved System and Method for Controlling Agricultural Vehicle Operation Using Historical Data", Dec. 16, 2009, 8 pages.
Anonymously, "System and Method for Controlling Agricultural Vehicle Operation Using Historical Data", Jun. 30, 2009, 8 pages.
"Leafsnap, a new mobile app that identifies plants by leaf shape, is launched by Smithsonian and collaborators", May 2, 2011, 5 pages.
Insect Gallery, Department of Entomology, Kansas State University, Oct. 19, 2020, 8 pages.
Licht, "Influence of Corn Seeding Rate, Soil Attributes, and Topographic Characteristics on Grain Yield, Yield Components, and Grain Composition", 2015, 107 pages,.
"Notice of Retraction Virtual simulation of plant with individual stem based on crop growth model", Mar. 5, 2017, 7 pages.
Ma et al., "Identification of Fusarium Head Blight in Winter Wheat Ears Using Continuous Wavelet Analysis", Dec. 19, 2019, 15 pages.
Leland, "Who Did that? Identifying Insect Damage", Apr. 1, 2015, 4 pages.
"How to improve maize protein content" https://www.yara.co.uk/crop-nutrition/forage-maize/improving-maize-protein-content, Sep. 30, 2020, 10 pages.

(56) References Cited

OTHER PUBLICATIONS

Hafemeister, "Weed control at harvest, combines are ideal vehicles for spreading weed seeds", Sep. 25, 2019, 3 pages.
"Harvesting Tips", Northern Pulse Growers Association, 9 pages, Jan. 31, 2001.
Wortmann et al., "Harvesting Crop Residues", Aug. 10, 2020, 8 pages.
"Harvesting", Oklahoma State University, Canola Swathing Guide, 2010, 9 pages, last accessed Jul. 14, 2020.
Hanna, "Harvest Tips for Lodged Corn", Sep. 6, 2011, 3 pages.
"Green Weeds Complicate Harvest", Crops, Slider, Sep. 26, 2012, 2 pages.
"Agrowatch Green Vegetation Index", Retrieved Dec. 11, 2020, 4 pages.
"Grazing Corn Residues" (http://www.ca.uky.edu), 3 pages, Aug. 24, 2009.
Jarnevich et al., Forecasting Weed Distributions Using Climate Data: A GIS Early Warning Tool, Downloaded on Jul. 13, 2020, 12 pages.
Combine Cutting and Feeding Mechanisms in the Southeast, By J-K Park, Agricultural Research Service, U.S. Dept. of Agriculture, 1963, 1 page.
Hartzler, "Fate of weed seeds in the soil", 4 pages, Jan. 31, 2001.
Digman, "Combine Considerations for a Wet Corn Harvest", Extension SpecialistUW—Madison, 3 pages, Oct. 29, 2009.
S-Series Combine and Front End Equipment Optimization, John Deere Harvester Works, 20 pages Date: Oct. 9, 2017.
Determining yield monitoring system delay time with geostatistical and data segmentation approaches (https://www.ars.usda.gov/ARSUserFiles/50701000/cswq-0036-128359.pdf) Jul. 2002, 13 pages.
Precision Agriculture: Yield Monitors (dated Nov. 1998—metadata; last accessed Jul. 16, 2020) (https://extensiondata.missouri.edu/pub/pdf/envqual/wq0451.pdf) 4 pages.
Paul et al., "Effect of soil water status and strength on trafficability" (1979) (https://www.nrcresearchpress.com/doi/pdfplus/10.4141/cjss79-035), 12 pages, Apr. 23, 1979.
Sick, "Better understanding corn hybrid characteristics and properties can impact your seed decisions" (https://emergence.fbn.com/agronomy/corn-hybrid-characteristics-and-properties-impact-seed-decisions) By Steve Sick, FBN Breeding Project Lead | Sep. 21, 2018, 8 pages.
Robertson et al., "Maize Stalk Lodging: Morphological Determinants of Stalk Strength" Mar. 2017, 10 pages.
Martin, et al., "Breakage Susceptibility and Hardness of Corn Kernels of Various Sizes and Shapes", May 1987, 10 Pages.

\* cited by examiner

PREDICTIVE BIOMASS MAP GENERATION AND CONTROL

FIELD OF THE DESCRIPTION

The present description relates to agricultural machines, forestry machines, construction machines, and turf management machines.

BACKGROUND

There are a wide variety of different types of agricultural machines. Some agricultural machines include harvesters, such as combine harvesters, sugar cane harvesters, cotton harvesters, self-propelled forage harvesters, and windrowers. Some harvesters can also be fitted with different types of heads to harvest different types of crops.

In one common arrangement, agricultural harvesting heads extend forward from the agricultural harvester to engage the plant stalks, sever the stalks, and carry the severed crop into the body of the agricultural harvester, itself, for processing. In agricultural harvesters, the throughput (amount of material moving through the machine) can be changed based on a number of factors, including various machine settings, such as the speed of the agricultural harvester along the ground, and the biomass of the vegetation encountered by the agricultural harvester. Some machine settings can be set, assuming a throughput, to effectively process the crop, and machine speed can then be varied, as the operator observes differences in vegetation biomass, to maintain the desired throughput.

The discussion above is merely provided for general background information and is not intended to be used as an aid in determining the scope of the claimed subject matter.

SUMMARY

One or more information maps are obtained by an agricultural work machine. The one or more information maps map one or more agricultural characteristic values at different geographic locations of a field. An in-situ sensor on the agricultural work machine senses an agricultural characteristic as the agricultural work machine moves through the field. A predictive map generator generates a predictive map that predicts a predictive agricultural characteristic at different locations in the field based on a relationship between the values in the one or more information maps and the agricultural characteristic sensed by the in-situ sensor. The predictive map can be output and used in automated machine control. This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to examples that solve any or all disadvantages noted in the background.

DETAILED DESCRIPTION

Figure 1:
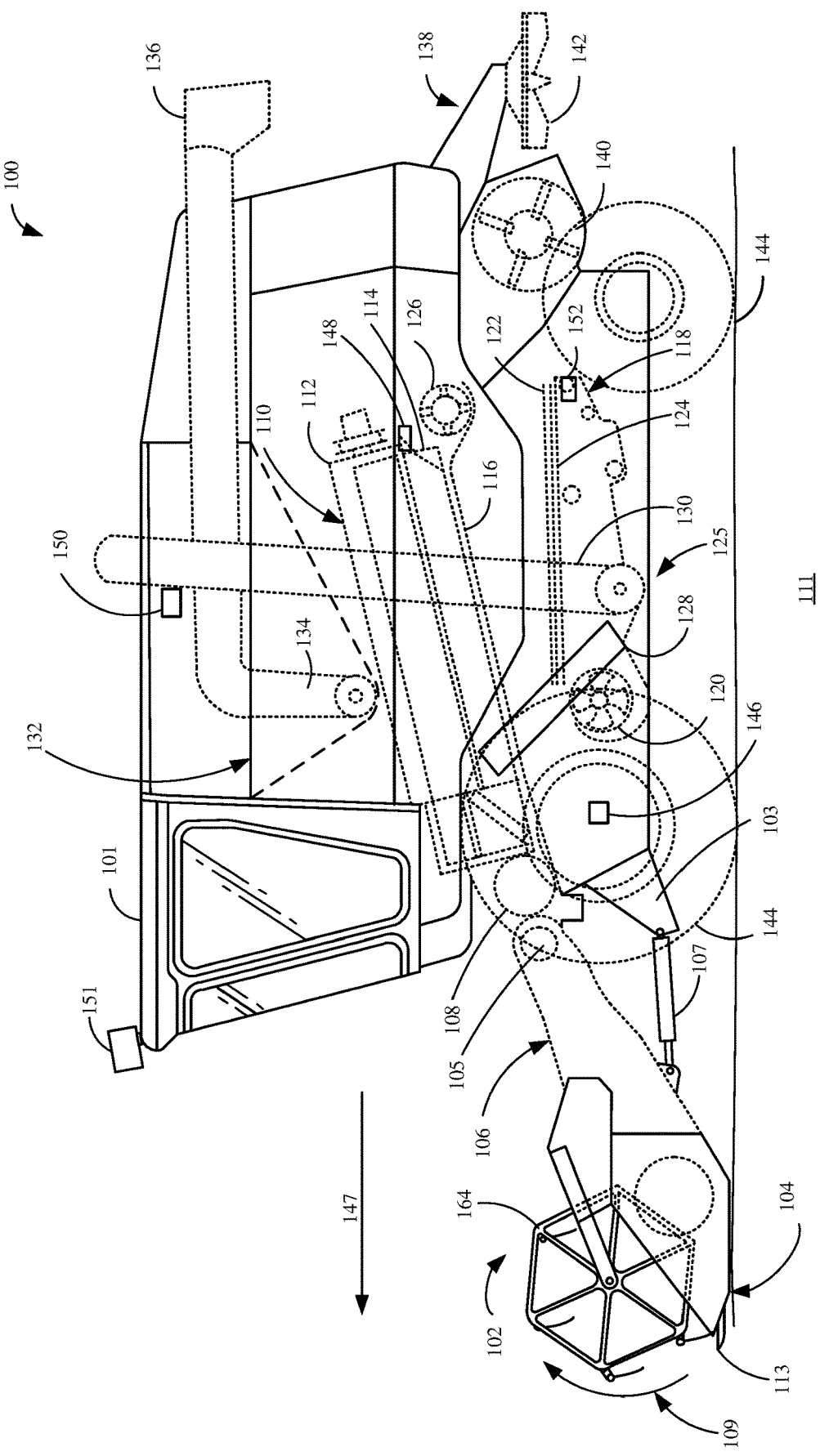
FIG. 1 is a partial pictorial, partial schematic illustration of one example of a combine harvester.

For the purposes of promoting an understanding of the principles of the present disclosure, reference will now be made to the examples illustrated in the drawings, and specific language will be used to describe the same. It will nevertheless be understood that no limitation of the scope of the disclosure is intended. Any alterations and further modifications to the described devices, systems, methods, and any further application of the principles of the present disclosure are fully contemplated as would normally occur to one skilled in the art to which the disclosure relates. In particular, it is fully contemplated that the features, components, and/or steps described with respect to one example may be combined with the features, components, and/or steps described with respect to other examples of the present disclosure.

The present description relates to using in-situ data taken concurrently with an agricultural operation, in combination with prior data, to generate a predictive map and, more particularly, a predictive biomass map. In some examples, the predictive biomass map can be used to control an agricultural work machine, such as an agricultural harvester. Biomass, as used herein, refers to an amount of above ground vegetation material, such as crop plants and weed plants, in a given area or location. Often, the amount is measured in terms of weight, for instance, weight per given area, such as tons per acre. Various characteristics can be indicative of biomass (referred to herein as biomass characteristics) and can be used to predict the biomass on a field of interest. For example, biomass characteristics can include various vegetation characteristics, such as vegetation height (e.g., the height of the vegetation above the surface of the field, such as the height of the crop or crop canopy above the surface of the field), vegetation density (the amount of crop matter in a given volume, which can be derived from the crop mass and crop volume), vegetation mass (such as a weight of the vegetation or the weight of vegetation components), or vegetation volume (how much of the given area or location is taken up by the vegetation, that is the space that the vegetation occupies or contains). It will be noted that the vegetation characteristics can include individual characteristics of different vegetation types, for instance, vegetation characteristics may be crop characteristics or weed characteristics. For instance, vegetation characteristics may include crop height, crop density, crop mass, or crop volume.

Thus, as used herein, vegetation characteristics, such as vegetation height, vegetation density, vegetation mass, or vegetation volume may include or comprise crop height, crop density, crop mass, or crop volume. In another example, biomass characteristics can include various machine characteristics of the agricultural harvester, such as machine settings, operating characteristics, or machine performance characteristics. For example, a force, such as a fluid pressure or torque, used to drive a threshing rotor of the agricultural harvester can be a machine characteristic indicative of the biomass.

The performance of an agricultural harvester may be affected when the agricultural harvester engages areas of the field with variances in biomass. For instance, if the machine settings of the agricultural harvester are set on the basis of an expected or desired throughput, the variance in biomass can cause the throughput to vary, and, thus, the machine settings can be suboptimal for effectively processing the vegetation, including the crop. As mentioned above, the operator can attempt to predict the biomass ahead of the machine. Additionally, some systems, such as feedback control systems, reactively adjust the forward ground speed of the agricultural harvester in an attempt to maintain a desired throughput. This can be done by attempting to identify the biomass based on sensor inputs, such as from sensors that sense a variable indicative of biomass. However, such arrangements can be prone to error and can be too slow to react to an upcoming change in biomass to effectively alter the operation of the machine to control throughput, such as by changing the forward speed of the harvester. For instance, such systems are typically reactive in that adjustments to the machine settings are made only after the vegetation has been encountered by the machine in attempt to reduce further error, such as in a feedback control system.

A vegetative index map illustratively maps vegetative index values (which may be indicative of vegetative growth) across different geographic locations in a field of interest. One example of a vegetative index includes a normalized difference vegetation index (NDVI). There are many other vegetative indices that are within the scope of the present disclosure. In some examples, a vegetative index may be derived from sensor readings of one or more bands of electromagnetic radiation reflected by the plants. Without limitations, these bands may be in the microwave, infrared, visible or ultraviolet portions of the electromagnetic spectrum.

A vegetative index map can be used to identify the presence and location of vegetation. In some examples, a vegetative index map enables crops to be identified and georeferenced in the presence of bare soil, crop residue, or other plants, such as weeds. In other examples, a vegetative index map enables the detection of various crop characteristics, such as crop growth and crop health or vigor, across different geographic locations in a field of interest. However, a vegetative index map may not accurately or reliably indicate other vegetation characteristics, such as vegetation characteristics indicative of a biomass of vegetation. Thus, in some instances, such as in accounting for biomass, a vegetative index map may have reduced usefulness in predicting how to control an agricultural harvester as the agricultural harvester moves through the field.

The present discussion thus proceeds with respect to systems that receive a vegetative index map of a field or map generated during a prior operation and also use an in-situ sensor to detect a variable indicative of biomass during a harvesting operation. In some instances, the in-situ sensor may detect a height, a density, a mass, or a volume of vegetation in an area or location on the field, for example, an area in front of a header attached to an agricultural harvester, such as header 102 of agricultural harvester 100. The detected height, density, mass, or volume of vegetation can be indicative of a biomass of the vegetation. For instance, by knowing the height of vegetation, such as the height of the crops or crop canopy above the surface of the field, a biomass of the vegetation can be estimated. This is because there is a relationship between the height of the vegetation and the biomass of the vegetation, generally, the greater the height, the greater the biomass. Other vegetation characteristics, such as density, mass, or volume, also have a relationship with biomass, such that a value of the vegetation characteristic can be correlated to biomass and thus a biomass of vegetation can be estimated. By detecting one or more of these vegetation characteristics a biomass level value can be predicted, for example, high, medium, or low biomass. In some examples, more finite values, such as predicted weight values, can also be predicted. By way of illustration, a detected crop height that is relatively high (relative to general or known heights of specific vegetation, such as specific crops or a specific genotype of a crop) can indicate a resultingly high biomass. In some examples, a single characteristic can be detected and used for the estimation of biomass. For instance, given a detected vegetation height, other vegetation characteristics, such as vegetation density, vegetation volume, or vegetation mass, can be estimated based on, for instance, vegetative index values, historical data, prior operation data (such as data obtained from a seeding map, which may contain genotype data, seed spacing data, seed depth data, and various other seeding characteristics data), crop genotype data (e.g., species data, hybrid data, cultivar data, etc.), operator or user input, third-party information, expert knowledge, machine learning, as well as a variety of other information, or combinations thereof. In some examples, a combination of characteristics can be detected and used for the estimation of biomass, for example, a combination of vegetation height, vegetation density, vegetation mass, or vegetation volume.

In another example, the in-situ sensor may detect a force, such as a fluid pressure or torque, used to drive a threshing rotor as an agricultural harvester processes crops, such as agricultural harvester 100. For example, the force used to drive the threshing rotor at a given setting, such as a given speed (e.g., RPM) setting, can be affected by the load on the drive system, such as an engine assembly or a hydraulic motor assembly. The force used to drive the threshing rotor at a given setting in an empty machine condition (where there is no vegetation being processed) can be known. Thus, additional force used to drive the threshing rotor at a given setting when the harvester is processing vegetation can be indicative of a biomass of the vegetation being processed as the biomass of the vegetation will increase the load on the drive system.

The systems generate a model that models a relationship between the vegetative index values on the vegetative index map or the values on the map generated from the prior operation and the output values from the in-situ sensor. The model is used to generate a functional predictive biomass map that predicts, for example, biomass at different locations in the field. The functional predictive biomass map, generated during the harvesting operation, can be presented to an operator or other user or used in automatically controlling a harvester during the harvesting operation, or both.

FIG. 1 is a partial pictorial, partial schematic, illustration of a self-propelled agricultural harvester 100. In the illustrated example, agricultural harvester 100 is a combine harvester. Further, although combine harvesters are provided as examples throughout the present disclosure, it will be appreciated that the present description is also applicable to other types of harvesters, such as cotton harvesters, sugarcane harvesters, self-propelled forage harvesters, windrowers, or other agricultural work machines. Consequently, the present disclosure is intended to encompass the various types of harvesters described and is, thus, not limited to combine harvesters. Moreover, the present disclosure is directed to other types of work machines, such as agricultural seeders and sprayers, construction equipment, forestry equipment, and turf management equipment where generation of a predictive map may be applicable. Consequently, the present disclosure is intended to encompass these various types of harvesters and other work machines and is, thus, not limited to combine harvesters.

As shown in FIG. 1, agricultural harvester 100 illustratively includes an operator compartment 101, which can have a variety of different operator interface mechanisms, for controlling agricultural harvester 100. Agricultural harvester 100 includes front-end equipment, such as a header 102, and a cutter generally indicated at 104. Agricultural harvester 100 also includes a feeder house 106, a feed accelerator 108, and a thresher generally indicated at 110. The feeder house 106 and the feed accelerator 108 form part of a material handling subsystem 125. Header 102 is pivotally coupled to a frame 103 of agricultural harvester 100 along pivot axis 105. One or more actuators 107 drive movement of header 102 about axis 105 in the direction generally indicated by arrow 109. Thus, a vertical position of header 102 (the header height) above ground 111 over which the header 102 travels is controllable by actuating actuator 107. While not shown in FIG. 1, agricultural harvester 100 may also include one or more actuators that operate to apply a tilt angle, a roll angle, or both to the header 102 or portions of header 102. Tilt refers to an angle at which the cutter 104 engages the crop. The tilt angle is increased, for example, by controlling header 102 to point a distal edge 113 of cutter 104 more toward the ground. The tilt angle is decreased by controlling header 102 to point the distal edge 113 of cutter 104 more away from the ground. The roll angle refers to the orientation of header 102 about the front-to-back longitudinal axis of agricultural harvester 100.

Thresher 110 illustratively includes a threshing rotor 112 and a set of concaves 114. Further, agricultural harvester 100 also includes a separator 116. Agricultural harvester 100 also includes a cleaning subsystem or cleaning shoe (collectively referred to as cleaning subsystem 118) that includes a cleaning fan 120, chaffer 122, and sieve 124. The material handling subsystem 125 also includes discharge beater 126, tailings elevator 128, clean grain elevator 130, as well as unloading auger 134 and spout 136. The clean grain elevator moves clean grain into clean grain tank 132. Agricultural harvester 100 also includes a residue subsystem 138 that can include chopper 140 and spreader 142. Agricultural harvester 100 also includes a propulsion subsystem that includes an engine that drives ground engaging components 144, such as wheels or tracks. In some examples, a combine harvester within the scope of the present disclosure may have more than one of any of the subsystems mentioned above. In some examples, agricultural harvester 100 may have left and right cleaning subsystems, separators, etc., which are not shown in FIG. 1.

In operation, and by way of overview, agricultural harvester 100 illustratively moves through a field in the direction indicated by arrow 147. As agricultural harvester 100 moves, header 102 (and the associated reel 164) engages the crop to be harvested and gathers the crop toward cutter 104. An operator of agricultural harvester 100 can be a local human operator, a remote human operator, or an automated system. An operator command is a command by an operator. The operator of agricultural harvester 100 may determine one or more of a height setting, a tilt angle setting, or a roll angle setting for header 102. For example, the operator inputs a setting or settings to a control system, described in more detail below, that controls actuator 107. The control system may also receive a setting from the operator for establishing the tilt angle and roll angle of the header 102 and implement the inputted settings by controlling associated actuators, not shown, that operate to change the tilt angle and roll angle of the header 102. The actuator 107 maintains header 102 at a height above ground 111 based on a height setting and, where applicable, at desired tilt and roll angles. Each of the height, roll, and tilt settings may be implemented independently of the others. The control system responds to header error (e.g., the difference between the height setting and measured height of header 104 above ground 111 and, in some examples, tilt angle and roll angle errors) with a responsiveness that is determined based on a selected sensitivity level. If the sensitivity level is set at a greater level of sensitivity, the control system responds to smaller header position errors, and attempts to reduce the detected errors more quickly than when the sensitivity is at a lower level of sensitivity.

Returning to the description of the operation of agricultural harvester 100, after crops are cut by cutter 104, the severed crop material is moved by a conveyor in feeder house 106 toward feed accelerator 108, which accelerates the crop material into thresher 110. The crop material is threshed by rotor 112 rotating the crop against concaves 114. The force used to drive (or power) rotor 112 can be sensed, and the sensed force, or sensed indication of force, can be used to determine a biomass being threshed. For instance, the fluid pressure, such a hydraulic or pneumatic pressure, that is used to drive rotor 112 can be sensed, and the sensed fluid pressure can be used to determine a biomass being processed by agricultural harvester 100. In another example, the torque used to drive rotor 112 can be sensed, and the sensed torque can be used to determine a biomass being processed by agricultural harvester 100. Threshing rotor drive force can be used as an indication of the biomass being processed by the thresher in agricultural harvester 100, as the threshing rotor drive force is the force, such as torque or pressure, used to maintain the threshing rotor 112 at a desired speed. The threshing rotor drive force correlates (along with various other machine settings, such as concave settings and threshing rotor speed settings) with the biomass moving through the thresher in agricultural harvester 100 at a particular time. In some instances, threshing rotor 112 can be driven (or powered) by other power systems, and the power from those other power systems that is used to operate the threshing rotor can be sensed and used as an indication of a biomass being processed through the thresher in agricultural harvester 100.

The threshed crop material is moved by a separator rotor in separator 116 where a portion of the residue is moved by discharge beater 126 toward the residue subsystem 138. The portion of residue transferred to the residue subsystem 138 is chopped by residue chopper 140 and spread on the field by spreader 142. In other configurations, the residue is released from the agricultural harvester 100 in a windrow. In other examples, the residue subsystem 138 can include weed seed eliminators (not shown) such as seed baggers or other seed collectors, or seed crushers or other seed destroyers.

Grain falls to cleaning subsystem 118. Chaffer 122 separates some larger pieces of material from the grain, and sieve 124 separates some of finer pieces of material from the clean grain. Clean grain falls to an auger that moves the grain to an inlet end of clean grain elevator 130, and the clean grain elevator 130 moves the clean grain upwards, depositing the clean grain in clean grain tank 132. Residue is removed from the cleaning subsystem 118 by airflow generated by cleaning fan 120. Cleaning fan 120 directs air along an airflow path upwardly through the sieves and chaffers. The airflow carries residue rearwardly in agricultural harvester 100 toward the residue handling subsystem 138.

Tailings elevator 128 returns tailings to thresher 110 where the tailings are re-threshed. Alternatively, the tailings also may be passed to a separate re-threshing mechanism by a tailings elevator or another transport device where the tailings are re-threshed as well.

FIG. 1 also shows that, in one example, agricultural harvester 100 includes ground speed sensor 146, one or more separator loss sensors 148, a clean grain camera 150, a forward looking image capture mechanism 151, which may be in the form of a stereo or mono camera, and one or more loss sensors 152 provided in the cleaning subsystem 118.

Ground speed sensor 146 senses the travel speed of agricultural harvester 100 over the ground. Ground speed sensor 146 may sense the travel speed of the agricultural harvester 100 by sensing the speed of rotation of the ground engaging components (such as wheels or tracks), a drive shaft, an axel, or other components. In some instances, the travel speed may be sensed using a positioning system, such as a global positioning system (GPS), a dead reckoning system, a long range navigation (LORAN) system, or a wide variety of other systems or sensors that provide an indication of travel speed.

Loss sensors 152 illustratively provide an output signal indicative of the quantity of grain loss occurring in both the right and left sides of the cleaning subsystem 118. In some examples, sensors 152 are strike sensors which count grain strikes per unit of time or per unit of distance traveled to provide an indication of the grain loss occurring at the cleaning subsystem 118. The strike sensors for the right and left sides of the cleaning subsystem 118 may provide individual signals or a combined or aggregated signal. In some examples, sensors 152 may include a single sensor as opposed to separate sensors provided for each cleaning subsystem 118. Separator loss sensor 148 provides a signal indicative of grain loss in the left and right separators, not separately shown in FIG. 1. The separator loss sensors 148 may be associated with the left and right separators and may provide separate grain loss signals or a combined or aggregate signal. In some instances, sensing grain loss in the separators may also be performed using a wide variety of different types of sensors as well.

Agricultural harvester 100 may also include other sensors and measurement mechanisms. For instance, agricultural harvester 100 may include one or more of the following sensors: a header height sensor that senses a height of header 102 above ground 111; stability sensors that sense oscillation or bouncing motion (such as oscillation frequency and amplitude) of agricultural harvester 100; a residue setting sensor that is configured to sense whether agricultural harvester 100 is configured to chop the residue, produce a windrow, etc.; a cleaning shoe fan speed sensor to sense the speed of fan 120; a concave clearance sensor that senses a size of the clearance between the rotor 112 and concaves 114; a threshing rotor speed sensor that senses a rotor speed of rotor 112; a force sensor that senses a force used to drive threshing rotor 112, such as a pressure sensor that senses a fluid pressure used to drive threshing rotor 112 or a torque sensor that senses a torque used to drive threshing rotor 112; a chaffer clearance sensor that senses the size of openings in chaffer 122; a sieve clearance sensor that senses the size of openings in sieve 124; a material other than grain (MOG) moisture sensor that senses a moisture level of the MOG passing through agricultural harvester 100; one or more machine setting sensors configured to sense various configurable settings of agricultural harvester 100; a machine orientation sensor that senses the orientation of agricultural harvester 100; and crop property sensors that sense a variety of different types of crop properties, such as crop height, crop density, crop volume, crop mass, and other crop properties. Crop property sensors may also be configured to sense characteristics of the severed crop material as the crop material is being processed by agricultural harvester 100. For example, in some instances, the crop property sensors may sense grain quality such as broken grain, MOG levels; grain constituents such as starches and protein; and grain feed rate as the grain travels through the feeder house 106, clean grain elevator 130, or elsewhere in the agricultural harvester 100. The crop property sensors may also sense the feed rate of biomass through feeder house 106, through the separator 116 or elsewhere in agricultural harvester 100. The crop property sensors may also sense the feed rate as a mass flow rate of grain through elevator 130 or through other portions of the agricultural harvester 100 or provide other output signals indicative of other sensed variables. Crop property sensors can include one or more yield sensors that sense crop yield being harvested by the agricultural harvester.

In one example, various machine settings can be set or controlled to achieve a desired performance. The machine settings can include such things as concave clearance, threshing rotor speed, sieve and chaffer settings, and cleaning fan speed. Other machine settings can also be controlled. These machine settings can illustratively be set or controlled based on an expected throughput, that is, the amount of material processed by agricultural harvester 100 per unit of time. Thus, if the biomass varies spatially in the field and the ground speed of agricultural harvester 100 remains constant, then the throughput will change with biomass. In some examples, the biomass being processed is indicated by sensing the force used to drive threshing rotor 112 at a desired speed, and the ground speed of agricultural harvester 100 is varied in an attempt to maintain the desired throughput. In other examples, forward looking image capture mechanism 151 can be used to estimate one or more of a vegetation height, a vegetation density, a vegetation volume, and a vegetation mass in a given area of the field ahead of agricultural harvester 100 to predict a biomass that is about to be processed by agricultural harvester 100. Other vegetation characteristics may also be estimated using the captured image(s) from the forward looking image capture mechanism 151. In such examples, the vegetation characteristics can be converted into a georeferenced biomass value indicative of the biomass that is about to be engaged by agricultural harvester 100 in an upcoming area of the field. The machine speed, as well as various other machine settings, such as header height, can be controlled based on the estimated biomass to maintain the desired throughput.

Prior to describing how agricultural harvester 100 generates a functional predictive biomass map and uses the functional predictive biomass map for control, a brief description of some of the items on agricultural harvester 100 and their respective operations will first be described. The description of FIGS. 2 and 3 describe receiving a general type of prior information map and combining information from the prior information map with a georeferenced sensor signal generated by an in-situ sensor, where the sensor signal is indicative of a characteristic in the field, such as characteristics of crop present in the field. Characteristics of the field may include, but are not limited to, characteristics of a field such as slope, weed intensity, weed type, soil moisture, surface quality; characteristics of vegetation properties, such as vegetation height, vegetation volume, vegetation moisture, vegetation mass, and vegetation density; characteristics of crop properties, such as crop height, crop volume, crop moisture, crop mass, crop density, and crop state; characteristics of grain properties such as grain moisture, grain size, grain test weight; and characteristics of machine performance such as loss levels, job quality, fuel consumption, and power utilization. A relationship between the characteristic values obtained from in-situ sensor signals and the prior information map values is identified, and that relationship is used to generate a new functional predictive map. A functional predictive map predicts values at different geographic locations in a field, and one or more of those values may be used for controlling a machine, such as one or more subsystems of an agricultural harvester. In some instances, a functional predictive map can be presented to a user, such as an operator of an agricultural work machine, which may be an agricultural harvester. A functional predictive map may be presented to a user visually, such as via a display, haptically, or audibly. The user may interact with the functional predictive map to perform editing operations and other user interface operations. In some instances, a functional predictive map can be used for one or more of controlling an agricultural work machine, such as an agricultural harvester, presentation to an operator or other user, and presentation to an operator or user for interaction by the operator or user.

Figure 2:
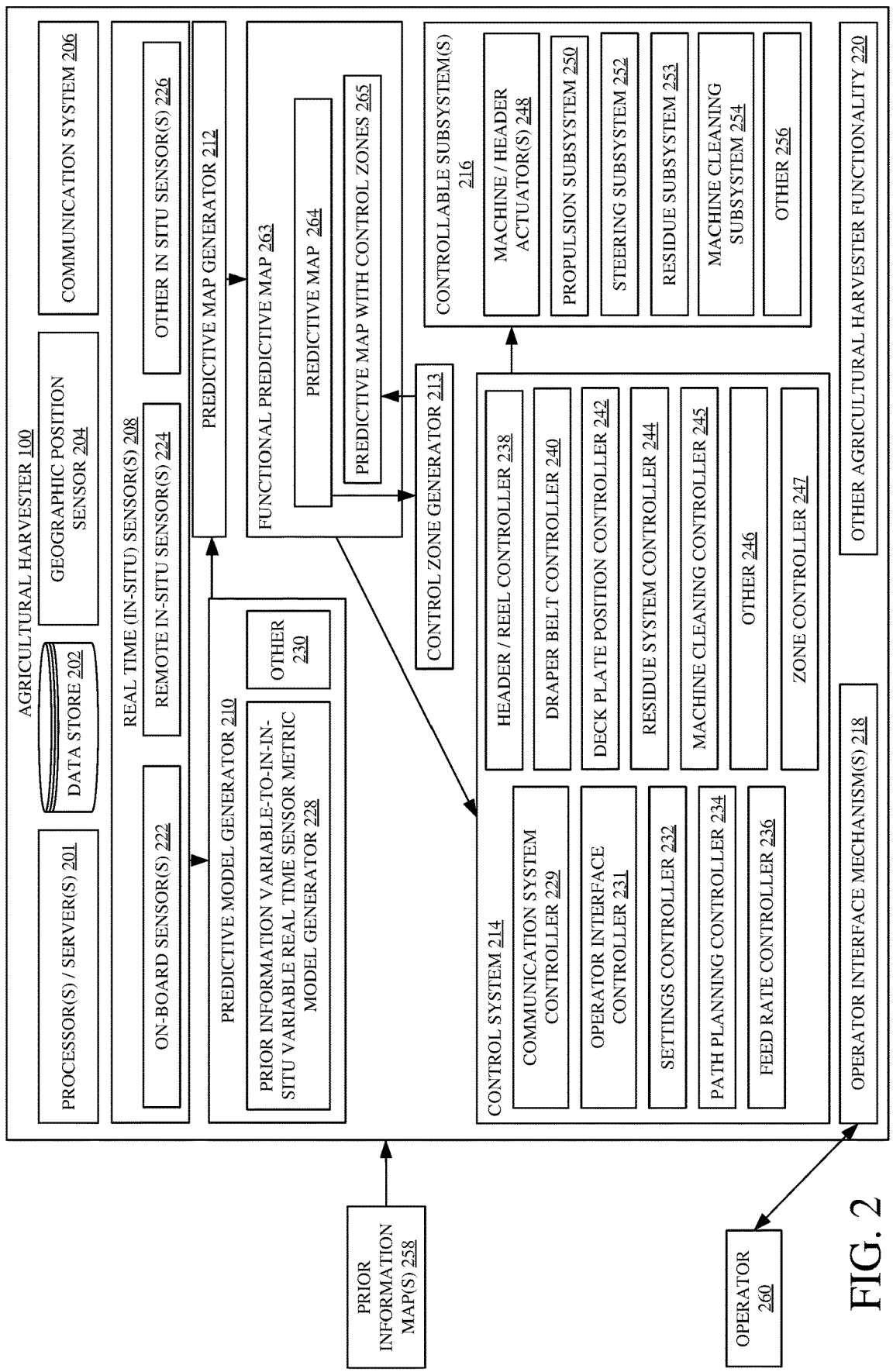
FIG. 2 is a block diagram showing some portions of an agricultural harvester in more detail, according to some examples of the present disclosure.
Figure 3A:
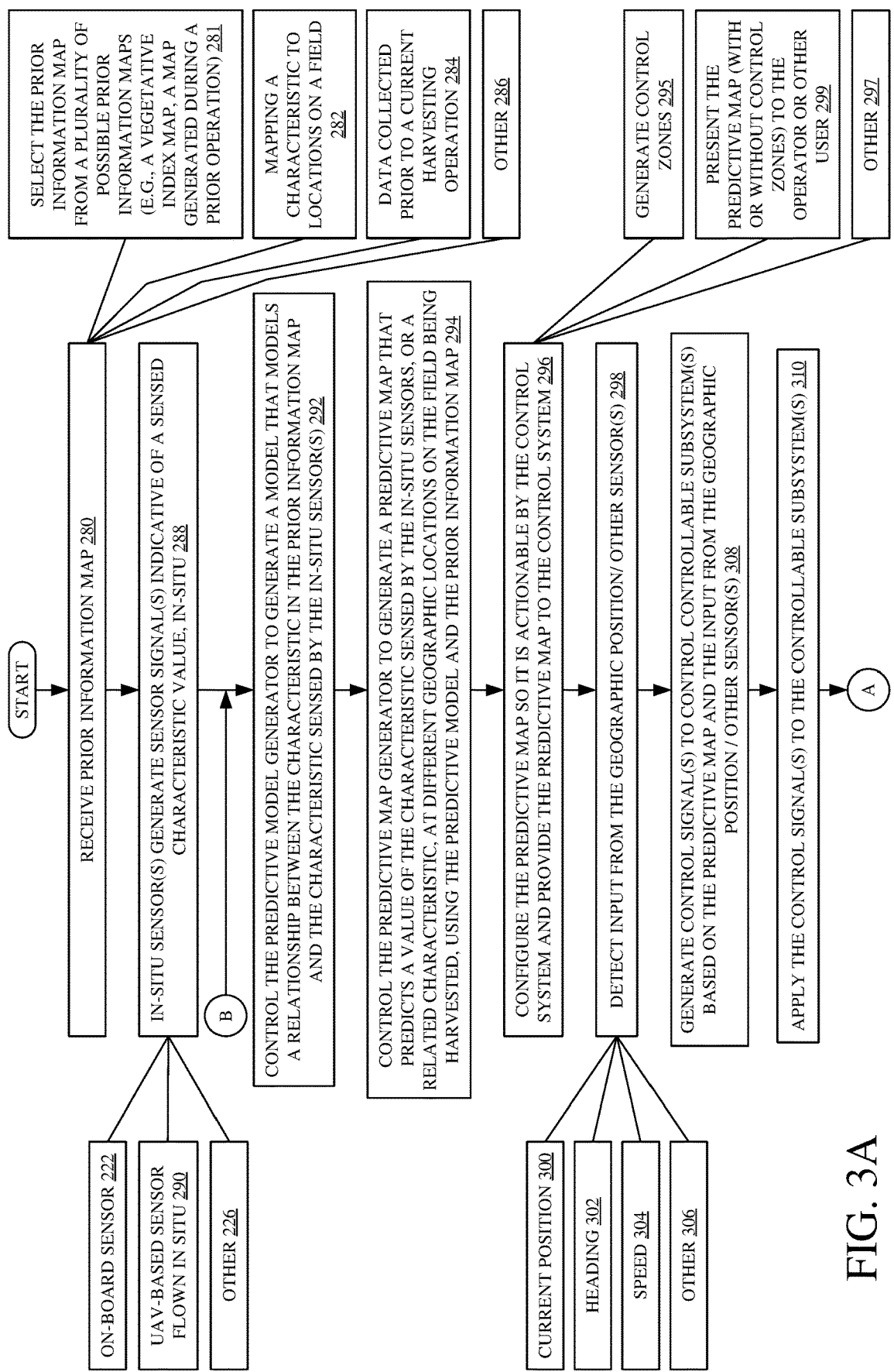
FIGS. 3A-3B (collectively referred to herein as FIG. 3) show a flow diagram illustrating an example of operation of an agricultural harvester in generating a map.
Figure 3B:
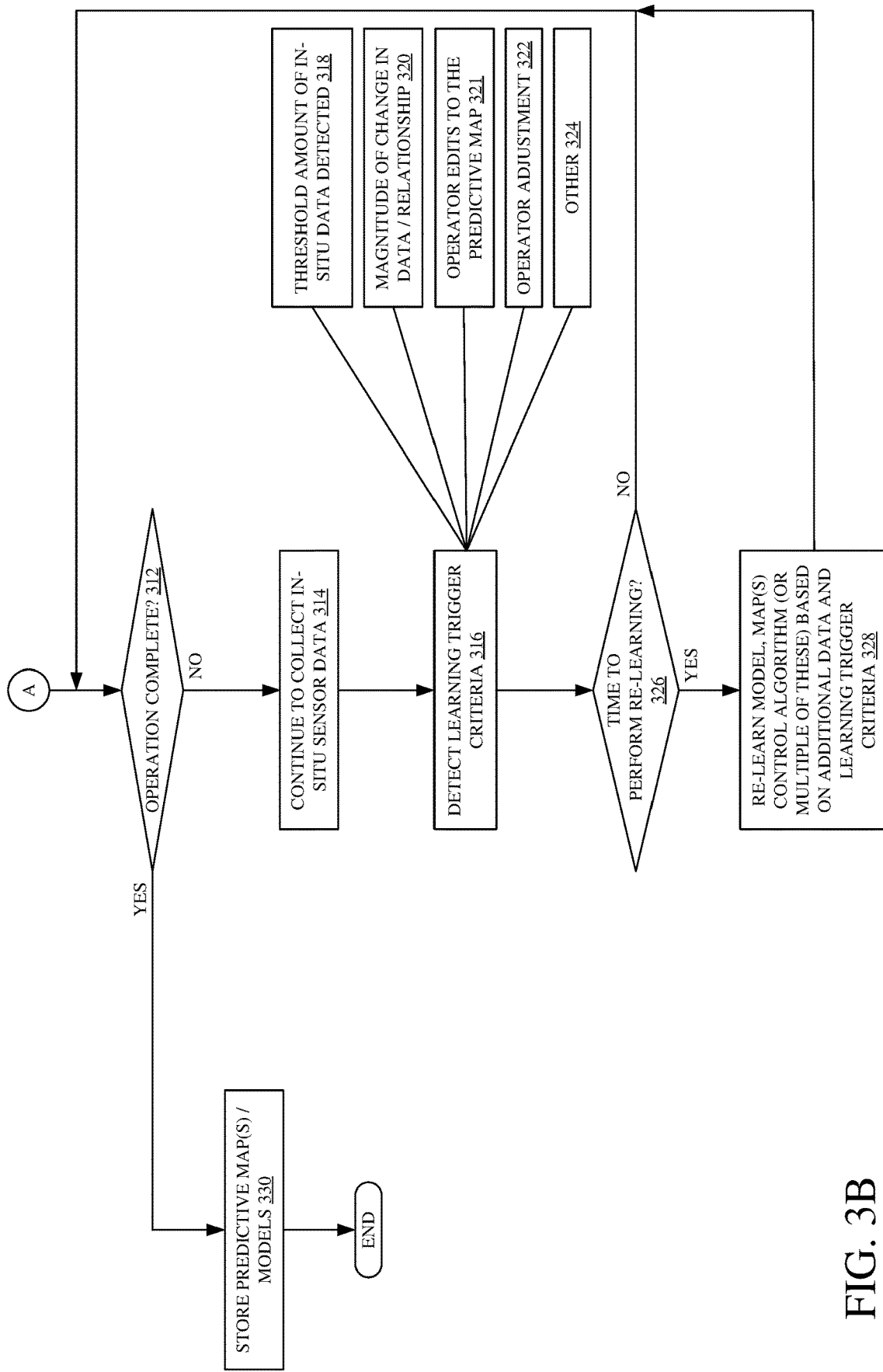
Figure 4:
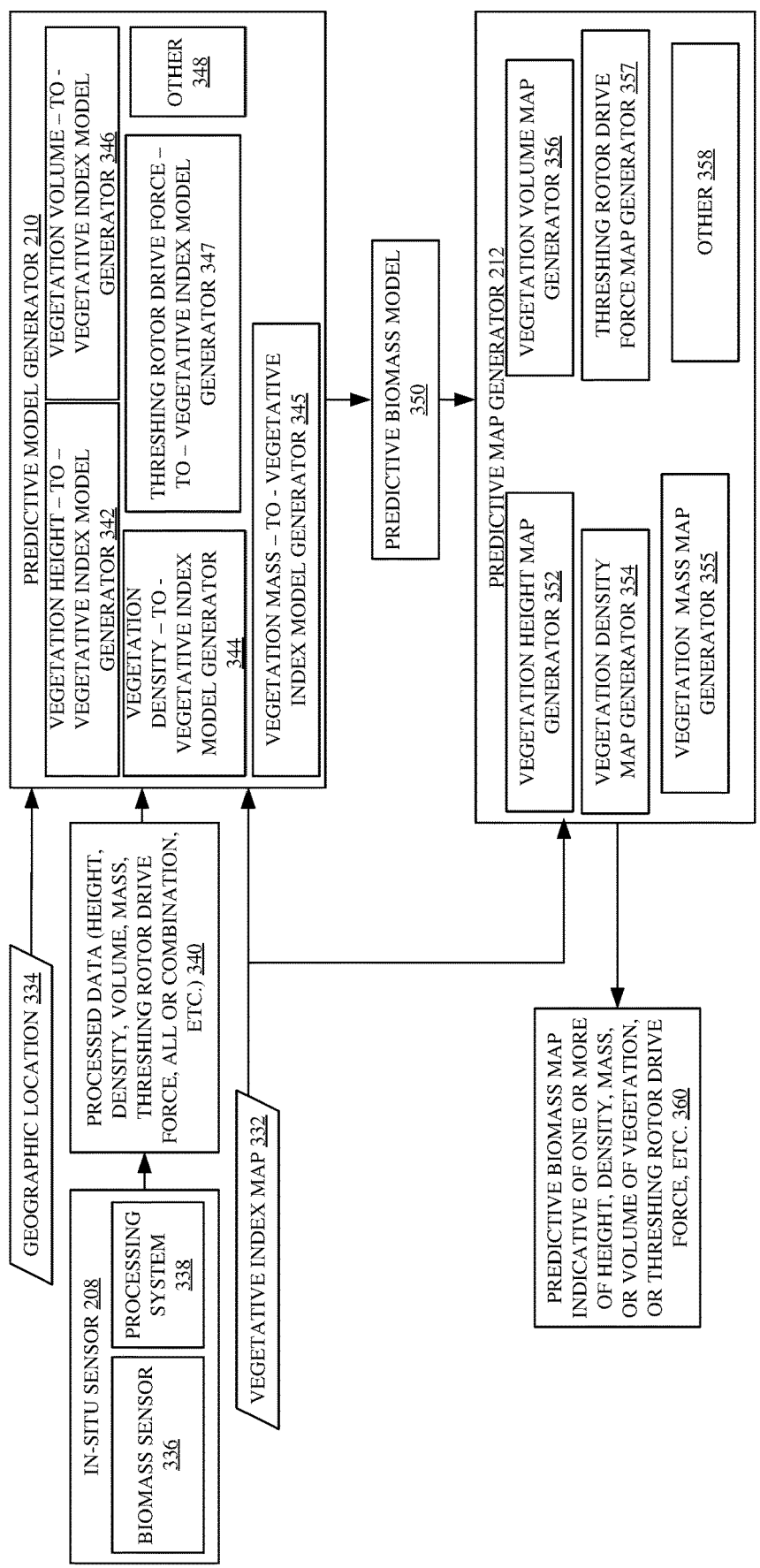
FIG. 4 is a block diagram showing one example of a predictive model generator and a predictive metric map generator.
Figure 5:
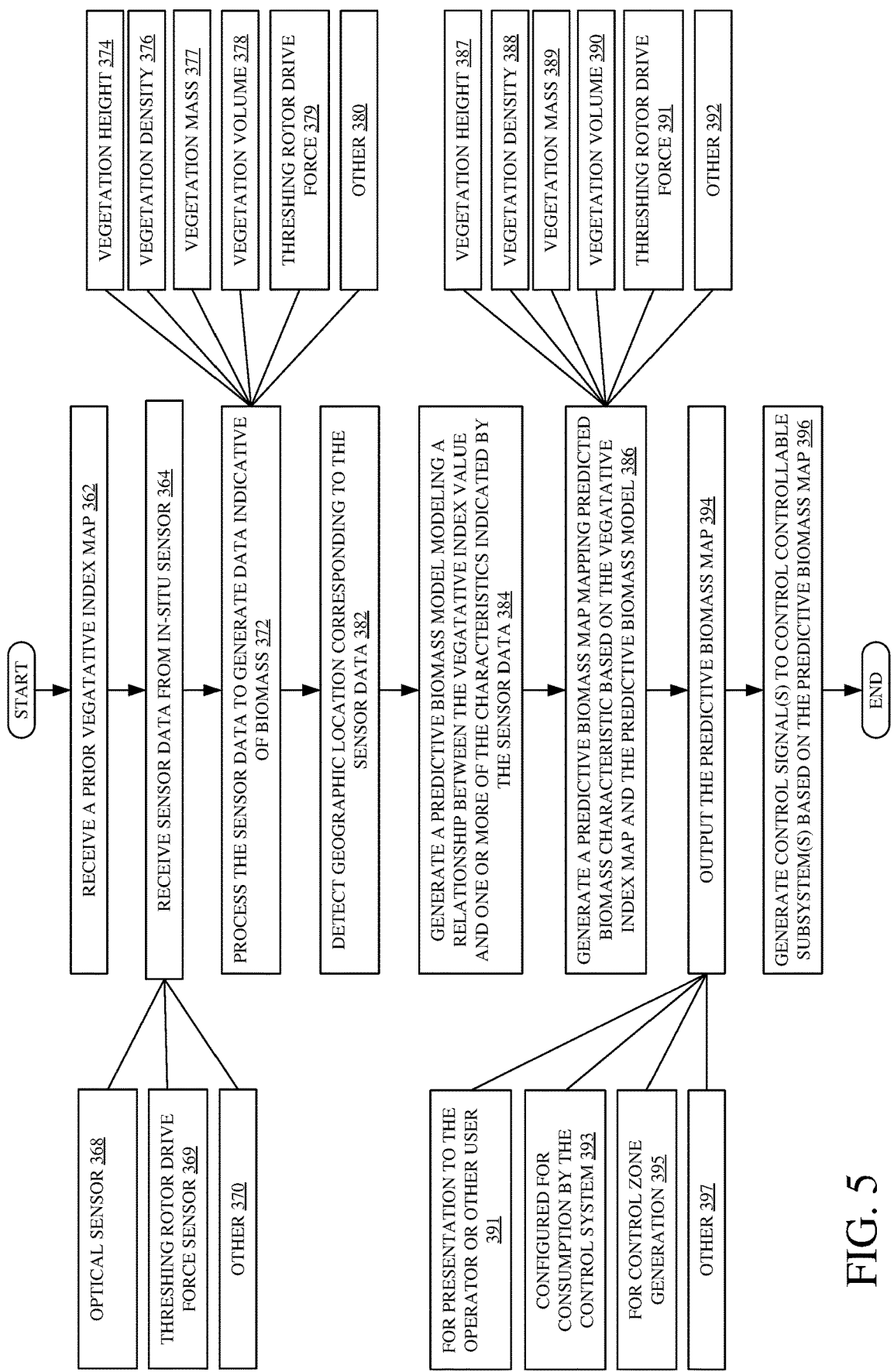
FIG. 5 is a flow diagram showing an example of operation of an agricultural harvester in receiving a vegetative index map, detecting a characteristic, and generating a functional predictive biomass map for use in controlling the agricultural harvester during a harvesting operation.

After the general approach is described with respect to FIGS. 2 and 3, a more specific approach for generating a functional predictive biomass map that can be presented to an operator or user, or used to control agricultural harvester 100, or both is described with respect to FIGS. 4 and 5. Again, while the present discussion proceeds with respect to the agricultural harvester and, particularly, a combine harvester, the scope of the present disclosure encompasses other types of agricultural harvesters or other agricultural work machines.

FIG. 2 is a block diagram showing some portions of an example agricultural harvester 100. FIG. 2 shows that agricultural harvester 100 illustratively includes one or more processors or servers 201, data store 202, geographic position sensor 204, communication system 206, and one or more in-situ sensors 208 that sense one or more agricultural characteristics of a field concurrent with a harvesting operation. An agricultural characteristic can include any characteristic that can have an effect of the harvesting operation. Some examples of agricultural characteristics include characteristics of the harvesting machine, the field, the plants on the field, and the weather. Other types of agricultural characteristics are also included. The in-situ sensors 208 generate values corresponding to the sensed characteristics. The agricultural harvester 100 also includes a predictive model or relationship generator (collectively referred to hereinafter as "predictive model generator 210"), predictive map generator 212, control zone generator 213, control system 214, one or more controllable subsystems 216, and an operator interface mechanism 218. The agricultural harvester 100 can also include a wide variety of other agricultural harvester functionality 220. The in-situ sensors 208 include, for example, on-board sensors 222, remote sensors 224, and other sensors 226 that sense characteristics of a field during the course of an agricultural operation. Predictive model generator 210 illustratively includes a prior information variable-to-in-situ variable model generator 228, and predictive model generator 210 can include other items 230. Control system 214 includes communication system controller 229, operator interface controller 231, a settings controller 232, path planning controller 234, feed rate controller 236, header and reel controller 238, draper belt controller 240, deck plate position controller 242, residue system controller 244, machine cleaning controller 245, zone controller 247, and system 214 can include other items 246. Controllable subsystems 216 include machine and header actuators 248, propulsion subsystem 250, steering subsystem 252, residue subsystem 138, machine cleaning subsystem 254, and subsystems 216 can include a wide variety of other subsystems 256.

FIG. 2 also shows that agricultural harvester 100 can receive prior information map 258. As described below, the prior information map 258 includes, for example, a vegetative index map or a vegetation map from a prior operation. However, prior information map 258 may also encompass other types of data that were obtained prior to a harvesting operation or a map from a prior operation. FIG. 2 also shows that an operator 260 may operate the agricultural harvester 100. The operator 260 interacts with operator interface mechanisms 218. In some examples, operator interface mechanisms 218 may include joysticks, levers, a steering wheel, linkages, pedals, buttons, dials, keypads, user actuatable elements (such as icons, buttons, etc.) on a user interface display device, a microphone and speaker (where speech recognition and speech synthesis are provided), among a wide variety of other types of control devices. Where a touch sensitive display system is provided, operator 260 may interact with operator interface mechanisms 218 using touch gestures. These examples described above are provided as illustrative examples and are not intended to limit the scope of the present disclosure. Consequently, other types of operator interface mechanisms 218 may be used and are within the scope of the present disclosure.

Prior information map 258 may be downloaded onto agricultural harvester 100 and stored in data store 202, using communication system 206 or in other ways. In some examples, communication system 206 may be a cellular communication system, a system for communicating over a wide area network or a local area network, a system for communicating over a near field communication network, or a communication system configured to communicate over any of a variety of other networks or combinations of networks. Communication system 206 may also include a system that facilitates downloads or transfers of information to and from a secure digital (SD) card or a universal serial bus (USB) card or both.

Geographic position sensor 204 illustratively senses or detects the geographic position or location of agricultural harvester 100. Geographic position sensor 204 can include, but is not limited to, a global navigation satellite system (GNSS) receiver that receives signals from a GNSS satellite transmitter. Geographic position sensor 204 can also include a real-time kinematic (RTK) component that is configured to enhance the precision of position data derived from the GNSS signal. Geographic position sensor 204 can include a dead reckoning system, a cellular triangulation system, or any of a variety of other geographic position sensors.

In-situ sensors 208 may be any of the sensors described above with respect to FIG. 1. In-situ sensors 208 include on-board sensors 222 that are mounted on-board agricultural harvester 100. Such sensors may include, for instance, a perception sensor (e.g., a forward looking mono or stereo camera system and image processing system), image sensors that are internal to agricultural harvester 100 (such as the clean grain camera or cameras mounted to identify weed seeds that are exiting agricultural harvester 100 through the residue subsystem or from the cleaning subsystem). The in-situ sensors 208 also include remote in-situ sensors 224 that capture in-situ information. In-situ data include data taken from a sensor on-board the agricultural harvester or taken by any sensor where the data are detected during the harvesting operation.

Predictive model generator 210 generates a model that is indicative of a relationship between the values sensed by the in-situ sensor 208 and a value mapped to the field by the prior information map 258. For example, if the prior information map 258 maps a vegetative index value to different locations in the field, and the in-situ sensor 208 senses a value indicative of biomass, then prior information variable-to-in-situ variable model generator 228 generates a predictive biomass model that models the relationship between the vegetative index value and the biomass value, such that a biomass value, for a location in the field, can be predicted based on the vegetative index value corresponding to that location. This is because the biomass, at any given location in the field, may be affected by or have a relationship to a characteristic indicated by the vegetative index values contained in the prior information map 258, such as crop growth or crop health associated with the corresponding locations in the field. The predictive biomass model can also be generated based on vegetative index values from the prior information map 258 and multiple in-situ data values generated by in-situ sensors 208. Predictive map generator 212 uses the predictive biomass model generated by predictive model generator 210 to generate a functional predictive biomass map that predicts the value of biomass or a biomass characteristic, such as vegetation height, vegetation density, vegetation volume, or vegetation volume, or vegetation characteristics of specific types of vegetation, such as crops, for instance, crop height, crop density, crop volume, or crop mass. In other examples, the biomass characteristic may be a force used to drive the threshing rotor. The predicted biomass or biomass characteristic values are generated using both the values sensed by the in-situ sensor or sensors 208 (which may be the sensed values of biomass or a biomass characteristic) at different locations in the field and the values of the characteristic mapped in the prior information map 258, such as vegetative index values, corresponding to those locations in the field.

In some examples, the type of values in the functional predictive map 263 may be the same as the in-situ data type sensed by the in-situ sensors 208. In some instances, the type of values in the functional predictive map 263 may have different units from the data sensed by the in-situ sensors 208. In some examples, the type of values in the functional predictive map 263 may be different from the data type sensed by the in-situ sensors 208 but have a relationship to the type of data type sensed by the in-situ sensors 208. For example, in some examples, the data type sensed by the in-situ sensors 208 may be indicative of the type of values in the functional predictive map 263. In some examples, the type of data in the functional predictive map 263 may be different than the data type in the prior information map 258. In some instances, the type of data in the functional predictive map 263 may have different units from the data in the prior information map 258. In some examples, the type of data in the functional predictive map 263 may be different from the data type in the prior information map 258 but has a relationship to the data type in the prior information map 258. For example, in some examples, the data type in the prior information map 258 may be indicative of the type of data in the functional predictive map 263. In some examples, the type of data in the functional predictive map 263 is different than one of, or both of the in-situ data type sensed by the in-situ sensors 208 and the data type in the prior information map 258. In some examples, the type of data in the functional predictive map 263 is the same as one of, or both of, of the in-situ data type sensed by the in-situ sensors 208 and the data type in prior information map 258. In some examples, the type of data in the functional predictive map 263 is the same as one of the in-situ data type sensed by the in-situ sensors 208 or the data type in the prior information map 258, and different than the other.

Continuing with the preceding example in which prior information map 258 is a vegetative index map and in-situ sensor 208 senses a value indicative of biomass, predictive map generator 212 uses the vegetative index values in prior information map 258 and the model generated by predictive model generator 210 to generate a functional predictive map 263 that predicts the biomass at different locations in the field. Predictive map generator 212 thus outputs predictive map 264.

As shown in FIG. 2, predictive map 264 predicts the value of a sensed characteristic (sensed by in-situ sensors 208), or a characteristic related to the sensed characteristic, at various locations across the field based upon a prior information value in prior information map 258 at those locations and using the predictive model. For example, if predictive model generator 210 has generated a predictive model indicative of a relationship between a vegetative index value and biomass, then, given the vegetative index value at different locations across the field, predictive map generator 212 generates a predictive map 264 that predicts the value of the biomass at different locations across the field. The vegetative index value, obtained from the vegetative index map, at those locations and the relationship between the vegetative index value and biomass, obtained from the predictive model, are used to generate the predictive map 264.

Some variations in the data types that are mapped in the prior information map 258, the data types sensed by in-situ sensors 208, and the data types predicted on the predictive map 264 will now be described.

In some examples, the data type in the prior information map 258 is different from the data type sensed by in-situ sensors 208, yet the data type in the predictive map 264 is the same as the data type sensed by the in-situ sensors 208. For instance, the prior information map 258 may be a vegetative index map, and the variable sensed by the in-situ sensors 208 may be vegetation height. The predictive map 264 may then be a predictive vegetation height map that maps predicted vegetation height values to different geographic locations in the field. In another example, the prior information map 258 may be a vegetative index map, and the variable sensed by the in-situ sensors 208 may be vegetation density. The predictive map 264 may then be a predictive vegetation density map that maps predicted vegetation density values to different geographic locations in the field.

Also, in some examples, the data type in the prior information map 258 is different from the data type sensed by in-situ sensors 208, and the data type in the predictive map 264 is different from both the data type in the prior information map 258 and the data type sensed by the in-situ sensors 208. For instance, the prior information map 258 may be a vegetative index map, and the variable sensed by the in-situ sensors 208 may be crop height. In such an example, the predictive map 264 may be a predictive biomass map that maps predicted biomass values to different geographic locations in the field. In another example, the prior information map 258 may be a vegetative index map, and the variable sensed by the in-situ sensors 208 may be threshing rotor drive force. In such an example, the predictive map 264 may be a predictive biomass map that maps predicted biomass values to different geographic locations in the field.

In some examples, the prior information map 258 is from a prior pass through the field during a prior operation and the data type is different from the data type sensed by in-situ sensors 208, yet the data type in the predictive map 264 is the same as the data type sensed by the in-situ sensors 208. For instance, the prior information map 258 may be a seed population map generated during planting, and the variable sensed by the in-situ sensors 208 may be stalk size. The predictive map 264 may then be a predictive stalk size map that maps predicted stalk size values to different geographic locations in the field. In another example, the prior information map 258 may be a seeding hybrid map, and the variable sensed by the in-situ sensors 208 may be crop state such as standing crop or down crop. The predictive map 264 may then be a predictive crop state map that maps predicted crop state values to different geographic locations in the field.

In some examples, the prior information map 258 is from a prior pass through the field during a prior operation and the data type is the same as the data type sensed by in-situ sensors 208, and the data type in the predictive map 264 is also the same as the data type sensed by the in-situ sensors 208. For instance, the prior information map 258 may be a yield map generated during a previous year, and the variable sensed by the in-situ sensors 208 may be yield. The predictive map 264 may then be a predictive yield map that maps predicted yield values to different geographic locations in the field. In such an example, the relative yield differences in the georeferenced prior information map 258 from the prior year can be used by predictive model generator 210 to generate a predictive model that models a relationship between the relative yield differences on the prior information map 258 and the yield values sensed by in-situ sensors 208 during the current harvesting operation. The predictive model is then used by predictive map generator 210 to generate a predictive yield map.

In another example, the prior information map 258 may be a weed intensity map generated during a prior operation, such as from a sprayer, and the variable sensed by the in-situ sensors 208 may be weed intensity. The predictive map 264 may then be a predictive weed intensity map that maps predicted weed intensity values to different geographic locations in the field. In such an example, a map of the weed intensities at time of spraying is geo-referenced recorded and provided to agricultural harvester 100 as a prior information map 258 of weed intensity. In-situ sensors 208 can detect weed intensity at geographic locations in the field and predictive model generator 210 may then build a predictive model that models a relationship between weed intensity at time of harvest and weed intensity at time of spraying. This is because the sprayer will have impacted the weed intensity at time of spraying, but weeds may still crop up in similar areas again by harvest. However, the weed areas at harvest are likely to have different intensity based on timing of the harvest, weather, weed type, among other things.

In some examples, predictive map 264 can be provided to the control zone generator 213. Control zone generator 213 groups adjacent portions of an area into one or more control zones based on data values of predictive map 264 that are associated with those adjacent portions. A control zone may include two or more contiguous portions of an area, such as a field, for which a control parameter corresponding to the control zone for controlling a controllable subsystem is constant. For example, a response time to alter a setting of controllable subsystems 216 may be inadequate to satisfactorily respond to changes in values contained in a map, such as predictive map 264. In that case, control zone generator 213 parses the map and identifies control zones that are of a defined size to accommodate the response time of the controllable subsystems 216. In another example, control zones may be sized to reduce wear from excessive actuator movement resulting from continuous adjustment. In some examples, there may be a different set of control zones for each controllable subsystem 216 or for groups of controllable subsystems 216. The control zones may be added to the predictive map 264 to obtain predictive control zone map 265. Predictive control zone map 265 can thus be similar to predictive map 264 except that predictive control zone map 265 includes control zone information defining the control zones. Thus, a functional predictive map 263, as described herein, may or may not include control zones. Both predictive map 264 and predictive control zone map 265 are functional predictive maps 263. In one example, a functional predictive map 263 does not include control zones, such as predictive map 264. In another example, a functional predictive map 263 does include control zones, such as predictive control zone map 265. In some examples, multiple crops may be simultaneously present in a field if an intercrop production system is implemented. In that case, predictive map generator 212 and control zone generator 213 are able to identify the location and characteristics of the two or more crops and then generate predictive map 264 and predictive control zone map 265 accordingly.

It will also be appreciated that control zone generator 213 can cluster values to generate control zones and the control zones can be added to predictive control zone map 265, or a separate map, showing only the control zones that are generated. In some examples, the control zones may be used for controlling or calibrating agricultural harvester 100 or both. In other examples, the control zones may be presented to the operator 260 and used to control or calibrate agricultural harvester 100, and, in other examples, the control zones may be presented to the operator 260 or another user or stored for later use.

Predictive map 264 or predictive control zone map 265 or both are provided to control system 214, which generates control signals based upon the predictive map 264 or predictive control zone map 265 or both. In some examples, communication system controller controls communication system 206 to communicate the predictive map 264 or predictive control zone map 265 or control signals based on the predictive map 264 or predictive control zone map 265 to other agricultural harvesters that are harvesting in the same field. In some examples, communication system controller 229 controls the communication system 206 to send the predictive map 264, predictive control zone map 265, or both to other remote systems.

Operator interface controller 231 is operable to generate control signals to control operator interface mechanisms 218. The operator interface controller 231 is also operable to present the predictive map 264 or predictive control zone map 265 or other information derived from or based on the predictive map 264, predictive control zone map 265, or both to operator 260. Operator 260 may be a local operator or a remote operator. As an example, controller 231 generates control signals to control a display mechanism to display one or both of predictive map and predictive control zone map 265 for the operator 260. Controller 231 may generate operator actuatable mechanisms that are displayed and can be actuated by the operator to interact with the displayed map. The operator can edit the map by, for example, correcting a biomass displayed on the map, based on the operator's observation. Settings controller 232 can generate control signals to control various settings on the agricultural harvester 100 based upon predictive map 264, the predictive control zone map 265, or both. For instance, settings controller 232 can generate control signals to control machine and header actuators 248. In response to the generated control signals, the machine and header actuators 248 operate to control, for example, one or more of the sieve and chaffer settings, concave clearance, rotor settings, cleaning fan speed settings, header height, header functionality, reel speed, reel position, draper functionality (where agricultural harvester 100 is coupled to a draper header), corn header functionality, internal distribution control and other actuators 248 that affect the other functions of the agricultural harvester 100. Path planning controller 234 illustratively generates control signals to control steering subsystem 252 to steer agricultural harvester 100 according to a desired path. Path planning controller 234 can control a path planning system to generate a route for agricultural harvester 100 and can control propulsion subsystem 250 and steering subsystem 252 to steer agricultural harvester 100 along that route. Feed rate controller 236 can control various subsystems, such as propulsion subsystem 250 and machine actuators 248, to control a feed rate (throughput) based upon the predictive map 264 or predictive control zone map 265 or both. For instance, as agricultural harvester 100 approaches an upcoming area of crop on the field having a biomass value above a selected threshold, feed rate controller 236 may reduce the speed of machine 100 to maintain constant feed rate of biomass through the machine. Header and reel controller 238 can generate control signals to control a header or a reel or other header functionality. Draper belt controller 240 can generate control signals to control a draper belt or other draper functionality based upon the predictive map 264, predictive control zone map 265, or both. Deck plate position controller 242 can generate control signals to control a position of a deck plate included on a header based on predictive map 264 or predictive control zone map 265 or both, and residue system controller 244 can generate control signals to control a residue subsystem 138 based upon predictive map 264 or predictive control zone map 265, or both. Machine cleaning controller 245 can generate control signals to control machine cleaning subsystem 254. For instance, based upon the different types of seeds or weeds passed through machine 100, a particular type of machine cleaning operation or a frequency with which a cleaning operation is performed may be controlled. Other controllers included on the agricultural harvester 100 can control other subsystems based on the predictive map 264 or predictive control zone map 265 or both as well.

FIGS. 3A and 3B (collectively referred to herein as FIG. 3) show a flow diagram illustrating one example of the operation of agricultural harvester 100 in generating a predictive map 264 and predictive control zone map 265 based upon prior information map 258.

At 280, agricultural harvester 100 receives prior information map 258. Examples of prior information map 258 or receiving prior information map 258 are discussed with respect to blocks 281, 282, 284 and 286. As discussed above, prior information map 258 maps values of a variable, corresponding to a first characteristic, to different locations in the field, as indicated at block 282. As indicated at block 281, receiving the prior information map 258 may involve selecting one or more of a plurality of possible prior information maps that are available. For instance, one prior information map may be a vegetative index map generated from aerial imagery. Another prior information map may be a map generated during a prior pass through the field which may have been performed by a different machine performing a previous operation in the field, such as a sprayer or other machine. The process by which one or more prior information maps are selected can be manual, semi-automated, or automated. The prior information map 258 is based on data collected prior to a current harvesting operation. This is indicated by block 284. For instance, the data may be collected based on aerial images taken during a previous year, or earlier in the current growing season, or at other times.

The data used in the generation of prior information map 258 may be obtained in ways other than aerial imaging. For instance, agricultural harvester 100 may be fitted with a sensor, such as a perception sensor (e.g., forward looking image capture mechanism 151), that identifies vegetation characteristics such as vegetation height, vegetation density, vegetation mass, or vegetation volume, during a prior operation. In other instances, other vegetation characteristics may be identified and used. In another example, agricultural harvester 100 may be fitted with a sensor that senses a force, or an indication of force, used to drive threshing rotor 112, such as a pressure sensor that senses the fluid pressure used to drive threshing rotor 112 or a torque sensor that senses a torque used to drive threshing rotor 112, as the threshing rotor 112 processes crops harvested by agricultural harvester 100 during a prior operation. The data detected by the sensors during a previous year's harvest may be used as data to generate the prior information map 258. The sensed data may be combined with other data to generate the prior information map 258. For example, based upon a vegetation height, vegetation density, vegetation mass, or vegetation volume of the vegetation being harvested or encountered by agricultural harvester 100 at different locations in the field, and based upon other factors, such as vegetation type; the weather conditions, such as the weather conditions during the vegetation's growth; or soil characteristics, such as moisture, the biomass can be predicted so that the prior information map 258 maps the predicted biomass in the field. The data for the prior information map 258 can be transmitted to agricultural harvester 100 using communication system 206 and stored in data store 202. The data for the prior information map 258 can be provided to agricultural harvester 100 using communication system 206 in other ways as well, and this is indicated by block 286 in the flow diagram of FIG. 3. In some examples, the prior information map 258 can be received by communication system 206.

Upon commencement of a harvesting operation, in-situ sensors 208 generate sensor signals indicative of one or more in-situ data values indicative of a characteristic, for example, a vegetation characteristic, such as biomass or a biomass characteristic, as indicated by block 288. Examples of in-situ sensors 208 are discussed with respect to blocks 222, 290, and 226. As explained above, the in-situ sensors 208 include on-board sensors 222; remote in-situ sensors 224, such as UAV-based sensors flown at a time to gather in-situ data, shown in block 290; or other types of in-situ sensors, designated by in-situ sensors 226. In some examples, data from on-board sensors is georeferenced using position, heading, or speed data from geographic position sensor 204.

Predictive model generator 210 controls the prior information variable-to-in-situ variable model generator 228 to generate a model that models a relationship between the mapped values contained in the prior information map 258 and the in-situ values sensed by the in-situ sensors 208 as indicated by block 292. The characteristics or data types represented by the mapped values in the prior information map 258 and the in-situ values sensed by the in-situ sensors 208 may be the same characteristics or data type or different characteristics or data types.

The relationship or model generated by predictive model generator 210 is provided to predictive map generator 212. Predictive map generator 212 generates a predictive map 264 that predicts a value of the characteristic sensed by the in-situ sensors 208 at different geographic locations in a field being harvested, or a different characteristic that is related to the characteristic sensed by the in-situ sensors 208, using the predictive model and the prior information map 258, as indicated by block 294.

It should be noted that, in some examples, the prior information map 258 may include two or more different maps or two or more different map layers of a single map. Each map layer may represent a different data type from the data type of another map layer or the map layers may have the same data type that were obtained at different times. Each map in the two or more different maps or each layer in the two or more different map layers of a map maps a different type of variable to the geographic locations in the field. In such an example, predictive model generator 210 generates a predictive model that models the relationship between the in-situ data and each of the different variables mapped by the two or more different maps or the two or more different map layers. Similarly, in-situ sensors 208 can include two or more sensors each sensing a different type of variable. Thus, the predictive model generator 210 generates a predictive model that models the relationships between each type of variable mapped by the prior information map 258 and each type of variable sensed by the in-situ sensors 208. Predictive map generator 212 can generate a functional predictive map 263 that predicts a value for each sensed characteristic sensed by the in-situ sensors 208 (or a characteristic related to the sensed characteristic) at different locations in the field being harvested using the predictive model and each of the maps or map layers in the prior information map 258.

Predictive map generator 212 configures the predictive map 264 so that the predictive map 264 is actionable (or consumable) by control system 214. Predictive map generator 212 can provide the predictive map 264 to the control system 214 or to control zone generator 213 or both. Some examples of different ways in which the predictive map 264 can be configured or output are described with respect to blocks 296, 295, 299 and 297. For instance, predictive map generator 212 configures predictive map 264 so that predictive map 264 includes values that can be read by control system 214 and used as the basis for generating control signals for one or more of the different controllable subsystems of the agricultural harvester 100, as indicated by block 296.

Control zone generator 213 can divide the predictive map 264 into control zones based on the values on the predictive map 264. Contiguously-geolocated values that are within a threshold value of one another can be grouped into a control zone. The threshold value can be a default threshold value, or the threshold value can be set based on an operator input, based on an input from an automated system, or based on other criteria. A size of the zones may be based on a responsiveness of the control system 214, the controllable subsystems 216, based on wear considerations, or on other criteria as indicated by block 295. Predictive map generator 212 configures predictive map 264 for presentation to an operator or other user. Control zone generator 213 can configure predictive control zone map 265 for presentation to an operator or other user. This is indicated by block 299. When presented to an operator or other user, the presentation of the predictive map 264 or predictive control zone map 265 or both may contain one or more of the predictive values on the predictive map 264 correlated to geographic location, the control zones on predictive control zone map 265 correlated to geographic location, and settings values or control parameters that are used based on the predicted values on predictive map 264 or zones on predictive control zone map 265. The presentation can, in another example, include more abstracted information or more detailed information. The presentation can also include a confidence level that indicates an accuracy with which the predictive values on predictive map 264 or the zones on predictive control zone map 265 conform to measured values that may be measured by sensors on agricultural harvester 100 as agricultural harvester 100 moves through the field. Further where information is presented to more than one location, an authentication and authorization system can be provided to implement authentication and authorization processes. For instance, there may be a hierarchy of individuals that are authorized to view and change maps and other presented information. By way of example, an on-board display device may show the maps in near real time locally on the machine, or the maps may also be generated at one or more remote locations, or both. In some examples, each physical display device at each location may be associated with a person or a user permission level. The user permission level may be used to determine which display markers are visible on the physical display device and which values the corresponding person may change. As an example, a local operator of agricultural harvester 100 may be unable to see the information corresponding to the predictive map 264 or make any changes to machine operation. A supervisor, such as a supervisor at a remote location, however, may be able to see the predictive map 264 on the display but be prevented from making any changes. A manager, who may be at a separate remote location, may be able to see all of the elements on predictive map 264 and also be able to change the predictive map 264. In some instances, the predictive map 264 accessible and changeable by a manager located remotely may be used in machine control. This is one example of an authorization hierarchy that may be implemented. The predictive map 264 or predictive control zone map 265 or both can be configured in other ways as well, as indicated by block 297.

At block 298, input from geographic position sensor 204 and other in-situ sensors 208 are received by the control system. Particularly, at block 300, control system 214 detects an input from the geographic position sensor 204 identifying a geographic location of agricultural harvester 100. Block 302 represents receipt by the control system 214 of sensor inputs indicative of trajectory or heading of agricultural harvester 100, and block 304 represents receipt by the control system 214 of a speed of agricultural harvester 100. Block 306 represents receipt by the control system 214 of other information from various in-situ sensors 208.

At block 308, control system 214 generates control signals to control the controllable subsystems 216 based on the predictive map 264 or predictive control zone map 265 or both and the input from the geographic position sensor 204 and any other in-situ sensors 208. At block 310, control system 214 applies the control signals to the controllable subsystems. It will be appreciated that the particular control signals that are generated, and the particular controllable subsystems 216 that are controlled, may vary based upon one or more different things. For example, the control signals that are generated and the controllable subsystems 216 that are controlled may be based on the type of predictive map 264 or predictive control zone map 265 or both that is being used. Similarly, the control signals that are generated and the controllable subsystems 216 that are controlled and the timing of the control signals can be based on various latencies of crop flow through the agricultural harvester 100 and the responsiveness of the controllable subsystems 216.

By way of example, a generated predictive map 264 in the form of a predictive biomass map can be used to control one or more subsystems 216. For instance, the predictive biomass map can include biomass or biomass characteristic values georeferenced to locations within the field being harvested. The biomass or biomass characteristic values from the predictive biomass map can be extracted and used to control, for example, the steering and propulsion subsystems 252 and 250. By controlling the steering and propulsion subsystems 252 and 250, a feed rate of material moving through the agricultural harvester 100 can be controlled. Similarly, the header height can be controlled to take in more or less material, and, thus, the header height can also be controlled to control feed rate of material through the agricultural harvester 100. In other examples, if the predictive map 264 maps a biomass forward of agricultural harvester 100 being greater along one portion of header 102 than another portion of header 102, resulting in a different biomass entering one side of header 102 than the other side of header 102, control of header 102 may be implemented. For example, a draper speed on one side of header 102 may be increased or decreased relative to the draper speed on the other side of header 102 to account for the difference in biomass. Thus, draper belt controller 240 can be used, based on georeferenced values present in the predictive biomass map, to control draper speeds of the draper belts on header 102. The preceding example involving biomass and using a predictive biomass map is provided merely as an example. Consequently, a wide variety of other control signals can be generated using values obtained from a predictive biomass map or other type of predictive map to control one or more of the controllable subsystems 216.

At block 312, a determination is made as to whether the harvesting operation has been completed. If harvesting is not completed, the processing advances to block 314 where in-situ sensor data from geographic position sensor 204 and in-situ sensors 208 (and perhaps other sensors) continue to be read.

In some examples, at block 316, agricultural harvester 100 can also detect learning trigger criteria to perform machine learning on one or more of the predictive map 264, predictive control zone map 265, the model generated by predictive model generator 210, the zones generated by control zone generator 213, one or more control algorithms implemented by the controllers in the control system 214, and other triggered learning.

The learning trigger criteria can include any of a wide variety of different criteria. Some examples of detecting trigger criteria are discussed with respect to blocks 318, 320, 321, 322 and 324. For instance, in some examples, triggered learning can involve recreation of a relationship used to generate a predictive model when a threshold amount of in-situ sensor data are obtained from in-situ sensors 208. In such examples, receipt of an amount of in-situ sensor data from the in-situ sensors 208 that exceeds a threshold triggers or causes the predictive model generator 210 to generate a new predictive model that is used by predictive map generator 212. Thus, as agricultural harvester 100 continues a harvesting operation, receipt of the threshold amount of in-situ sensor data from the in-situ sensors 208 triggers the creation of a new relationship represented by a predictive model generated by predictive model generator 210. Further, new predictive map 264, predictive control zone map 265, or both can be regenerated using the new predictive model. Block 318 represents detecting a threshold amount of in-situ sensor data used to trigger creation of a new predictive model.

In other examples, the learning trigger criteria may be based on how much the in-situ sensor data from the in-situ sensors 208 are changing, such as over time or compared to previous values. For example, if variations within the in-situ sensor data (or the relationship between the in-situ sensor data and the information in prior information map 258) are within a selected range or is less than a defined amount, or below a threshold value, then a new predictive model is not generated by the predictive model generator 210. As a result, the predictive map generator 212 does not generate a new predictive map 264, predictive control zone map 265, or both. However, if variations within the in-situ sensor data are outside of the selected range, are greater than the defined amount, or are above the threshold value, for example, then the predictive model generator 210 generates a new predictive model using all or a portion of the newly received in-situ sensor data that the predictive map generator 212 uses to generate a new predictive map 264. At block 320, variations in the in-situ sensor data, such as a magnitude of an amount by which the data exceeds the selected range or a magnitude of the variation of the relationship between the in-situ sensor data and the information in the prior information map 258, can be used as a trigger to cause generation of a new predictive model and predictive map. Keeping with the examples described above, the threshold, the range, and the defined amount can be set to default values; set by an operator or user interaction through a user interface; set by an automated system; or set in other ways.

Other learning trigger criteria can also be used. For instance, if predictive model generator 210 switches to a different prior information map (different from the originally selected prior information map 258), then switching to the different prior information map may trigger re-learning by predictive model generator 210, predictive map generator 212, control zone generator 213, control system 214, or other items. In another example, transitioning of agricultural harvester 100 to a different topography or to a different control zone may be used as learning trigger criteria as well.

In some instances, operator 260 can also edit the predictive map 264 or predictive control zone map 265 or both. The edits can change a value on the predictive map 264, change a size, shape, position, or existence of a control zone on predictive control zone map 265, or both. Block 321 shows that edited information can be used as learning trigger criteria.

In some instances, it may also be that operator 260 observes that automated control of a controllable subsystem, is not what the operator desires. In such instances, the operator 260 may provide a manual adjustment to the controllable subsystem reflecting that the operator 260 desires the controllable subsystem to operate in a different way than is being commanded by control system 214. Thus, manual alteration of a setting by the operator 260 can cause one or more of predictive model generator 210 to relearn a model, predictive map generator 212 to regenerate map 264, control zone generator 213 to regenerate one or more control zones on predictive control zone map 265, and control system 214 to relearn a control algorithm or to perform machine learning on one or more of the controller components 232 through 246 in control system 214 based upon the adjustment by the operator 260, as shown in block 322. Block 324 represents the use of other triggered learning criteria.

In other examples, relearning may be performed periodically or intermittently based, for example, upon a selected time interval such as a discrete time interval or a variable time interval, as indicated by block 326.

If relearning is triggered, whether based upon learning trigger criteria or based upon passage of a time interval, as indicated by block 326, then one or more of the predictive model generator 210, predictive map generator 212, control zone generator 213, and control system 214 performs machine learning to generate a new predictive model, a new predictive map, a new control zone, and a new control algorithm, respectively, based upon the learning trigger criteria. The new predictive model, the new predictive map, and the new control algorithm are generated using any additional data that has been collected since the last learning operation was performed. Performing relearning is indicated by block 328.

If the harvesting operation has been completed, operation moves from block 312 to block 330 where one or more of the predictive map 264, predictive control zone map 265, and predictive model generated by predictive model generator 210 are stored. The predictive map 264, predictive control zone map 265, and predictive model may be stored locally on data store 202 or sent to a remote system using communication system 206 for later use.

It will be noted that while some examples herein describe predictive model generator 210 and predictive map generator 212 receiving a prior information map in generating a predictive model and a functional predictive map, respectively, in other examples, the predictive model generator 210 and predictive map generator 212 can receive, in generating a predictive model and a functional predictive map, respectively other types of maps, including predictive maps, such as a functional predictive map generated during the harvesting operation.

FIG. 4 is a block diagram of a portion of the agricultural harvester 100 shown in FIG. 1. Particularly, FIG. 4 shows, among other things, examples of the predictive model generator 210 and the predictive map generator 212 in more detail. FIG. 4 also illustrates information flow among the various components shown. The predictive model generator 210 receives a vegetative index map 332 as a prior information map. Predictive model generator 210 also receives a geographic location 334, or an indication of a geographic location, from geographic position sensor 204. In-situ sensors 208 illustratively include a biomass sensor, such as biomass sensor 336, as well as a processing system 338. In some instances, biomass sensor 336 may be located on-board of the agricultural harvester 100. The processing system 338 processes sensor data generated from on-board biomass sensor 336 to generate processed data, some examples of which are described below.

In some examples, biomass sensor 336 may be an optical sensor, such as a camera, a stereo camera, a mono camera, lidar, or radar, that generates images of an area of a field to be harvested. In some instances, the optical sensor may be arranged on the agricultural harvester 100, or a header attached to the agricultural harvester 100, to collect images of an area adjacent to the agricultural harvester 100, such as in an area that lies in front of, to the side of, rearwardly of, or in another direction relative to the agricultural harvester 100 as agricultural harvester 100 moves through the field during a harvesting operation. The optical sensor may also be located on or inside of the agricultural harvester 100 to obtain images of one or more portions of the exterior or interior of the agricultural harvester 100. Processing system 338 processes one or more images obtained via the biomass sensor 336 to generate processed image data identifying one or more characteristics of crops in the image. Vegetation characteristics detected by the processing system 338 may include a height of vegetation present in the image, a volume of vegetation in an image, a mass of vegetation present in the image, or a density of crop in the image. In another example, biomass sensor 336 may be a force sensor that generates sensor signals indicative of a force, such as a fluid pressure or a torque, used to drive threshing rotor 112 of agricultural harvester 100 to indicate a biomass being processed by agricultural harvester 100 during the course of a harvesting operation.

In-situ sensor 208 may be or include other types of sensors, such as a camera located along a path by which severed vegetation material travels in agricultural harvester 100 (referred to hereinafter as "process camera"). A process camera may be located internal to the agricultural harvester 100 and may capture images of vegetation material as the vegetation material moves through or is expelled from the agricultural harvester 100. For instance, a process camera may be configured to detect vegetation material coming through the feeder house of agricultural harvester 100. Process cameras may obtain images of severed vegetation material, and image processing system 338 is operable to detect the biomass or biomass characteristics of the vegetation material as it moves through or is expelled from agricultural harvester 100. In other examples, in-situ sensor 208 may include a material distribution sensor that measures the volume or mass of material at two or more locations. The measurements may be absolute or relative. In some examples, electromagnetic or ultrasonic sensors may be used to measure time of flight, phase shift, or binocular disparities of one or more signals reflected by material surfaces at distances relative to a reference surface. In other examples, emitted signal or subatomic particle backscatter, absorption, attenuation, or transmission may be used to measure the material distribution. In other example, material properties, such as electrical permittivity, may be used to measure the distribution. Other approaches may be used as well. It will be noted that these are merely some examples of in-situ sensor 208 or biomass sensor 336, or both, and that various other sensors may be used.

In other examples, biomass sensor 336 can rely on wavelength(s) of electromagnetic energy, and the way the electromagnetic energy is reflected by, absorbed by, attenuated by, or transmitted through vegetation. The biomass sensor 336 may sense other electromagnetic properties of vegetation, such as electrical permittivity, when the severed vegetation material passes between two capacitive plates. The biomass sensor 336 may also rely on mechanical properties of vegetation, such as a signal generated when a portion of the vegetation (e.g., grain) impacts a piezoelectric sheet or when an impact by a portion of the vegetation is detected by a microphone or accelerometer. Other material properties and sensors may also be used. In some examples, biomass sensor 336 may be an ultrasonic sensor, a capacitive sensor, an electrical permittivity sensor, or a mechanical sensor, that senses vegetation inside or outside of agricultural harvester 100. In some examples, biomass sensor 336 may be a light attenuation sensor or a reflectance sensor. In some examples, raw or processed data from biomass sensor 336 may be presented to operator 260 via operator interface mechanism 218. Operator 260 may be on-board the agricultural harvester 100 or at a remote location. The processing system 338 is operable to detect the biomass being harvested by agricultural harvester 100, as well as various biomass characteristics of the vegetation, such as vegetation height, vegetation volume, vegetation mass, or vegetation density, corresponding to the vegetation being encountered by the agricultural harvester 100 during the course of a harvesting operation.

The present discussion proceeds with respect to an example in which biomass sensor 336 senses biomass or a biomass characteristic, such as an optical sensor that generates an image indicative of biomass or a biomass characteristic, or in which the biomass sensor 336 is a force sensor, such as a pressure sensor or torque sensor, that senses a force used to drive threshing rotor 112 as an indication of biomass. It will be appreciated that these are just some examples, and the sensors mentioned above, as well as other examples of biomass sensor 336, are contemplated herein as well. As shown in FIG. 4, the example predictive model generator 210 includes one or more of a vegetation height-to-vegetative index model generator 342, a vegetation density-to-vegetative index model generator 344, a vegetation mass-to-vegetative index model generator 345, a vegetation volume-to-vegetative index model generator 346, and a threshing rotor drive force-to-vegetative index model generator 347. In other examples, the predictive model generator 210 may include additional, fewer, or different components than those shown in the example of FIG. 4. Consequently, in some examples, the predictive model generator 210 may include other items 348 as well, which may include other types of predictive model generators to generate other types of vegetation characteristic models, for example, other characteristics indicative of biomass-to-vegetative index model generators. In some examples, the model generators 342, 344, 345, and 346 may also include, as the vegetation characteristic, crop characteristics, such as crop height, crop density, crop mass, and crop volume. In other examples, predictive model generator may include one or more of a crop height-to-vegetative index model generator, a crop density-to-vegetative index model generator, a crop mass-to-vegetative index model generator, or a crop volume-to-vegetative index model generator.

Vegetation height-to-vegetative index model generator 342 identifies a relationship between vegetation height detected in processed data 340, at a geographic location corresponding to the processed data 340, and vegetative index values from the vegetative index map 332 corresponding to the same location in the field where the vegetation height corresponds. Based on the relationship established by vegetation height-to-vegetative index model generator 342, vegetation height-to-vegetative index model generator 342 generates a predictive biomass model. The predictive biomass model is used by vegetation height map generator 352 to predict, at any given location in the field, vegetation height at that location in the field, based upon a georeferenced vegetative index value contained in the vegetative index map 332, corresponding to that location in the field.

Vegetation density-to-vegetative index model generator 344 identifies a relationship between a vegetation density level represented in the processed data 340, at a geographic location corresponding to the processed data 340, and the vegetative index value corresponding to the same geographic location. Again, the vegetative index value is the georeferenced value contained in the vegetative index map 332. Based on the relationship established by vegetation density-to-vegetative index model generator 344, vegetation density-to-vegetative index model generator 344 generates a predictive biomass model. The predictive biomass model is used by vegetation density map generator 354 to predict, at any given location in the field, the vegetation density at that location in the field, based upon a georeferenced vegetative index value contained in the vegetative index map 332, corresponding to that location in the field.

Vegetation mass-to-vegetative index model generator 345 identifies a relationship between the vegetation mass represented in the processed data 340, at a geographic location in the field corresponding to the processed data 340, and the vegetative index value from the vegetative index map 332 corresponding to the same location. Based on the relationship established by vegetation mass-to-vegetative index model generator 345, vegetation mass-to-vegetative index model generator 345 generates a predictive biomass model. The predictive biomass model is used by vegetation mass map generator 355 to predict, at any given location in the field, vegetation mass at that location in the field, based upon a georeferenced vegetative index value contained in the vegetative index map 332, corresponding to that location in the field.

Vegetation volume-to-vegetative index model generator 346 identifies a relationship between the vegetation volume represented in the processed data 340, at a geographic location in the field corresponding to the processed data 340, and the vegetative index value from the vegetative index map 332 corresponding to that same location. Based on the relationship established by vegetation volume-to-vegetative index model generator 346, vegetation volume-to-vegetative index model generator 346 generates a predictive biomass model. The predictive biomass model is used by vegetation volume map generator 356 to predict, at any given location in the field, the vegetation volume at that location in the field, based upon a georeferenced vegetative index value contained in the vegetative index map 332, corresponding to that location in the field.

Threshing rotor drive force-to-vegetative index model generator 347 identifies a relationship between the threshing rotor drive force represented in the processed data 340, at a geographic location in the field corresponding to the processed data, and the vegetative index value from the vegetative index map 332 corresponding to that same location. Based on the relationship established by threshing rotor drive force-to-vegetative index model generator 347, threshing rotor drive force-to-vegetative index model generator 347 generates a predictive biomass model. The predictive biomass model is used by threshing rotor drive force map generator 357 to predict, at any given location in the field, the threshing rotor drive force at that location in the field, based upon a georeferenced vegetative index value contained in the vegetative index map 332, corresponding to that location in the field.

In light of the above, the predictive model generator 210 is operable to produce a plurality of predictive biomass models, such as one or more of the predictive biomass models generated by model generators 342, 344, 345, 346, 347, and 348. In another example, two or more of the predictive biomass models described above may be combined into a single predictive biomass model that predicts two or more biomass characteristics, such as vegetation height (e.g., crop height, weed height, etc.), vegetation density (e.g., crop density, weed density, etc.), vegetation mass (e.g., crop mass, weed mass, etc.), vegetation volume (e.g., crop volume, weed volume, etc.), or threshing rotor drive force, based upon the vegetative index value at different locations in the field. Any of these biomass models, or combinations thereof, are represented collectively by predictive biomass model 350 in FIG. 4.

The predictive biomass model 350 is provided to predictive map generator 212. In the example of FIG. 4, predictive map generator 212 includes a vegetation height map generator 352, a vegetation density map generator 354, a vegetation mass map generator 355, a vegetation volume map generator 356, and a threshing rotor drive force map generator 357. In other examples, the predictive map generator 212 may include additional, fewer, or different map generators. Thus, in some examples, the predictive map generator 212 may include other items 358 which may include other types of map generators to generate biomass maps for other types of characteristics. For example, predictive map generator 212 may include one or more of a crop height map generator, a crop density map generator, a crop mass map generator, or a crop volume generator. Additionally, in other examples, map generators 352, 354, 355, or 356 may map, as vegetation characteristics, crop characteristics such as crop height, crop density, crop mass, or crop volume. Vegetation height map generator 352 receives the predictive biomass model 350 and generates a predictive map that predicts the vegetation height at different locations in the field, based on the predictive biomass model 350 and based on the vegetative index values contained in the vegetative index map 332 at those locations in the field.

Vegetation density map generator 354 receives the predictive biomass model 350 and generates a predictive map that predicts the vegetation density at different locations in the field based upon the predictive biomass model 350 and the vegetative index values, contained in the vegetative index map 332, at those locations in the field. Vegetation mass map generator 355 receives the predictive biomass model 350 and generates a predictive map that predicts vegetation mass at different locations in the field based upon the predictive biomass model 350 and based on the vegetative index value contained in the vegetative index map 332 at those locations in the field.

Vegetation volume map generator 356 receives the predictive biomass model 350 and generates a predictive map that predicts vegetation volume at different locations in the field based upon the predictive biomass model 350 and based on the vegetative index values contained in the vegetative index map 332 at those locations in the field. Threshing rotor drive force map generator 357 receives the predictive biomass model 350 and generates a predictive map that predicts threshing rotor drive force at different locations in the field based upon the predictive biomass model 350 and based on the vegetative index values contained in the vegetative index map 332 at those locations in the field. Other map generator 358 can generate a predictive map that predicts other characteristics, such as crop characteristics, for instance, crop height, crop density, crop mass, or crop volume, at different locations in the field based upon the vegetative index values at those locations in the field and the predictive biomass model 350.

Predictive map generator 212 outputs one or more predictive biomass maps 360 that are predictive of biomass or biomass characteristic values at different geographic locations across the field. In one example, the one or more predictive biomass maps 360 predicts one or more of vegetation height, vegetation density, vegetation mass, vegetation volume, or threshing rotor drive force. In another example, the one or more predictive biomass maps 360 predicts one or more of crop height, crop density, crop mass, or crop volume. In other examples, vegetation height, vegetation density, vegetation mass, or vegetation volume may include indications of crop height, crop density, crop mass, or crop volume, respectively. Each of the predictive biomass maps 360 predicts the respective characteristic at different locations in a field. Each of the generated predictive biomass maps 360 may be provided to control zone generator 213, control system 214, or both. Control zone generator 213 generates control zones and incorporates those control zones into the functional predictive map, i.e., predictive biomass map 360, to provide functional predictive biomass map 360 with control zones. predictive map 264 Functional predictive biomass map 360 (with or without control zones) may be provided to control system 214, which generates control signals to control one or more of the controllable subsystems 216 based upon the functional predictive biomass map 360 (with or without control zones). 264, predictive control zone map 265, or both.

FIG. 5 is a flow diagram of an example of operation of predictive model generator 210 and predictive map generator 212 in generating the predictive biomass model 350 and the predictive biomass map 360, respectively. At block 362, predictive model generator 210 and predictive map generator 212 receive a prior vegetative index map 332. At block 364, processing system 338 receives one or more sensor signals from in-situ sensors 208, such as biomass sensor 336. As discussed above, the in-situ sensor 208, such as biomass sensor 336, may be an optical sensor 368, such as a camera (e.g., a forward looking camera), lidar, radar, or another optical sensing device looking internally to or externally of a combine harvester; a threshing rotor drive force sensor 369, such as a pressure sensor that senses a fluid pressure used to drive the threshing rotor or a torque sensor that senses a torque used to drive threshing rotor. Still further, other types of in-situ sensors, such as another type of biomass sensor, as indicated by block 370, are within the scope of the present disclosure.

At block 372, processing system 338 processes the one or more received sensor signals to generate sensor data indicative of a characteristic of biomass sensed by the in-situ sensor 208, such as biomass sensor 336. At block 374, the sensor data may be indicative of vegetation height, such as crop height, that may exist at a location, such as at a location in front of a combine harvester. In some instances, as indicated at block 376, the sensor data may be indicative of density of vegetation, such as a density of crops in front of agricultural harvester 100. In some instances, as indicated by block 377, the sensor data may be indicative of vegetation mass, such as a mass of the crop or a crop component, being processed by agricultural harvester 100. A crop component can include parts of the crop plant that comprise less than the entirety of the crop plant, for example, the stalk or stem, leaves, a head or an ear, a cob, a grain, oil, protein, water, or starch, and, thus, crop component mass can be the mass of a component of the crop plant, such as stalk mass, leaf mass, ear mass, grain mass, oil mass, protein mass, water mass, or starch mass, as well as mass of various other crop components. The mass of the crop component can be used as an indicator of biomass. In some instances, as indicated at block 378, the sensor data may be indicative of vegetation volume, such as a volume of crops in front of agricultural harvester 100. In some instances, as indicated by block 379, the sensor data may be indicative of threshing rotor drive force, such as a fluid pressure or torque used to drive threshing rotor 112 as agricultural harvester 100 processes vegetation material. The sensor data can include other data as well, as indicated by block 380.

At block 382, predictive model generator 210 obtains the geographic location corresponding to the sensor data. For instance, the predictive model generator 210 can obtain the geographic position from geographic position sensor 204 and determine, based upon machine delays, machine speed, etc., a precise geographic location where the sensor signal was generated or from which the sensor data 340 was derived. For instance, in the example in which the sensor data is indicative of a threshing rotor drive force, a time offset can be determined to identify the location on the field where the vegetation being processed by the threshing rotor was located, for example, based on location, heading, or speed data of the agricultural harvester 100. Thus, the threshing rotor drive force can be correlated to the appropriate location on the field.

At block 384, predictive model generator 210 generates one or more predictive biomass models, such as biomass model 350, that model a relationship between a vegetative index value obtained from a prior information map, such as prior information map 258, and a characteristic being sensed by the in-situ sensor 208 or a related characteristic. For instance, predictive model generator 210 may generate a predictive biomass model that models the relationship between a vegetative index value and a sensed characteristic including vegetation height, such as crop height, vegetation density, such as crop density, vegetation mass, such as crop mass or crop component mass, vegetation volume, such as crop volume, or threshing rotor drive force indicated by the sensor data obtained from in-situ sensor 208.

At block 386, the predictive biomass model, such as predictive biomass model 350, is provided to predictive map generator 212 which generates a predictive biomass map 360 that maps a predicted biomass value or a biomass characteristic value based on the vegetative index map and the predictive biomass model 350. For instance, in some examples, the predictive biomass map 360 predicts a biomass value, such as predicted biomass levels (e.g., high, medium, low) or more finite examples, such as weight (e.g., kilograms, pounds, etc.). In some examples, predictive biomass map 360 predicts a biomass characteristic value, such as predicted vegetation height, such as crop height, as indicated by block 387. In some examples, the predictive biomass map 360 predicts vegetation density, such as crop density, as indicated by block 388. In some examples, the predictive biomass map 360 predicts vegetation mass, such as crop mass or crop component mass, as indicated by block 389. In some examples, the predictive biomass map 360 predicts vegetation volume, such as crop volume, as indicated by block 390. In some examples, the predictive biomass map predicts threshing rotor drive force, as indicated by block 391, and, in still other examples, the predictive biomass map 360 predicts other items, as indicated by block 392. It should be noted that, at block 386, the predictive biomass map 360 can predict any number of combinations of characteristics together, for instance, vegetation height along with vegetation density, vegetation mass, vegetation volume, or threshing rotor drive force. Further, the predictive biomass map 360 can be generated during the course of an agricultural operation. Thus, as an agricultural harvester is moving through a field performing an agricultural operation, the predictive biomass map 360 is generated as the agricultural operation is being performed.

At block 394, predictive map generator 212 outputs the predictive biomass map 360. At block 391, predictive biomass map generator 212 outputs the predictive biomass map for presentation to and possible interaction by operator 260. At block 393, predictive map generator 212 may configure the predictive biomass map 360 for consumption by control system 214. At block 395, predictive map generator 212 can also provide the predictive biomass map 360 to control zone generator 213 for generation of control zones. At block 397, predictive map generator configures the predictive biomass map 360 in other ways as well. The predictive biomass map 360 (with or without the control zones) is provided to control system 214. At block 396, control system 214 generates control signals to control the controllable subsystems 216 based upon the predictive biomass map 360.

It can thus be seen that the present system takes a prior information map such as a prior information map that maps a characteristic, such as a vegetative index value, to different locations in a field or a prior information map that maps characteristic information generated during a prior operation to different locations in a field and uses one or more in-situ sensors that sense in-situ sensor data that is indicative of a characteristic, such as vegetation height, vegetation density, vegetation mass, vegetation volume, or threshing rotor drive force, and generates a model that models a relationship between the characteristic sensed using the in-situ sensor, or a related characteristic, and the characteristic mapped in the prior information map. Thus, the present system generates a functional predictive map using a model, in-situ data, and a prior information map and may configure the generated functional predictive map for consumption by a control system, for presentation to a local or remote operator or other user, or both. For example, the control system may use the map to control one or more systems of a combine harvester.

The present discussion has mentioned processors and servers. In some examples, the processors and servers include computer processors with associated memory and timing circuitry, not separately shown. The processors and servers are functional parts of the systems or devices to which the processors and servers belong and are activated by and facilitate the functionality of the other components or items in those systems.

Also, a number of user interface displays have been discussed. The displays can take a wide variety of different forms and can have a wide variety of different user actuatable operator interface mechanisms disposed thereon. For instance, user actuatable operator interface mechanisms may include text boxes, check boxes, icons, links, drop-down menus, search boxes, etc. The user actuatable operator interface mechanisms can also be actuated in a wide variety of different ways. For instance, the user actuatable operator interface mechanisms can be actuated using operator interface mechanisms such as a point and click device, such as a track ball or mouse, hardware buttons, switches, a joystick or keyboard, thumb switches or thumb pads, etc., a virtual keyboard or other virtual actuators. In addition, where the screen on which the user actuatable operator interface mechanisms are displayed is a touch sensitive screen, the user actuatable operator interface mechanisms can be actuated using touch gestures. Also, user actuatable operator interface mechanisms can be actuated using speech commands using speech recognition functionality. Speech recognition may be implemented using a speech detection device, such as a microphone, and software that functions to recognize detected speech and execute commands based on the received speech.

A number of data stores have also been discussed. It will be noted the data stores can each be broken into multiple data stores. In some examples, one or more of the data stores may be local to the systems accessing the data stores, one or more of the data stores may all be located remote form a system utilizing the data store, or one or more data stores may be local while others are remote. All of these configurations are contemplated by the present disclosure.

Also, the figures show a number of blocks with functionality ascribed to each block. It will be noted that fewer blocks can be used to illustrate that the functionality ascribed to multiple different blocks is performed by fewer components. Also, more blocks can be used illustrating that the functionality may be distributed among more components. In different examples, some functionality may be added, and some may be removed.

It will be noted that the above discussion has described a variety of different systems, components, logic, and interactions. It will be appreciated that any or all of such systems, components, logic and interactions may be implemented by hardware items, such as processors, memory, or other processing components, some of which are described below, that perform the functions associated with those systems, components, logic, or interactions. In addition, any or all of the systems, components, logic and interactions may be implemented by software that is loaded into a memory and is subsequently executed by a processor or server or other computing component, as described below. Any or all of the systems, components, logic and interactions may also be implemented by different combinations of hardware, software, firmware, etc., some examples of which are described below. These are some examples of different structures that may be used to implement any or all of the systems, components, logic and interactions described above. Other structures may be used as well.

Figure 6:
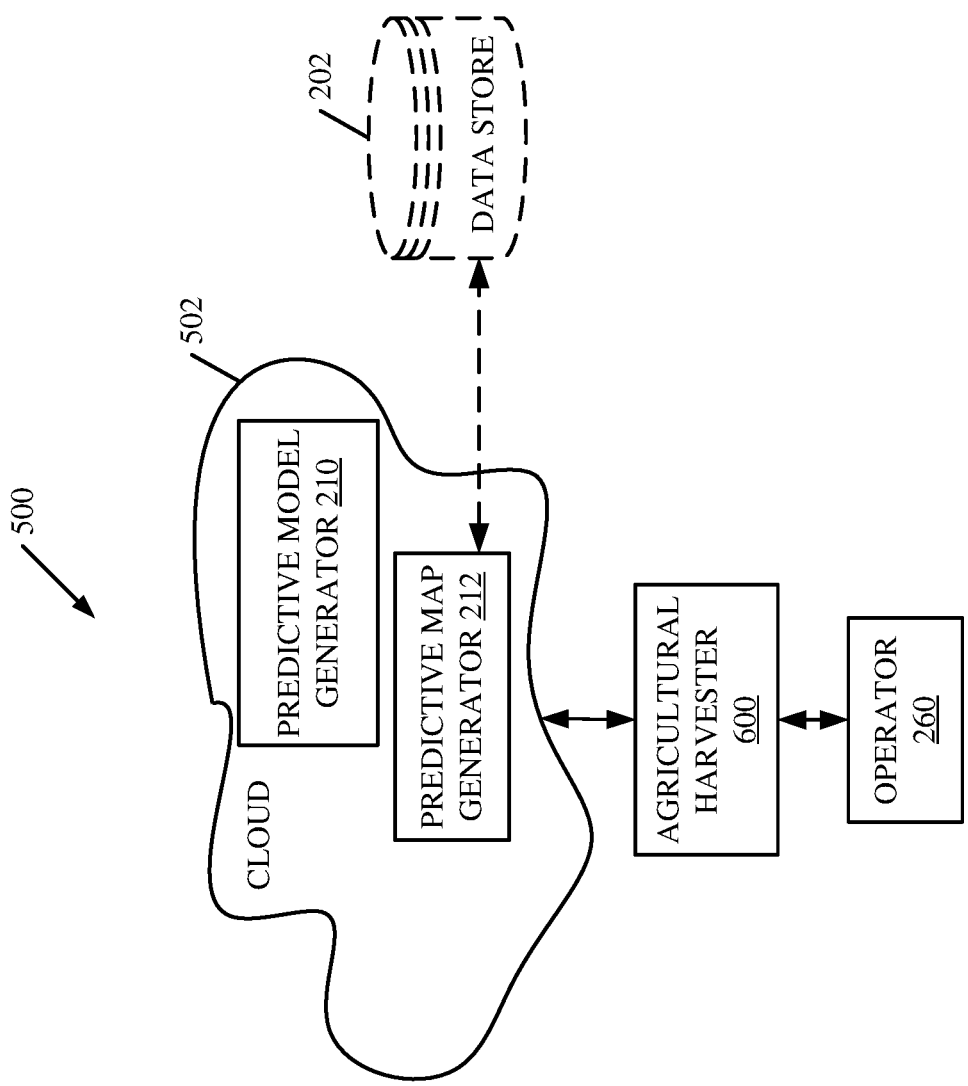
FIG. 6 is a block diagram showing one example of an agricultural harvester in communication with a remote server environment.

FIG. 6 is a block diagram of agricultural harvester 600, which may be similar to agricultural harvester 100 shown in FIG. 2. The agricultural harvester 600 communicates with elements in a remote server architecture 500. In some examples, remote server architecture 500 provides computation, software, data access, and storage services that do not require end-user knowledge of the physical location or configuration of the system that delivers the services. In various examples, remote servers may deliver the services over a wide area network, such as the internet, using appropriate protocols. For instance, remote servers may deliver applications over a wide area network and may be accessible through a web browser or any other computing component. Software or components shown in FIG. 2 as well as data associated therewith, may be stored on servers at a remote location. The computing resources in a remote server environment may be consolidated at a remote data center location, or the computing resources may be dispersed to a plurality of remote data centers. Remote server infrastructures may deliver services through shared data centers, even though the services appear as a single point of access for the user. Thus, the components and functions described herein may be provided from a remote server at a remote location using a remote server architecture. Alternatively, the components and functions may be provided from a server, or the components and functions can be installed on client devices directly, or in other ways.

In the example shown in FIG. 6, some items are similar to those shown in FIG. 2 and those items are similarly numbered. FIG. 6 specifically shows that predictive model generator or predictive map generator 212, or both, may be located at a server location 502 that is remote from the agricultural harvester 600. Therefore, in the example shown in FIG. 6, agricultural harvester 600 accesses systems through remote server location 502.

FIG. 6 also depicts another example of a remote server architecture. FIG. 6 shows that some elements of FIG. 2 may be disposed at a remote server location 502 while others may be located elsewhere. By way of example, data store 202 may be disposed at a location separate from location 502 and accessed via the remote server at location 502. Regardless of where the elements are located, the elements can be accessed directly by agricultural harvester 600 through a network such as a wide area network or a local area network; the elements can be hosted at a remote site by a service; or the elements can be provided as a service or accessed by a connection service that resides in a remote location. Also, data may be stored in any location, and the stored data may be accessed by, or forwarded to, operators, users, or systems. For instance, physical carriers may be used instead of, or in addition to, electromagnetic wave carriers. In some examples, where wireless telecommunication service coverage is poor or nonexistent, another machine, such as a fuel truck or other mobile machine or vehicle, may have an automated, semi-automated, or manual information collection system. As the combine harvester 600 comes close to the machine containing the information collection system, such as a fuel truck prior to fueling, the information collection system collects the information from the combine harvester 600 using any type of ad-hoc wireless connection. The collected information may then be forwarded to another network when the machine containing the received information reaches a location where wireless telecommunication service coverage or other wireless coverage is available. For instance, a fuel truck may enter an area having wireless communication coverage when traveling to a location to fuel other machines or when at a main fuel storage location. All of these architectures are contemplated herein. Further, the information may be stored on the agricultural harvester 600 until the agricultural harvester 600 enters an area having wireless communication coverage. The agricultural harvester 600, itself, may send the information to another network.

It will also be noted that the elements of FIG. 2, or portions thereof, may be disposed on a wide variety of different devices. One or more of those devices may include an on-board computer, an electronic control unit, a display unit, a server, a desktop computer, a laptop computer, a tablet computer, or other mobile device, such as a palm top computer, a cell phone, a smart phone, a multimedia player, a personal digital assistant, etc.

In some examples, remote server architecture 500 may include cybersecurity measures. Without limitation, these measures may include encryption of data on storage devices, encryption of data sent between network nodes, authentication of people or processes accessing data, as well as the use of ledgers for recording metadata, data, data transfers, data accesses, and data transformations. In some examples, the ledgers may be distributed and immutable (e.g., implemented as blockchain).

Figure 7:
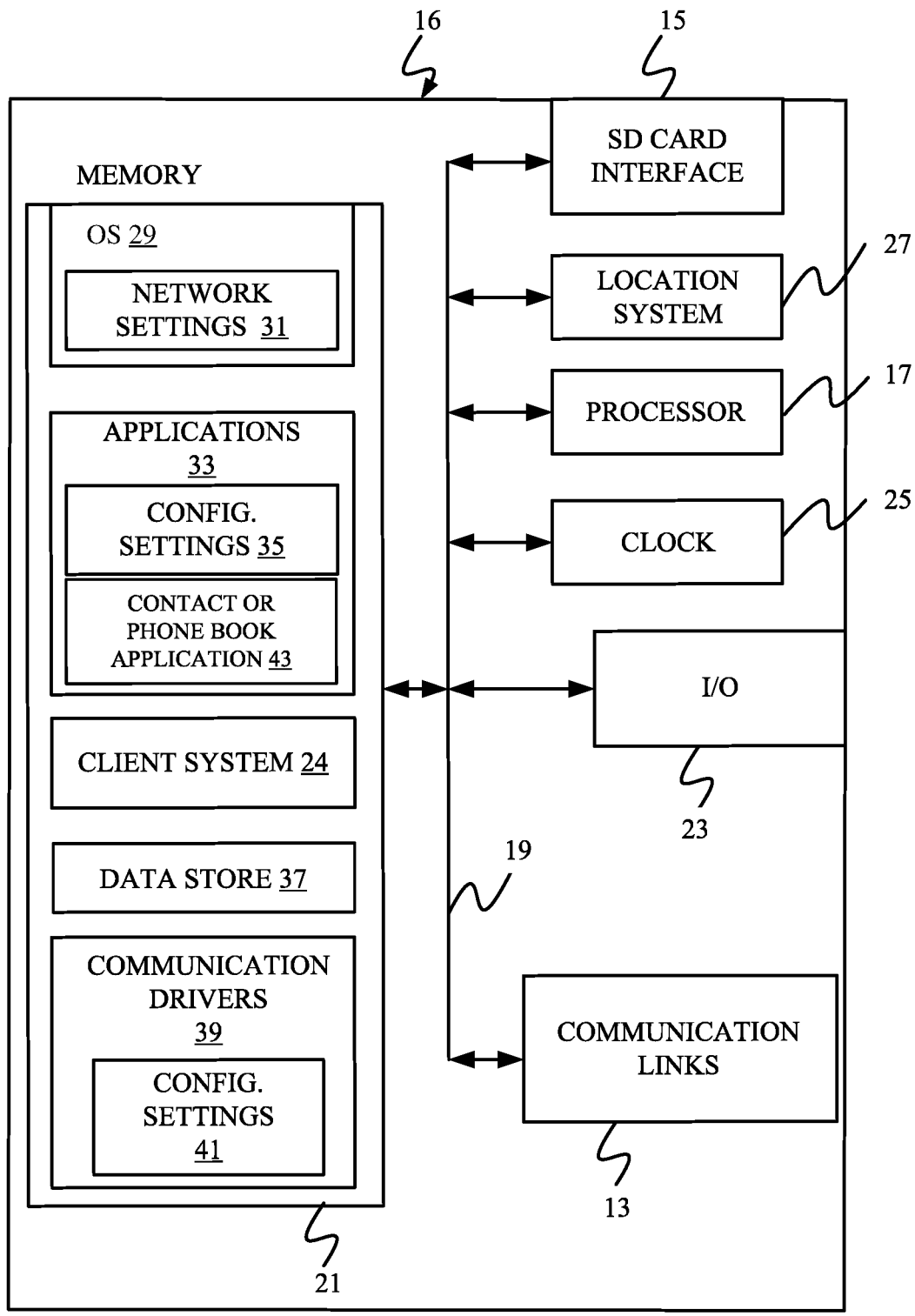
FIGS. 7-9 show examples of mobile devices that can be used in an agricultural harvester.
Figure 8:
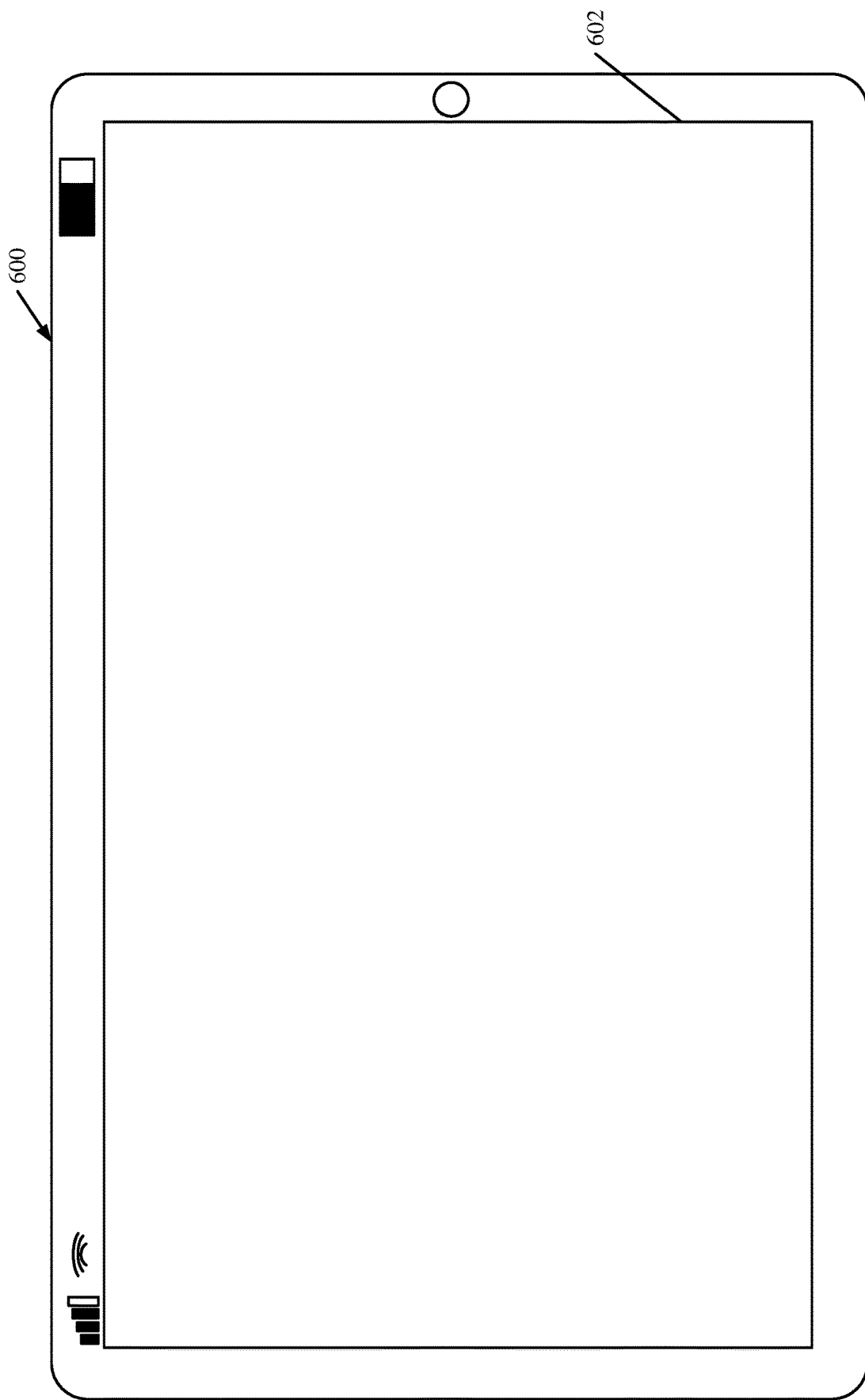
Figure 9:
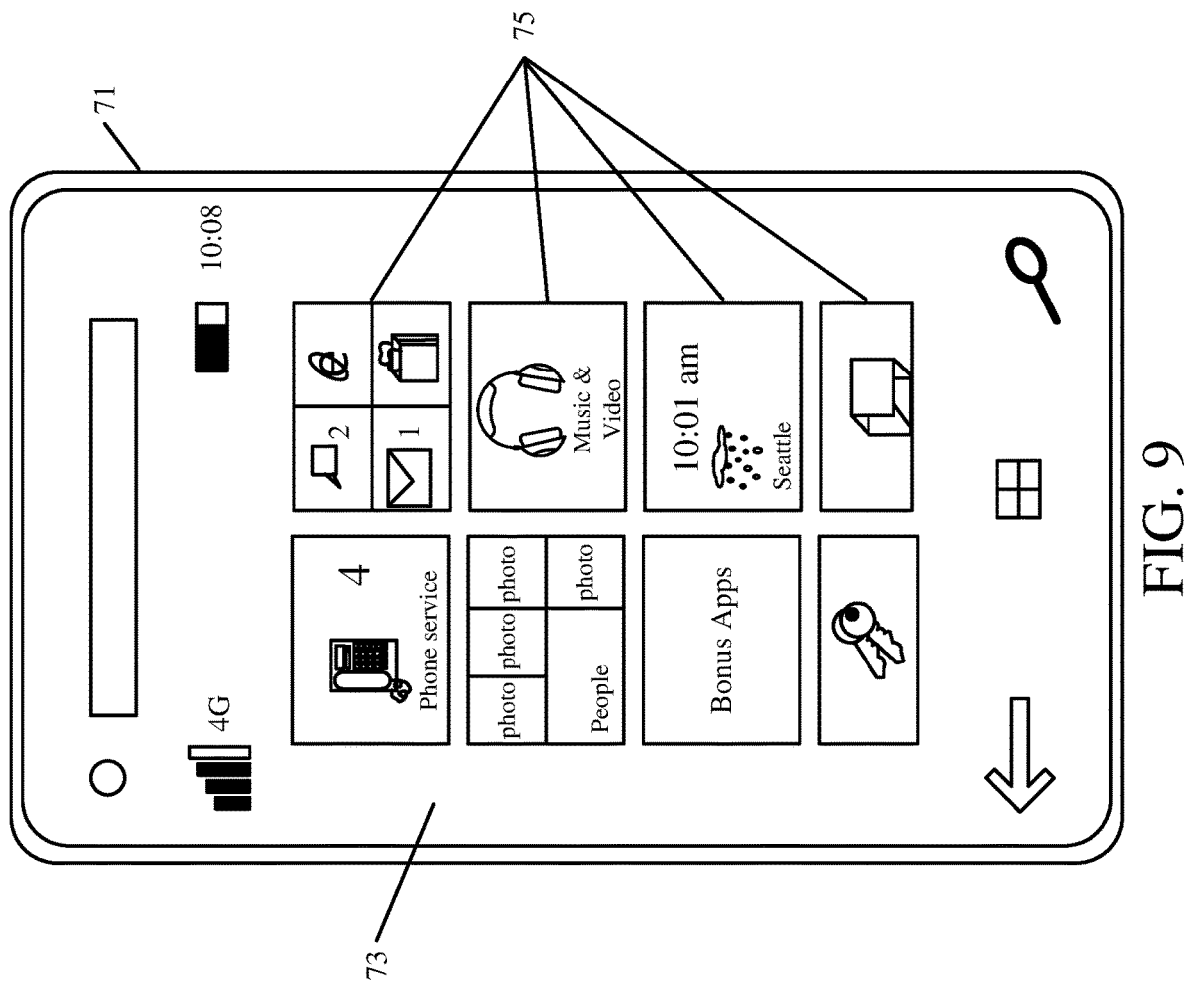

FIG. 7 is a simplified block diagram of one illustrative example of a handheld or mobile computing device that can be used as a user's or client's hand held device 16, in which the present system (or parts of it) can be deployed. For instance, a mobile device can be deployed in the operator compartment of agricultural harvester 100 for use in generating, processing, or displaying the maps discussed above. FIGS. 8-9 are examples of handheld or mobile devices.

FIG. 7 provides a general block diagram of the components of a client device 16 that can run some components shown in FIG. 2, that interacts with them, or both. In the device 16, a communications link 13 is provided that allows the handheld device to communicate with other computing devices and under some examples provides a channel for receiving information automatically, such as by scanning. Examples of communications link 13 include allowing communication though one or more communication protocols, such as wireless services used to provide cellular access to a network, as well as protocols that provide local wireless connections to networks.

In other examples, applications can be received on a removable Secure Digital (SD) card that is connected to an interface 15. Interface 15 and communication links 13 communicate with a processor 17 (which can also embody processors or servers from other FIGS.) along a bus 19 that is also connected to memory 21 and input/output (I/O) components 23, as well as clock 25 and location system 27.

I/O components 23, in one example, are provided to facilitate input and output operations. I/O components 23 for various examples of the device 16 can include input components such as buttons, touch sensors, optical sensors, microphones, touch screens, proximity sensors, accelerometers, orientation sensors and output components such as a display device, a speaker, and or a printer port. Other I/O components 23 can be used as well.

Clock 25 illustratively comprises a real time clock component that outputs a time and date. It can also, illustratively, provide timing functions for processor 17.

Location system 27 illustratively includes a component that outputs a current geographical location of device 16. This can include, for instance, a global positioning system (GPS) receiver, a LORAN system, a dead reckoning system, a cellular triangulation system, or other positioning system. Location system 27 can also include, for example, mapping software or navigation software that generates desired maps, navigation routes and other geographic functions.

Memory 21 stores operating system 29, network settings 31, applications 33, application configuration settings 35, data store 37, communication drivers 39, and communication configuration settings 41. Memory 21 can include all types of tangible volatile and non-volatile computer-readable memory devices. Memory 21 may also include computer storage media (described below). Memory 21 stores computer readable instructions that, when executed by processor 17, cause the processor to perform computer-implemented steps or functions according to the instructions. Processor 17 may be activated by other components to facilitate their functionality as well.

FIG. 8 shows one example in which device 16 is a tablet computer 600. In FIG. 8, computer 600 is shown with user interface display screen 602. Screen 602 can be a touch screen or a pen-enabled interface that receives inputs from a pen or stylus. Tablet computer 600 may also use an on-screen virtual keyboard. Of course, computer 600 might also be attached to a keyboard or other user input device through a suitable attachment mechanism, such as a wireless link or USB port, for instance. Computer 600 may also illustratively receive voice inputs as well.

FIG. 9 is similar to FIG. 8 except that the device is a smart phone 71. Smart phone has a touch sensitive display 73 that displays icons or tiles or other user input mechanisms 75. Mechanisms 75 can be used by a user to run applications, make calls, perform data transfer operations, etc. In general, smart phone 71 is built on a mobile operating system and offers more advanced computing capability and connectivity than a feature phone.

Note that other forms of the devices 16 are possible.

Figure 10:
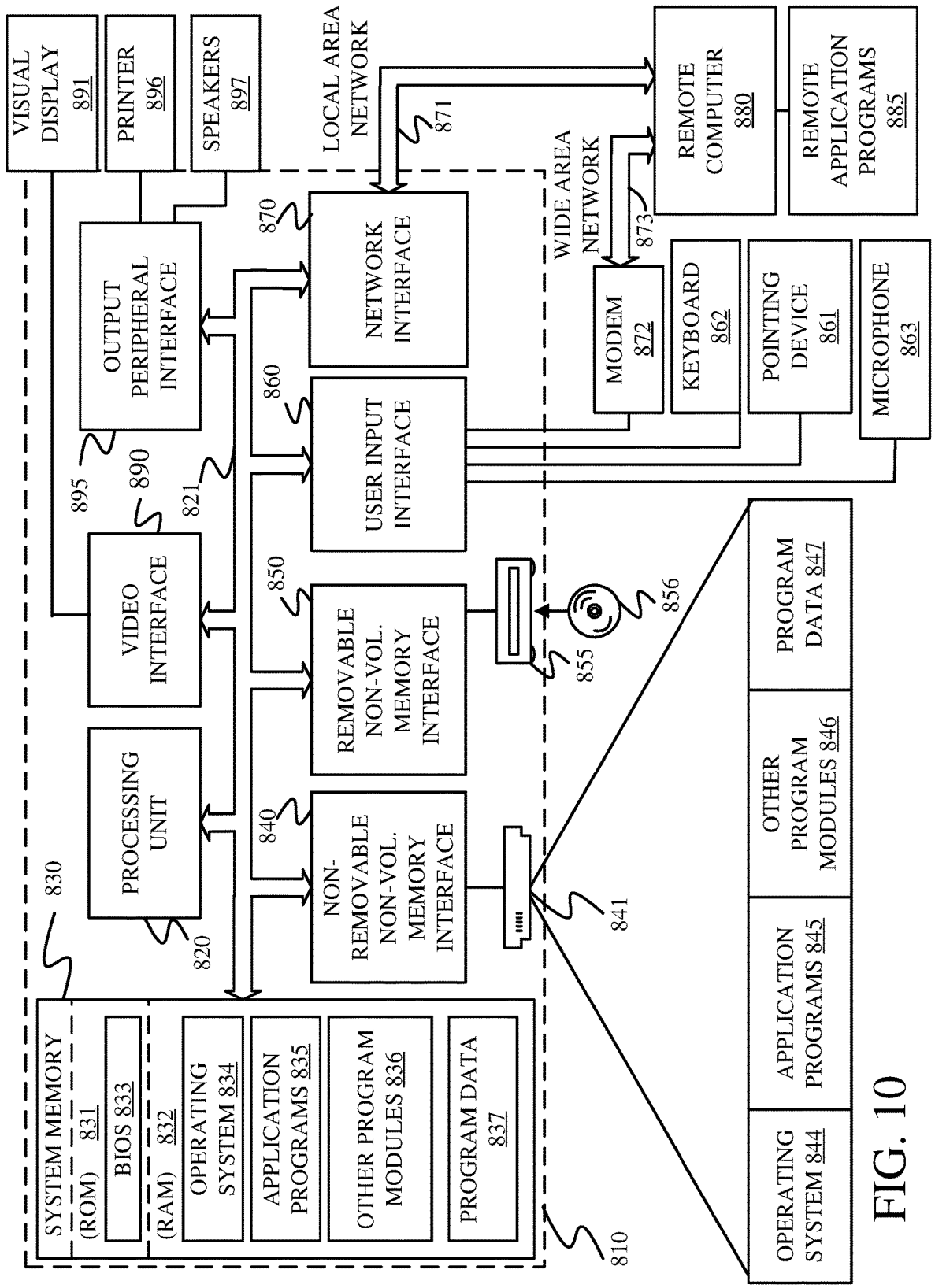
FIG. 10 is a block diagram showing one example of a computing environment that can be used in an agricultural harvester and the architectures illustrated in previous figures.

FIG. 10 is one example of a computing environment in which elements of FIG. 2 can be deployed. With reference to FIG. 10, an example system for implementing some embodiments includes a computing device in the form of a computer 810 programmed to operate as discussed above. Components of computer 810 may include, but are not limited to, a processing unit 820 (which can comprise processors or servers from previous FIGS.), a system memory 830, and a system bus 821 that couples various system components including the system memory to the processing unit 820. The system bus 821 may be any of several types of bus structures including a memory bus or memory controller, a peripheral bus, and a local bus using any of a variety of bus architectures. Memory and programs described with respect to FIG. 2 can be deployed in corresponding portions of FIG. 10.

Computer 810 typically includes a variety of computer readable media. Computer readable media may be any available media that can be accessed by computer 810 and includes both volatile and nonvolatile media, removable and non-removable media. By way of example, and not limitation, computer readable media may comprise computer storage media and communication media. Computer storage media is different from, and does not include, a modulated data signal or carrier wave. Computer readable media includes hardware storage media including both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 810. Communication media may embody computer readable instructions, data structures, program modules or other data in a transport mechanism and includes any information delivery media. The term "modulated data signal" means a signal that has one or more of its characteristics set or changed in such a manner as to encode information in the signal.

The system memory 830 includes computer storage media in the form of volatile and/or nonvolatile memory or both such as read only memory (ROM) 831 and random access memory (RAM) 832. A basic input/output system 833 (BIOS), containing the basic routines that help to transfer information between elements within computer 810, such as during start-up, is typically stored in ROM 831. RAM 832 typically contains data or program modules or both that are immediately accessible to and/or presently being operated on by processing unit 820. By way of example, and not limitation, FIG. 10 illustrates operating system 834, application programs 835, other program modules 836, and program data 837.

The computer 810 may also include other removable/non-removable volatile/nonvolatile computer storage media. By way of example only, FIG. 10 illustrates a hard disk drive 841 that reads from or writes to non-removable, nonvolatile magnetic media, an optical disk drive 855, and nonvolatile optical disk 856. The hard disk drive 841 is typically connected to the system bus 821 through a non-removable memory interface such as interface 840, and optical disk drive 855 are typically connected to the system bus 821 by a removable memory interface, such as interface 850.

Alternatively, or in addition, the functionality described herein can be performed, at least in part, by one or more hardware logic components. For example, and without limitation, illustrative types of hardware logic components that can be used include Field-programmable Gate Arrays (FPGAs), Application-specific Integrated Circuits (e.g., ASICs), Application-specific Standard Products (e.g., ASSPs), System-on-a-chip systems (SOCs), Complex Programmable Logic Devices (CPLDs), etc.

The drives and their associated computer storage media discussed above and illustrated in FIG. 10, provide storage of computer readable instructions, data structures, program modules and other data for the computer 810. In FIG. 10, for example, hard disk drive 841 is illustrated as storing operating system 844, application programs 845, other program modules 846, and program data 847. Note that these components can either be the same as or different from operating system 834, application programs 835, other program modules 836, and program data 837.

A user may enter commands and information into the computer 810 through input devices such as a keyboard 862, a microphone 863, and a pointing device 861, such as a mouse, trackball or touch pad. Other input devices (not shown) may include a joystick, game pad, satellite dish, scanner, or the like. These and other input devices are often connected to the processing unit 820 through a user input interface 860 that is coupled to the system bus, but may be connected by other interface and bus structures. A visual display 891 or other type of display device is also connected to the system bus 821 via an interface, such as a video interface 890. In addition to the monitor, computers may also include other peripheral output devices such as speakers 897 and printer 896, which may be connected through an output peripheral interface 895.

The computer 810 is operated in a networked environment using logical connections (such as a controller area network—CAN, local area network—LAN, or wide area network WAN) to one or more remote computers, such as a remote computer 880.

When used in a LAN networking environment, the computer 810 is connected to the LAN 871 through a network interface or adapter 870. When used in a WAN networking environment, the computer 810 typically includes a modem 872 or other means for establishing communications over the WAN 873, such as the Internet. In a networked environment, program modules may be stored in a remote memory storage device. FIG. 10 illustrates, for example, that remote application programs 885 can reside on remote computer 880.

It should also be noted that the different examples described herein can be combined in different ways. That is, parts of one or more examples can be combined with parts of one or more other examples. All of this is contemplated herein.

Example 1 is an agricultural work machine, comprising:
a communication system that receives a prior information map that includes values of an agricultural characteristic corresponding to different geographic locations in a field;
a geographic position sensor that detects a geographic location of the agricultural work machine;
an in-situ sensor that detects a value of a biomass characteristic corresponding to the geographic location;
a predictive model generator that generates a predictive agricultural model that models a relationship between the agricultural characteristic and the biomass characteristic based on a value of the agricultural characteristic in the prior information map at the geographic location and the value of the biomass characteristic sensed by the in-situ sensor corresponding to the geographic location; and
a predictive map generator that generates a functional predictive agricultural map of the field based on the values of the agricultural characteristic in the prior information map and based on the predictive agricultural model, the functional predictive agricultural map mapping predictive values of the biomass characteristic to the different geographic locations in the field.

Example 2 is the agricultural work machine of any or all previous claims, wherein the predictive map generator configures the functional predictive agricultural map for consumption by a control system that generates control signals to control a controllable subsystem on the agricultural work machine based on the functional predictive agricultural map.

Example 3 is the agricultural work machine of any or all previous claims, wherein the in-situ sensor on the agricultural work machine is configured to detect, as the value of the biomass characteristic, a value of a vegetation characteristic corresponding to the geographic location.

Example 4 is the agricultural work machine of any or all previous claims, wherein the in-situ sensor comprises:
an image detector configured to detect an image indicative of the vegetation characteristic.

Example 5 is the agricultural work machine of any or all previous claims, wherein the image detector is oriented to detect an image of at least a portion of the field and further comprises:
an image processing system configured to process the image to identify the value of the vegetation characteristic in the image indicative of the vegetation characteristic.

Example 6 is the agricultural work machine of any or all previous claims, wherein the in-situ sensor generates a sensor signal indicative of a value of the vegetation characteristic and further comprises:
a processing system that receives the sensor signal and is configured to identify, as the value of the vegetation characteristic, a value of vegetation height indicative of a height of vegetation corresponding to the geographic location.

Example 7 is the agricultural work machine of any or all previous claims, wherein the prior information map comprises a prior vegetative index map that maps, as the agricultural characteristic, vegetative index values to the different geographic locations in the field, and
wherein the predictive model generator is configured to identify a relationship between the vegetative index values and the vegetation height based on the value of the vegetation height value detected by the in-situ sensor corresponding to the geographic location and the vegetative index value, in the vegetative index map, at the geographic location, the predictive agricultural model being configured to receive a vegetative index value as a model input and generate a predictive value of the vegetation height as a model output based on the identified relationship.

Example 8 is the agricultural work machine of any or all previous claims, wherein the in-situ sensor generates a sensor signal indicative of a value of the vegetation characteristic and further comprises:
a processing system that receives the sensor signal and is configured to identify, as the value of the vegetation characteristic, a value of a vegetation density indicative of a density of vegetation corresponding to the geographic location.

Example 9 is the agricultural work machine of any or all previous claims, wherein the prior information map comprises a prior vegetative index map that maps, as the agricultural characteristic, vegetative index values to the different geographic locations in the field; and
wherein the predictive model generator is configured to identify a relationship between the vegetative index values and the vegetation density based on the value of the vegetation density value detected by the in-situ sensor corresponding to the geographic location and the vegetative index value, in the vegetative index map, at the geographic location, the predictive agricultural model being configured to receive a vegetative index value as a model input and generate a predictive value of the vegetation density as a model output based on the identified relationship.

Example 10 is the agricultural work machine of any or all previous claims, wherein the in-situ sensor generates a sensor signal indicative of a value of the vegetation characteristic and further comprises:
a processing system that receives the sensor signal and is configured to identify, as the value of the vegetation characteristic, a value of a vegetation volume indicative of a volume of vegetation corresponding to the geographic location.

Example 11 is the agricultural work machine of any or all previous claims, wherein the prior information map comprises a prior vegetative index map that maps, as the agricultural characteristic, vegetative index values to the different geographic locations in the field, and
wherein the predictive model generator is configured to identify a relationship between the vegetative index values and the vegetation volume based on the value of vegetation volume detected by the in-situ sensor corresponding to the geographic location and the vegetative index value, in the vegetative index map, at the geographic location, the predictive agricultural model being configured to receive a vegetative index value as a model input and generate a predictive value of vegetation volume as a model output based on the identified relationship.

Example 12 is the agricultural work machine of any or all previous claims, wherein the in-situ sensor on the agricultural machine is configured to detect, as the value of the biomass characteristic, a value of a machine operating characteristic corresponding to the geographic location and generate a sensor signal indicative of the value of the machine operating characteristic, and wherein the work machine further comprises:
a processing system that receives the sensor signal and is configured to identify, as the value of the machine operating characteristic, a value of a threshing rotor drive force indicative of a force used to drive the threshing rotor corresponding to the geographic location.

Example 13 is the agricultural work machine of any or all previous claims, wherein the prior information map comprises a prior vegetative index map that maps, as the agricultural characteristic, vegetative index values to the different geographic locations in the field, and
wherein the predictive model generator is configured to identify a relationship between the vegetative index values and the threshing rotor drive force based on the detected value of the thresher rotor drive force, indicative of the force used to drive the threshing rotor, corresponding to the geographic location and the vegetative index value, in the vegetative index map, at the geographic location, the predictive agricultural model being configured to receive a vegetative index value as a model input and generate a predictive value of the threshing rotor drive force as a model output based on the identified relationship.

Example 14 is a computer implemented method of generating a functional predictive agricultural map, comprising:
receiving a prior information map, at an agricultural work machine, that indicates values of an agricultural characteristic corresponding to different geographic locations in a field;
detecting a geographic location of the agricultural work machine;
detecting, with an in-situ sensor, a value of a biomass characteristic corresponding to the geographic location;
generating a predictive agricultural model that models a relationship between the agricultural characteristic and the biomass characteristic; and
controlling a predictive map generator to generate the functional predictive agricultural map of the field that maps predictive values of the biomass characteristic to the different geographic locations in the field based on the values of the agricultural characteristic in the prior information map and the predictive agricultural model.

Example 15 is the computer implemented method of any or all previous claims, and further comprising:
configuring the functional predictive agricultural map for a control system that generates control signals to control a controllable subsystem on the agricultural work machine based on the functional predictive agricultural map.

Example 16 is the computer implemented method of any or all previous claims, wherein detecting, with an in-situ sensor, a value of the biomass characteristic comprises detecting a value of a vegetation characteristic corresponding to the geographic location, and
wherein receiving the prior information map comprises receiving a prior vegetative index map that maps, as the agricultural characteristic, vegetative index values to the different geographic locations in the field.

Example 17 is the computer implemented method of any or all previous claims, wherein detecting, with an in-situ sensor, a value of the biomass characteristic comprises detecting a value of a threshing rotor drive force corresponding to the geographic location, and
wherein receiving the prior information map comprises receiving a prior vegetative index map that maps, as the agricultural characteristic, vegetative index values to the different geographic locations in the field.

Example 18 is an agricultural work machine, comprising:
a communication system that receives a prior vegetative index map that indicates vegetative index values corresponding to different geographic locations in a field;
a geographic position sensor that detects a geographic location of the agricultural work machine;
an in-situ sensor that detects a biomass characteristic value, of a biomass characteristic, corresponding to the geographic location;
a predictive model generator that generates a predictive biomass model that models a relationship between the vegetative index values and the biomass characteristic based on a vegetative index value in the prior vegetative index map at the geographic location and the biomass characteristic value of the biomass characteristic detected by the in-situ sensor corresponding to the geographic location; and a predictive map generator that generates a functional predictive biomass map of the field based on the vegetative index values in the prior vegetative index map and based on the predictive biomass model, the predictive biomass map mapping predictive biomass characteristic values to the different geographic locations in the field.

Example 19 is the agricultural work machine of any or all previous claims, wherein the biomass characteristic is a vegetation characteristic and the in-situ sensor comprises:

an image detector configured to detect an image indicative of the vegetation characteristic; and an image processing system configured to process the image indicative of the vegetation characteristic to identify, as the biomass characteristic value, a vegetation characteristic value in the image indicative of the vegetation characteristic.

Example 20 is the agricultural work machine of any or all previous claims, wherein the biomass characteristic is a machine operating characteristic and the in-situ sensor comprises:

a threshing rotor drive force sensor configured to detect a force used to drive a threshing rotor and generate a sensor signal indicative of the force used to drive the threshing rotor; and a processing system configured to identify, as the biomass characteristic value, a value of the threshing rotor drive force based on the sensor signal.

Although the subject matter has been described in language specific to structural features or methodological acts, it is to be understood that the subject matter defined in the appended claims is not necessarily limited to the specific features or acts described above. Rather, the specific features and acts described above are disclosed as example forms of the claims.

What is claimed is:

1. An agricultural system comprising:
a communication system that receives a prior information map that includes values of an agricultural characteristic corresponding to different geographic locations in a field;
a geographic position sensor that detects a geographic location of an agricultural work machine;
an in-situ sensor that detects a value indicative of a biomass characteristic corresponding to the geographic location and generates a sensor signal indicative of the value;
a processing system that receives the sensor signal and is configured to identify, as a value of the biomass characteristic, a value of vegetation volume indicative of a volume of vegetation corresponding to the geographic location;
a predictive model generator that generates a predictive agricultural model that models a relationship between the agricultural characteristic and the biomass characteristic based on a value of the agricultural characteristic in the prior information map at the geographic location and the value of the biomass characteristic detected by the in-situ sensor corresponding to the geographic location; and
a predictive map generator that generates a functional predictive agricultural map of the field based on the values of the agricultural characteristic in the prior information map and based on the predictive agricultural model, the functional predictive agricultural map mapping predictive values of the biomass characteristic to the different geographic locations in the field.

2. The agricultural system of claim 1, wherein the predictive map generator configures the functional predictive agricultural map for consumption by a control system that generates control signals to control a controllable subsystem on the agricultural work machine based on the functional predictive agricultural map.

3. The agricultural system of claim 1, wherein the prior information map comprises a prior vegetative index map that maps, as the values of the agricultural characteristic, vegetative index values corresponding to the different geographic locations in the field.

4. The agricultural system of claim 1, wherein the in-situ sensor comprises:
an image detector configured to detect an image indicative of the value of the biomass characteristic.

5. The agricultural system of claim 4, wherein the image detector is oriented to detect an image of at least a portion of the field and wherein the processing system comprises:
an image processing system configured to process the image to identify the value of the vegetation volume in the image indicative of the value of the biomass characteristic.

6. The agricultural system of claim 1, wherein the in-situ sensor detects a value of an additional biomass characteristic corresponding to the geographic location and generates the sensor signal indicative of the value indicative of the additional biomass characteristic and wherein the processing system is configured to:
receive the sensor signal and identify, as a value of the additional biomass characteristic, a value of vegetation height indicative of a height of vegetation corresponding to the geographic location.

7. The agricultural system of claim 6, wherein the prior information map comprises a prior vegetative index map that maps, as the values of the agricultural characteristic, vegetative index values to the different geographic locations in the field, and
wherein the predictive model generator is configured to identify a relationship between vegetative index values and values of vegetation height based on the value of the vegetation height value detected by the in-situ sensor corresponding to the geographic location and the vegetative index value, in the vegetative index map, at the geographic location, the predictive agricultural model being configured to receive a vegetative index value as a model input and generate a predictive value of vegetation height as a model output based on the identified relationship.

8. The agricultural system of claim 1, wherein the in-situ sensor detects a value indicative of an additional biomass characteristic corresponding to the geographic location and generates the sensor signal indicative of the value indicative of the additional biomass characteristic and wherein the processing system is configured to:
Receive the sensor signal and identify, as a value of the additional biomass characteristic, a value of a vegetation density indicative of a density of vegetation corresponding to the geographic location.

9. The agricultural system of claim 8, wherein the prior information map comprises a prior vegetative index map that maps, as the values of the agricultural characteristic, vegetative index values to the different geographic locations in the field; and
 wherein the predictive model generator is configured to identify a relationship between vegetative index values and values of vegetation density based on the value of the vegetation density value detected by the in-situ sensor corresponding to the geographic location and the vegetative index value, in the vegetative index map, at the geographic location, the predictive agricultural model being configured to receive a vegetative index value as a model input and generate a predictive value of vegetation density as a model output based on the identified relationship.

10. The agricultural system of claim 1, and further comprising an additional in-situ sensor configured to detect, as a value indicative of an additional biomass characteristic, a value of a machine operating characteristic corresponding to the geographic location and generate a sensor signal indicative of the value of the machine operating characteristic, and wherein the processing system is configured to:
 Receive the sensor signal indicative of the value of the machine operating characteristic and is configured to identify, as the value of the machine operating characteristic, a value of a threshing rotor drive force indicative of a force used to drive a threshing rotor corresponding to the geographic location.

11. The agricultural system of claim 10, wherein the prior information map comprises a prior vegetative index map that maps, as the values of the agricultural characteristic, vegetative index values to the different geographic locations in the field, and
 wherein the predictive model generator is configured to identify a relationship between vegetative index values and values of threshing rotor drive force based on the detected value of the thresher rotor drive force, indicative of the force used to drive the threshing rotor, corresponding to the geographic location and the vegetative index value, in the vegetative index map, at the geographic location, the predictive agricultural model being configured to receive a vegetative index value as a model input and generate a predictive value of threshing rotor drive force as a model output based on the identified relationship.

12. A computer implemented method of generating a functional predictive agricultural map, comprising:
 receiving a prior information map that indicates values of an agricultural characteristic corresponding to different geographic locations in a field;
 detecting a geographic location of an agricultural work machine;
 detecting, with an in-situ sensor, a value indicative of a biomass characteristic corresponding to the geographic location and generating a sensor signal indicative of the value;
 processing the sensor signal to identify, as a value of the biomass characteristic, a value of vegetation volume indicative of a volume of vegetation corresponding to the geographic location;
 generating a predictive agricultural model that models a relationship between the agricultural characteristic and the biomass characteristic; and
 controlling a predictive map generator to generate the functional predictive agricultural map of the field that maps predictive values of the biomass characteristic to the different geographic locations in the field based on the values of the agricultural characteristic in the prior information map and the predictive agricultural model.

13. The computer implemented method of claim 12, and further comprising:
 configuring the functional predictive agricultural map for a control system that generates control signals to control a controllable subsystem on the agricultural work machine based on the functional predictive agricultural map.

14. The computer implemented method of claim 12, wherein receiving the prior information map comprises receiving a prior vegetative index map that maps, as the values of the agricultural characteristic, vegetative index values to the different geographic locations in the field.

15. The computer implemented method of claim 12, and further comprising detecting, with an additional in-situ sensor, as a value indicative of an additional biomass characteristic, a value of a threshing rotor drive force corresponding to the geographic location, and
 wherein receiving the prior information map comprises receiving a prior vegetative index map that maps, as the values of the agricultural characteristic, vegetative index values to the different geographic locations in the field.

16. An agricultural system comprising:
 a communication system that receives a prior vegetative index map that indicates vegetative index values corresponding to different geographic locations in a field;
 a geographic position sensor that detects a geographic location of an agricultural work machine;
 an in-situ sensor that detects, as a biomass characteristic corresponding to the geographic location, a force used to drive a threshing rotor and generates a sensor signal indicative of the force used to drive the threshing rotor;
 a processing system that receives the sensor signal and is configured to identify, as a value of the biomass characteristic, a value of the force used to drive the threshing rotor;
 a predictive model generator that generates a predictive biomass model that models a relationship between the vegetative index values and values of the biomass characteristic based on a vegetative index value in the prior vegetative index map at the geographic location and the value of the biomass characteristic detected by the in-situ sensor corresponding to the geographic location; and
 a predictive map generator that generates a functional predictive biomass map of the field based on the vegetative index values in the prior vegetative index map and based on the predictive biomass model, the predictive biomass map mapping predictive biomass characteristic values to the different geographic locations in the field.

17. The agricultural system of claim 16, and further comprising an additional in-situ sensor configured to detect, as an additional biomass characteristic corresponding to the geographic location,
 a vegetation characteristic, the additional in-situ sensor comprising:
  an image detector configured to detect an image indicative of the vegetation characteristic; and
  an image processing system configured to process the image indicative of the vegetation characteristic to identify, as a value of the additional biomass characteristic, a vegetation characteristic value in the image indicative of the vegetation characteristic.

18. The agricultural system of claim 16, wherein the predictive map generator configures the functional predictive biomass map for consumption by a control system that generates control signals to control a controllable subsystem on the agricultural work machine based on the functional predictive biomass map.

\* \* \* \* \*